US012594348B2

(12) United States Patent
Wilson et al.

(10) Patent No.: US 12,594,348 B2
(45) Date of Patent: Apr. 7, 2026

(54) COMPOSITIONS FOR TREATING FRIEDREICH'S ATAXIA

(71) Applicant: The Trustees of the University of Pennsylvania, Philadelphia, PA (US)

(72) Inventors: James M. Wilson, Philadelphia, PA (US); Christian Hinderer, Baltimore, MD (US); Nimrod Miller, Berwyn, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 897 days.

(21) Appl. No.: 17/787,013

(22) PCT Filed: Dec. 18, 2020

(86) PCT No.: PCT/US2020/066167

§ 371 (c)(1),
(2) Date: Jun. 17, 2022

(87) PCT Pub. No.: WO2021/127533

PCT Pub. Date: Jun. 24, 2021

(65) Prior Publication Data

US 2023/0211012 A1 Jul. 6, 2023

Related U.S. Application Data

(60) Provisional application No. 62/950,834, filed on Dec. 19, 2019.

(51) Int. Cl.
| | |
|---|---|
| *A61K 48/00* | (2006.01) |
| *A61K 47/02* | (2006.01) |
| *A61P 25/28* | (2006.01) |
| *C12N 15/86* | (2006.01) |

(52) U.S. Cl.
CPC .......... *A61K 48/0008* (2013.01); *A61K 47/02* (2013.01); *A61K 48/0075* (2013.01); *A61P 25/28* (2018.01); *C12N 15/86* (2013.01); *C12N 2750/14122* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | | |
|---|---|---|---|
| 5,139,941 | A | 8/1992 | Muzyczka et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowiz et al. |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,439,065 | B2 | 10/2008 | Ferrari et al. |
| 7,588,772 | B2 | 9/2009 | Kay et al. |
| 7,906,111 | B2 | 3/2011 | Wilson et al. |
| 8,734,809 | B2 | 5/2014 | Gao et al. |
| 8,927,514 | B2 | 1/2015 | Chatterjee et al. |
| 2011/0059889 | A1 | 3/2011 | Mezo et al. |
| 2013/0045186 | A1 | 2/2013 | Gao et al. |
| 2015/0344911 | A1 | 12/2015 | Chatterjee et al. |
| 2017/0043035 | A1 | 2/2017 | Wilson et al. |
| 2017/0128528 | A1 | 5/2017 | Samulski |
| 2018/0021364 | A1 | 1/2018 | Stewart et al. |
| 2018/0117178 | A1 | 5/2018 | Corti et al. |
| 2020/0056159 | A1 | 2/2020 | Wilson et al. |
| 2020/0384073 | A1 | 12/2020 | Samulski |
| 2021/0077553 | A1 | 3/2021 | Hordeaux et al. |

FOREIGN PATENT DOCUMENTS

| | | |
|---|---|---|
| CA | 2947584 | 5/2017 |
| WO | WO-2003/042397 | 5/2003 |
| WO | WO-2005/033321 | 4/2005 |
| WO | WO-2006/110689 | 10/2006 |
| WO | WO-2011/126808 | 10/2011 |
| WO | WO-2013/049493 | 4/2013 |
| WO | WO-2016/049230 | 3/2016 |
| WO | WO-2016/172155 | 10/2016 |
| WO | WO-2016/172659 | 10/2016 |
| WO | WO-2017/160360 | 9/2017 |
| WO | WO-2018/160582 | 9/2018 |

(Continued)

OTHER PUBLICATIONS

Sehara et al., "Persistent Expression of Dopamine-Synthesizing Enzymes 15 Years After Gene Transfer in a Primate Model of Parkinson's Disease," Human Gene Therapy Clinical Development, Jun. 2017, vol. 28:74-79.

Strawer et al., "Pharmacological therapeutics in Friedreich ataxia: the present state," Expert Review of Neurotherapeutics, Sep. 2017, vol. 17:895-907.

Abeti et al., "Targeting lipid peroxidation and mitochondrial imbalance in Friedreich's ataxia," Pharmacological Research, Sep. 2015, vol. 99:344-350.

Campuzano et al., "Friedreich's ataxia: autosomal recessive disease caused by an intronic GAA triplet repeat expansion," Science, Mar. 1996, vol. 271(5254):1423.

Rojsajjakul et al., "Quantification of human mature frataxin protein expression in nonhuman primate hearts after gene therapy," Communications Biology, Oct. 2023, vol. 6:1093.

(Continued)

*Primary Examiner* — Allison M Fox
*Assistant Examiner* — Gina Pronzati
(74) *Attorney, Agent, or Firm* — Howson & Howson; Cathy A. Kodroff

(57) ABSTRACT

A recombinant adeno-associated virus (rAAV) comprising an AAV capsid and a vector genome comprising a frataxin gene is provided. Also provided is a composition containing an effective amount of rAAV to ameliorate symptoms of Freidreich's ataxia, including, e.g., reduction in progression towards neurocognitive decline and/or cardiomyopathy.

22 Claims, 7 Drawing Sheets

Specification includes a Sequence Listing.

(56) References Cited

FOREIGN PATENT DOCUMENTS

| WO | WO-2019/028306 | 2/2019 |
| WO | WO-2019/152816 | 8/2019 |
| WO | WO-2020/132455 | 6/2020 |
| WO | WO-2020/159970 | 8/2020 |
| WO | WO-2020/223231 | 11/2020 |
| WO | WO-2021/127533 | 6/2021 |

OTHER PUBLICATIONS

Extended European Search Report issued on counterpart European Patent Application No. 20901671.6, dated Feb. 27, 2024, pp. 1-8.

Jakob et al., "No evidence for germ-line transmission following prenatal and early postnatal AAV-mediated gene delivery," J Gene Med., vol. 7(5):630-7, May 2005.

Worgall et al., "Treatment of late infantile neuronal ceroid lipofuscinosis by CNS administration of a serotype 2 adeno-associated virus expressing CLN2 cDNA," Hum Gene Ther., vol. 19(5):463-74, May 2008.

FDA "FDA Guidance for Industry: Long Term Follow-Up after Administration of Human Gene Therapy Products" (Jan. 2020).

FDA "Guidance for Industry—cGMP for Phase 1 Investigational Drugs," Jul. 2008.

Flanigan, Voyager Therapeutics Corporate Presentation, ASGCT Annual Meeting, May 2018.

Green and Sambrook (eds.), Molecular Cloning: A Laboratory Manual, Cold Spring Harbor Press, Cold Spring Harbor, NY, Jan. 2012.

Nei and S. Kumar, "Neighbor Joining Method," in Molecular Evolution and Phylogenetics, pp. 103-110, Oxford University Press, New York, Jan. 2000.

Sambrook et al. (eds.), "Molecular Cloning. A Laboratory Manual", 2d ed., Cold Spring Harbor Laboratory, New York, pp. 16.5-16.6, Jan. 1989.

Carter, in "Handbook of Parvoviruses", ed., P. Tijsser, CRC Press, pp. 155-168, Jan. 1990.

Grieger and Samulski, "Adeno-associated virus as a gene therapy vector: Vector development, production and clinical applications," Adv. Biochem. Engin/Biotechnol. vol. 99:119-145, Feb. 2005.

Mandel et al., "Clinical trials in neurological disorders using AAV vectors: promises and challenges," Curr Opin Mol Ther., vol. 6(5):482-90, Oct. 2004.

Bell et al., "Motor neuron transduction after intracisternal delivery of AAV9 in a cynomolgus macaque," Hum Gene Ther Methods., vol. 26(2):43-4, Apr. 2015.

Buning et al., "Recent developments in adeno-associated virus vector technology," J. Gene Med., vol. 10:717-733, Jul. 2008.

Couto et al., "Direct exposure of mouse spermatozoa to very high concentrations of a serotype-2 adeno-associated virus gene therapy vector fails to lead to germ cell transduction," Hum Gene Ther., vol. 15(3):287-91, Mar. 2004.

Donsante et al., "Observed incidence of tumorigenesis in long-term rodent studies of rAAV vectors," Gene Ther., vol. 8(17):1343-6, Sep. 2001.

Grimm et al., "Titration of AAV-2 particles via a novel capsid ELISA: packaging of genomes can limit production of recombinant AAV-2," Gene Therapy, vol. 6:1322-1330, Jul. 1999.

Hinderer et al., "Delivery of an adeno-associated virus vector into cerebrospinal fluid attenuates central nervous system disease in Mucopolysaccharidosis Type II mice," Hum Gene Ther., vol. 27(11):906-915, Nov. 2016.

Janson et al., "Clinical protocol. Gene therapy of Canavan disease: AAV-2 vector for neurosurgical delivery of aspartoacylase gene (ASPA) to the human brain," Hum Gene Ther., vol. 13(11):1391-412, Jul. 2002.

Jin et al., "Direct Liquid Chromatography/Mass Spectrometry Analysis for Complete Characterization of Recombinant Adeno-Associated Virus Capsid Proteins," Hu Gene Therapy Methods, vol. 28(5):255-267, Oct. 2017.

Kaplitt et al., "Safety and tolerability of gene therapy with an adeno-associated virus (AAV) borne GAD gene for Parkinson's disease: an open label, phase I trial," Lancet, vol. 369(9579):2097-105, Jun. 2007.

Kay et al., "Evidence for gene transfer and expression of factor IX in haemophilia B patients treated with an AAV vector," Nat Genet., vol. 24(3):257-61, Mar. 2000.

Tardieu et al., "Intracerebral administration of adeno-associated viral vector serotype rh. 10 carrying human SGSH and SUMF1 cDNAs in children with mucopolysaccharidosis type IIIA disease: results of a phase I/II trial," Hum Gene Ther., vol. 25(6):506-16, Jun. 2014.

Vite et al., "Effective gene therapy for an inherited CNS disease in a large animal model," Ann Neurol., vol. 57(3):355-64, Mar. 2005.

Zanta-Boussif et al., "Validation of a mutated PRE sequence allowing high and sustained transgene expression while abrogating WHV-X protein synthesis: application to the gene therapy of WAS," Gene Therapy, vol. 16: 605-619, May 2009.

Zhang et al., Adenovirus-adeno-associated virus hybrid for large-scale recombinant adeno-associated virus production, Human Gene Therapy 20:922-929, Sep. 2009.

Abeti et al., "Targeting lipid peroxidation and mitochondrial imbalance in Friedreich's ataxia," Pharmacological Research, vol. 99:344-350, Sep. 2015.

Al-Zaidy et al., "Health outcomes in spinal muscular atrophy type 1 following AVXS-101 gene replacement therapy," Pediatr Pulmonol. vol. 54(2):179-185, Feb. 2019.

Audentes, "Audentes announces continuing positive data from first dose cohort of ASPIRO, a Phase 1/2 clinical trial of AT132 in patients with X-linked myotubular myopathy," May 2018, retrieved on Aug. 15, 2023 from https://www.biospace.com/article/releases/audentes-therapeutics.

Bartus et al., "Parkinson's disease gene therapy: Success by design meets failure by efficacy," Mol Ther., vol. 22(3):487-497, Mar. 2014.

Belbellaa et al., "High Levels of Frataxin Overexpression Lead to Mitochondrial and Cardiac Toxicity in Mouse Models," Mol Ther Methods Clin Dev., vol. 19:120-138, Sep. 2020.

Bell et al., "Analysis of tumors arising in male B6C3F1 mice with and without AAV vector delivery to liver," Mol Ther., vol. 14(1):34-44, Jul. 2006.

Bell et al., "No evidence for tumorigenesis of AAV vectors in a large-scale study in mice," Mol Ther., vol. 12(2):299-306, Aug. 2005.

Bevan et al., "Systemic gene delivery in large species for targeting spinal cord, brain, and peripheral tissues for pediatric disorders," Mol Ther., vol. 19(11):1971-80, Nov. 2011.

Bhidayasiri et al., "Late-Onset Friedreich Ataxia: phenotypic analysis, magnetic resonance imaging findings, and review of the literature," Archives of Neurology, vol. 62, Dec. 2005.

Bidichandrani et al., "The GAA triplet-repeat expansion in friedreich ataxia interferes with transcription and may be associated with an unusual DNA structure," American Journal of Human Genetics, vol. 62:111-121, Jan. 1998.

Bryant et al., "Lessons learned from the clinical development and market authorization of Glybera," Hum Gene Ther Clin Dev., vol. 24(2):55-64, Jun. 2013.

Burk, "Friedreich Ataxia: Current status and future prospects," Cerebellum and Ataxias, vol. 4:1-9, Apr. 2017.

Calcedo et al., "Worldwide epidemiology of neutralizing antibodies to adeno-associated viruses," J Infect Dis., vol. 199(3):381-90, Feb. 2009.

Campuzano et al., "Frataxin is reduced in Friedreich ataxia patients and is associated with mitochondrial membranes," Human Molecular Genetics, vol. 6:1771-1780, Oct. 1997.

Campuzano et al., "Friedreich's ataxia: autosomal recessive disease caused by an intronic GAA triplet repeat expansion," Science, vol. 271(5254):1423-7, Mar. 1996.

Castle et al., "Long-distance axonal transport of AAV9 is driven by dynein and kinesin-2 and is trafficked in a highly motile Rab7-positive compartment," Mol Ther., vol. 22(3):554-566, Mar. 2014.

(56)            References Cited

OTHER PUBLICATIONS

Chandler et al., "Vector design influences hepatic genotoxicity after adeno-associated virus gene therapy," J Clin Invest., vol. 125(2):870-80, Feb. 2015.

Chutake et al., "Reversal of epigenetic promoter silencing in Friedreich ataxia by a class I histone deacetylase inhibitor," Nucleic Acids Research, vol. 44:5095-5104, Jun. 2016.

Ciesielska et al., "Cerebral infusion of AAV9 vector-encoding non-self proteins can elicit cell-mediated immune responses," Mol Ther., vol. 21(1):158-66, Jan. 2013.

Colle et al., "Efficient intracerebral delivery of AAV5 vector encoding human ARSA in non-human primate," Hum Mol Genet., vol. 19(1):147-58, Jan. 2010.

Condo et al., "A pool of extramitochondrial frataxin that promotes cell survival," Journal of Biological Chemistry, vol. 281:16750-16756, Jun. 2006.

Cook et al., "Friedreich's ataxia: Clinical features, pathogenesis and management," British Medical Bulletin, vol. 124:19-30, Dec. 2017.

Corben et al., "Consensus clinical management guidelines for Friedreich ataxia," Orphanet Journal of Rare Diseases, vol. 9:1-12, Nov. 2014.

Dabbous et al., "Survival, Motor Function, and Motor Milestones: Comparison of AVXS-101 Relative to Nusinersen for the Treatment of Infants with Spinal Muscular Atrophy Type 1," Adv Ther., vol. 36(5):1164-1176, May 2019.

De Michele et al., "Late onset Friedreich's disease: Clinical features and mapping of mutation to the FRDA locus," Journal of Neurology, Neurosurgery and Psychiatry, vol. 57:977-979, Aug. 1994.

Delatycki, et al., "Clinical Features of Friedreich Ataxia," Journal of Child Neurology, vol. 27:1133-1137, Sep. 2012.

Delatycki et al., "Friedreich ataxia—pathogenesis and implications for therapies," Neurobiology of Disease, vol. 132:104606, Dec. 2019.

Delatycki et al., "Friedreich ataxia: An overview," Journal of Medical Genetics, vol. 37:1-8, Jan. 2000.

Deutsch et al., "A Rapid, Noninvasive Immunoassay for Frataxin: Utility in Assessment of Friedreich Ataxia," Mol Genet Metab., vol. 101(2-3):238-45, Oct. 2010.

Durr et al., "Clinical and genetic abnormalities in patients with Friedreich's ataxia," New England Journal of Medicine, vol. 335:1169-1175, Oct. 1996.

Ellinwood et al., "Safe, efficient, and reproducible gene therapy of the brain in the dog models of Sanfilippo and Hurler syndromes," Mol Ther., vol. 19(2):251-9, Feb. 2011.

Fahey et al., "How Is Disease Progress in Friedreich's Ataxia Best Measured? A Study of Four Rating Scales," J Neurol Neurosurg Psychiatry, vol. 78(4):411-3, Apr. 2007.

Ferla et al., "Non-clinical safety and efficacy of an AAV2/8 vector administered intravenously for treatment of Mucopolysaccharidosis Type VI," Mol Ther Methods Clin Dev., vol. 6:143-158, Jul. 2017.

Filla et al., "The relationship between trinucleotide (GAA) repeat length and clinical features in Friedreich ataxia," Am J Hum Genet., vol. 59(3):554-60, Sep. 1996.

Fisher et al., "Transduction with recombinant adeno-associated virus for gene therapy is limited by leading-strand synthesis," J. Virol., 70:520 532, Jan. 1996.

Foury et al., "Acidic residues of yeast frataxin have an essential role in Fe—S cluster assembly," EMBO Reports, vol. 8:194-199, Feb. 2007.

Foust et al., "Intravascular AAV9 preferentially targets neonatal neurons and adult astrocytes," Nat Biotechnol., vol. 27(1):59-65, Jan. 2009.

Friedman et al., "Measuring the Rate of Progression in Friedreich Ataxia: Implications for Clinical Trial Design," Mov Disord., vol. 25(4):426-32, Mar. 2010.

Gao et al., "Clades of adeno-associated viruses are widely disseminated in human tissues," J Virol., vol. 78(12):6381-8, Jun. 2004.

Gao et al., "Adeno-associated viruses undergo substantial evolution in primates during natural infections," Proc. Natl. Acad. Sci. U.S.A., vol. 100(10):6081-6086, May 2003.

Gili-Farina et al., "Recombinant AAV integration is not associated with hepatic genotoxicity in nonhuman primates and patients," Mol Ther., vol. 24(6):1100-1105, Jun. 2016.

Godel et al., "Human dorsal-root-ganglion perfusion measured in-vivo by MRI," Neuroimage, vol. 141:81-87, Nov. 2016.

Gombash et al., "Systemic gene delivery transduces the enteric nervous system of guinea pigs and cynomolgus macaques," Gene Ther., vol. 24(10):640-648, Oct. 2017.

Gray et al., "Global CNS gene delivery and evasion of anti-AAV-neutralizing antibodies by intrathecal AAV administration in non-human primates," Gene Ther., vol. 20(4):450-9, Apr. 2013.

Gray et al., "Preclinical differences of intravascular AAV9 delivery to neurons and glia: a comparative study of adult mice and nonhuman primates," Mol Ther., vol. 19(6):1058-69, Jun. 2011.

Greig et al., "Non-clinical study examining AAV8.TBG.hLDLR vector-associated toxicity in chow-fed wild-type and LDLR(+/−) Rhesus macaques," Hum Gene Ther Clin Dev., vol. 28(1):39-50, Mar. 2017.

Gurda et al., "Evaluation of AAV-mediated gene therapy for central nervous system disease in canine Mucopolysaccharidosis VII," Mol Ther., vol. 24(2):206-216, Feb. 2016.

Hart et al., "Antioxidant treatment of patients with Friedreich ataxia: Four-year follow-up," Archives of Neurology, vol. 62:621-626, Apr. 2005.

Haurigot et al., "Whole body correction of mucopolysaccharidosis IIIA by intracerebrospinal fluid gene therapy," J Clin Invest., vol. 123(8):3254-3271, Aug. 2013.

Hausse et al., "Idebenone and reduced cardiac hypertrophy in Friedreich's ataxia," Heart, vol. 87:346-349, Apr. 2002.

Hewer et al., "Study of Fatal Cases of Friedreich's Ataxia," Brit. Med. J., vol. 3:649-652, Sep. 1968.

Hinderer et al., "Evaluation of intrathecal routes of administration for adeno-associated viral vectors in large animals," Hum Gene Ther., vol. 29(1):15-24, Jan. 2018.

Hinderer et al., "Widespread gene transfer in the central nervous system of cynomolgus macaques following delivery of AAV9 into the cisterna magna," Mol Ther Methods Clin Dev., vol. 1:14051, Dec. 2014.

Hordeaux et al., "Toxicology study of intra-cisterna magna Adeno-Associated Virus 9 expressing human alpha-L-iduronidase in Rhesus macaques," Mol Ther Methods Clin Dev., vol. 10:79-88, Jul. 2018.

Huynen et al., "The phylogenetic distribution of frataxin indicates a role in iron-sulfur cluster protein assembly," Hum Mol Genet., vol. 10(21):2463-8, Oct. 2001.

Koeppen et al., "Dorsal root ganglia in Friedreich ataxia: satellite cell proliferation and inflammation," Acta neuropathologica communications, vol. 4:46, May 2016.

Koeppen et al., "The pathogenesis of cardiomyopathy in Friedreich ataxia," PLoS One, vol. 10:1-16, Mar. 2015.

Koeppen, "Friedreich's ataxia: pathology, pathogenesis, and molecular genetics," J Neurol Sci., vol. 303(1-2):1-12, Apr. 2011.

Koeppen, "Friedreich ataxia: neuropathology revised," J Neuropathol Exp Neurol., vol. 72(2):78-90, Feb. 2013.

Li et al., "Adeno-associated virus capsid antigen presentation is dependent on endosomal escape," J Clin Invest., vol. 123(3):1390-401, Mar. 2013.

Lock et al., "Absolute determination of single-stranded and self-complementary adeno-associated viral vector genome titers by droplet digital PCR," Hum Gene Ther Methods, vol. 25(2):115-25, Feb. 2014.

Lock et al., "Rapid, Simple, and Versatile Manufacturing of Recombinant Adeno-Associated Viral Vectors at Scale," Human Gene Therapy, vol. 21:1259-1271, Oct. 2010.

Lodi et al., "Cardiac energetics are abnormal in Friedreich ataxia patients in the absence of cardiac dysfunction and hypertrophy: an in vivo 31P magnetic resonance spectroscopy study," Cardiovasc Res., vol. 52(1):111-9, Oct. 2001.

Lowes et al., "Impact of Age and Motor Function in a Phase 1/2A Study of Infants With SMA Type 1 Receiving Single-Dose Gene Replacement Therapy," Pediatr Neurol., vol. 98:39-45, Sep. 2019.

(56) References Cited

OTHER PUBLICATIONS

Lynch et al., "A phase 3, double-blind, placebo-controlled trial of idebenone in Friedreich Ataxia," Archives of Neurology, vol. 67:941-947, Aug. 2010.

Lynch et al., "Randomized, double-blind, placebo-controlled study of interferon-γ 1b in Friedreich Ataxia," Ann Clin Transl Neurol., vol. 6:546-553, Feb. 2019.

Lynch et al., "Safety, pharmacodynamics, and potential benefit of omaveloxolone in Friedreich ataxia," Ann Clin Transl Neurol., vol. 6:15-26, Nov. 2018 (epub Jan. 2019).

Malani et al., "Assessing the potential for AAV vector genotoxicity in a murine model," Blood, vol. 117(12):3311-9, Mar. 2011.

Martelli et al., "Frataxin is essential for extramitochondrial Fe—S cluster proteins in mammalian tissues," Human Molecular Genetics, vol. 16:2651-2658, Nov. 2007.

McCarty et al., "Integration of adeno-associated virus (AAV) and recombinant AAV vectors," Annu Rev Genet., vol. 38:819-45, Aug. 2004.

Medscape, "Cerebrospinal Fluid Analysis," updated Jun. 16, 2022, accessed Aug. 15, 2023 at emedicine.medscape.com/article/2093316-overview.

Melnick et al., "Association of 20 milli-micron particles with adenoviruses," J Bacteriol., vol. 90(1):271-4, Jul. 1965.

Mendell et al., "AVXS-101 Phase 1 Gene Therapy Clinical Trial in SMA Type 1: Event Free Survival and Achievement of developmental milestones (CT.003)," Neurology, vol. 88(16 Supplement), Apr. 2017.

Mendell et al., "Single-dose gene-replacement therapy for spinal muscular atrophy," N Engl J Med., vol. 377(18):1713-1722, Nov. 2017.

Miller, "Glybera and the future of gene therapy in the European Union," Nat Rev Drug Discov., vol. 11(5):419, May 2012.

Miranda et al., "Frataxin overexpressing mice," FEBS letters, vol. 572:281-288, Aug. 2004.

Mittermyer et al., "Long-term evaluation of a Phase 1 study of AADC gene therapy for Parkinson's disease," Hum Gene Ther., vol. 23(4):377-81, Apr. 2012.

Myers et al., "Antioxidant use in Friedreich ataxia," Journal of the neurological sciences, vol. 267:174-6, Apr. 2008.

Nathwani et al., "Adenovirus-associated virus vector-mediated gene transfer in hemophilia B," N Engl J Med, vol. 365(25):2357-65, Dec. 2011.

Pandolfo et al., "Deferiprone for the treatment of Friedreich's ataxia," Journal of Neurochemistry, vol. 126:142-146, Aug. 2013.

Parkinson et al., "Clinical features of Friedreich's ataxia: Classical and atypical phenotypes," Journal of Neurochemistry, vol. 126:103-117, Aug. 2013.

Patel et al., "Progression of Friedreich Ataxia: Quantitative Characterization over 5 Years," Ann Clin Transl Neurol., vol. 3(9):684-94, Jul. 2016.

Payne et al., "Cardiomyopathy in Friedreich Ataxia," Journal of Child Neurology, vol. 27:1179-1186, Sep. 2012.

Penaud-Budloo et al., "Adeno-associated virus vector genomes persist as episomal chromatin in primate muscle," J Virol., vol. 82(16):7875-85, Aug. 2008.

Peverill et al., "Left Ventricular Structural and Functional Changes in Friedreich Ataxia—Relationship with Body Size, Sex, Age and Genetic Severity," PLoS One, vol. 14(11):e0225147, Nov. 2019.

Pianese et al., "Real time PCR quantification of frataxin mRNA in the peripheral blood leucocytes of Friedreich ataxia patients and carriers," J Neurol Neurosurg Psychiatry, vol. 75(7):1061-3, Jul. 2004.

Piguet et al., "Rapid and complete Reversal of Sensory Ataxia by Gene Therapy in a novel Model of Freidrich Ataxia," Mol. Ther., vol. 26(8):p. 1940-1952, Aug. 2018 (ePub May 2018).

Pousset et al., "A 22-year follow-up study of long-term cardiac outcome and predictors of survival in Friedreich ataxia," JAMA Neurol. vol. 72:1334-1341, Nov. 2015.

Puccio et al., "Recent advances in the molecular pathogenesis of Friedreich ataxia," Hum Mol Genet., vol. 9(6):887-92, Apr. 2000.

Rangarajan et al., "AAV5-Factor VIII gene transfer in severe hemophilia A," N Engl J Med., vol. 377(26):2519-2530, Dec. 2017.

Rosas et al., "Patterns of scAAV vector insertion associated with oncogenic events in a mouse model for genotoxicity," Mol Ther., vol. 20(11):2098-2110, Nov. 2012.

Rummey et al., "Predictors of Loss of Ambulation in Friedreich's Ataxia," EClinicalMedicine. 18:100213, Jan. 2020a.

Rummey et al., "Psychometric Properties of the Friedreich Ataxia Rating Scale," Neurol Genet., vol. 5(6):371., Oct. 2019.

Rummey et al., "Test-Retest Reliability of the Friedreich's Ataxia Rating Scale," Ann Clin Transl Neurol., vol. 7(9):1708-1712, Sep. 2020b.

Samaranch et al., "Adeno-associated virus serotype 9 transduction in the central nervous system of nonhuman primates," Hum Gene Ther., vol. 23(4):382-9, Apr. 2012.

Samaranch et al., "Strong cortical and spinal cord transduction after AAV7 and AAV9 delivery into the cerebrospinal fluid of nonhuman primates," Hum Gene Ther., vol. 24(5):526-32, May 2013.

Schadt et al., "Cross-Sectional Analysis of Electrocardiograms in a Large Heterogeneous Cohort of Friedreich Ataxia Subjects," J Child Neurol., vol. 27(9):1187-92, Sep. 2012.

Schmucker et al., "Understanding the molecular mechanisms of friedreich's ataxia to develop therapeutic approaches," Human Molecular Genetics, vol. 19:103-110, Apr. 2010.

Schuster et al., "Biodistribution of adeno-associated virus serotype 9 (AAV9) vector after intrathecal and intravenous delivery in mouse," Front Neuroanat., vol. 8:42, Jun. 2014.

Seznec et al., "Friedreich ataxia: The oxidative stress paradox," Human Molecular Genetics, vol. 14:463-474, Feb. 2005.

Sommer et al., "Quantification of adeno-associated virus particles and empty capsids by optical density measurement," Molec. Ther., vol. 7:122-128, Jan. 2003.

Rai et al., "HDAC inihibitors correct frataxin deficiency in a Friedreich ataxia mouse model," PLoS One, vol. 3, Apr. 2008.

Spark. "European Commission approves Spark Therapeutics' Luxturna® (voretigene neparvovec), a one-time gene therapy for inherited retinal disease caused by confirmed biallelic RPE65 mutations," published Nov. 23, 2018, retrieved on Aug. 16, 2023 at https://www.globenewswire.com.

Thompson et al, "A comprehensive comparison of multiple sequence alignments," Nucl. Acids. Res., vol. 27(13):2682-2690, Jul. 1999.

Tomassini et al., "Interferon gamma upregulates frataxin and corrects the functional deficits in a Friedreich ataxia model," Human Molecular Genetics, vol. 21:2855-2861, Jul. 2012.

Tsirilos et al., "Scoliosis in patients with Friedreich's ataxia," Journal of Bone and Joint Surgery—Series B, vol. 94 B:684-689, May 2012.

Vankan, "Prevalence gradients of Friedreich's ataxia and R1b haplotype in Europe co-localize, suggesting a common Palaeolithic origin in the Franco-Cantabrian ice age refuge," J Neurochem., vol. 126 Suppl 1:11-20, Aug. 2013.

Vyas et al., "A TAT-frataxin fusion protein increases lifespan and cardiac function in a conditional Friedreich's ataxia mouse model," Human Molecular Genetics, vol. 21:1230-1247, Mar. 2012.

Wallace et al., "Molecular genetic testing for hereditary ataxia: What every neurologist should know," Neurology: Clinical Practice, vol. 8:27-32, Feb. 2018.

Weidemann et al., "Cardiomyopathy of Friedreich ataxia," Journal of Neurochemistry, vol. 126:88-93, Aug. 2013.

Weidemann et al., "The Heart in Friedreich Ataxia: Definition of Cardiomyopathy, Disease Severity, and Correlation with Neurological Symptoms," Circulation, vol. 125(13):1626-34, Apr. 2012.

Willis et al., "Lateral-Flow Immunoassay for the Frataxin Protein in Friedreich's Ataxia Patients and Carriers," Mol Genet Metab., vol. 94(4):491-7, Aug. 2008.

Wobus et al., "Monoclonal antibodies against the adeno-associated virus type 2 (AAV-2) capsid: epitope mapping and identification of capsid domains involved in AAV-2-cell interaction and neutralization of AAV-2 infection," J. Virol., vol. 74:9281-9293, Oct. 2000.

Yoon et al., "Frataxin-mediated iron delivery to ferrochelatase in the final step of heme biosynthesis," J Biol Chem., vol. 27(25):25943-6, Jun. 2004.

U.S. Appl. No. 62/266,357, filed Dec. 11, 2015.

(56)                    References Cited

OTHER PUBLICATIONS

U.S. Appl. No. 62/322,071, filed Apr. 13, 2016.
U.S. Appl. No. 62/950,834, filed Dec. 19, 2019.
U.S. Appl. No. 63/023,593, filed May 12, 2020.
U.S. Appl. No. 63/038,488, filed Jun. 12, 2020.
U.S. Appl. No. 63/040,381, filed Jun. 17, 2020.
U.S. Appl. No. 63/043,562, filed Jun. 24, 2020.
U.S. Appl. No. 63/065,616, filed Aug. 14, 2020.
U.S. Appl. No. 63/079,299, filed Jun. 24, 2020.
U.S. Appl. No. 63/109,734, filed Nov. 4, 2020.
International Search Report and Written Opinion, issued on International Patent Application No. PCT/US2020/066167, dated Mar. 25, 2021.
International Search Report and Written Opinion issued on International Patent Application No. PCT/US2022/012003, dated Apr. 15, 2022.
Perdomini et al., "Prevention and reversal of severe mitochondrial cardiomyopathy by gene therapy in a mouse model of Friedreich's Ataxia," Nature Medicine, Apr. 2014, vol. 20(5):542-547.
Agessandro et al., "Milestones in Friedreich ataxia: more than a century and still learning," Neurogenetics, Feb. 2015, vol. 16(3):151-160.
Extended European Search Report issued on related European Patent Application No. 22737299.2, dated Feb. 13, 2025, pp. 1-10.
Acquaviva et al., "Recombinant human erythropoietin increases frataxin protein expression without increasing mRNA expression," Cerebellum, vol. 7:360-365, Jun. 2008.
Babcock et al., "Regulation of mitochondrial iron accumulation by Yfh1p, a putative homolog of frataxin," Science, vol. 276:1709-1712, Jun. 1997.
Berciano et al., "Very late-onset Friedreich's ataxia with minimal GAA1 expansion mimicking multiple system atrophy of cerebellar type," Movement Disorders, vol. 20:1643-1645, Dec. 2005.
Boesch et al., "Neurological effects of recombinant human erythropoietin in Friedreich's ataxia: a clinical pilot trial," Mov Disord., vol. 23(13):1940-4, Oct. 2008.
Boesch et al., "Safety and tolerability of carbamylated erythropoietin in Friedreich's ataxia," Movement Disorders, vol. 29:935-939, Jun. 2014.
Bulteau et al., "Frataxin acts as an iron chaperone protein to modulate mitochondrial aconitase activity," Science, vol. 305(5681):242-5, Jul. 2004.
Cocozza et al., "Friedreich's ataxia: autosomal recessive disease caused by an intronic GAA triplet repeat expansion," Science vol. 271:1423, Mar. 1996.
Cossee et al., "Friedreich's ataxia: point mutations and clinical presentation of compound heterozygotes," Ann Neurol., vol. 45(2):200-6, Feb. 1999.
Delatycki et al., "Direct evidence that mitochondrial iron accumulation occurs in Friedreich ataxia," Ann Neurol., vol. 45(5):673-5, May 1999.
Deoni et al., "Visualization of the deep cerebellar nuclei using quantitative T1 and rho magnetic resonance imaging at 3 Tesla," Neuroimage, vol. 37(4):1260-6, Oct. 2007.
Diedrichsen et al., "Imaging the deep cerebellar nuclei: a probabilistic atlas and normalization procedure," Neuroimage, vol. 54(3):1786-94, Feb. 2011.
Fearon et al., "Very-late-onset Friedreich's ataxia: Diagnosis in a kindred with late-onset cerebellar ataxia," Practical Neurology, vol. 20:55-58, Feb. 2020.
Filla et al., "Genetic data and natural history of Friedreich's disease: a study of 80 Italian patients," J Neurol., vol. 237(6):345-51, Oct. 1990.
Folker et al., "Dysarthria in Friedreich's Ataxia: A Perceptual Analysis," Folia Phoniatr Logop. vol. 62(3):97-103, Apr. 2010.
Gordon, "Friedreich's ataxia and iron metabolism," Brain and Development, vol. 22:465-468, Dec. 2000.
Harding, "Friedreich's ataxia: a clinical and genetic study of 90 families with an analysis of early diagnostic criteria and intrafamilial clustering of clinical features," Brain, vol. 104:589-620, Sep. 1981.

Kosutic et al., "High-dose beta-blocker hypertrophic cardiomyopathy therapy in a patient with Friedreich ataxia," Pediatric Cardiology, vol. 26:727-730, Sep. 2005.
Koutnikova et al., "Studies of human, mouse and yeast homologues indicate a mitochondrial function for frataxin," Nat Genet., vol. 16(4):345-51, Aug. 1997.
Lagedrost et al., "Idebenone in Friedreich ataxia cardiomyopathy-results from a 6-month phase III study (IONIA)," Am Heart J., vol. 161(3):639-645, Mar. 2011.
Lodi et al., "Antioxidant treatment improves in vivo cardiac and skeletal muscle bioenergetics in patients with Friedreich's ataxia," Ann Neurol., vol. 49(5):590-596, May 2001.
Lynch et al., "Friedreich ataxia: effects of genetic understanding on clinical evaluation and therapy," Archives of Neurology, vol. 59:743-7, May 2002.
Lynch et al., "Management and therapy for cardiomyopathy in Friedreich's ataxia," Expert Rev Cardiovasc Ther., vol. 10(6):767-77, Jun. 2012.
Marcotulli et al., "GIFT-1, a phase IIa clinical trial to test the safety and efficacy of IFNγ administration in FRDA patients," Neurological Sciences, vol. 37:361-364, Mar. 2016.
Mariotti et al., "Erythropoietin in Friedreich ataxia: no effect on frataxin in a randomized controlled trial," Mov Disord., vol. 27(3):446-9, Mar. 2012.
Milne et al., "Sensitivity of Spatiotemporal Gait Parameters in Measuring Disease Severity in Friedreich Ataxia," Cerebellum, vol. 13(6):677-88, Dec. 2014.
Nachbauer et al., "Effects of erythropoietin on frataxin levels and mitochondrial function in Friedreich ataxia—A dose-response trial," Cerebellum, vol. 10:763-769, Dec. 2011.
Nguyen et al., "The Assessment of Upper Limb Functionality in Friedreich Ataxia Via Self-Feeding Activity," IEEE Trans Neural Syst Rehabil Eng., vol. 28(4):924-933, Apr. 2020.
Ragno et al., "Broadened Friedreich's ataxia phenotype after gene cloning. Minimal GAA expansion causes late-onset spastic ataxia," Neurology, vol. 49(6):1617-20, Dec. 1997.
Reetz et al., "Biological and clinical characteristics of the European Friedreich's Ataxia Consortium for Translational Studies (EFACTS) cohort: A cross-sectional analysis of baseline data," The Lancet Neurology, vol. 14:174-182, Feb. 2015.
Reetz et al., "Progression characteristics of the European Friedreich's Ataxia Consortium for Translational Studies (EFACTS): a 2 year cohort study," The Lancet Neurology, vol. 15:1346-1354, Dec. 2016.
Regner et al., "Analysis of echocardiograms in a large heterogeneous cohort of patients with Friedreich ataxia," American Journal of Cardiology, vol. 109:401-405, Feb. 2012.
Rotig et al., "Aconitase and mitochondrial iron-sulphur protein deficiency in Friedreich ataxia," Nature Genetics, vol. 17:215-7, Oct. 1997.
Rustin et al., "Effect of idebenone on cardiomyopathy in Friedreich's ataxia: a preliminary study," Lancet, vol. 354(9177):477-9, Aug. 1999.
Sacca et al., "Epoetin alfa increases frataxin production in Friedreich's ataxia without affecting hematocrit," Mov Disord., vol. 26(4):739-42, Mar. 2011.
Schulz et al., "Diagnosis and treatment of Friedreich ataxia: A European perspective," Nature Reviews Neurology, vol. 5:222-234, Apr. 2009.
Schulz et al., "Oxidative stress in patients with Friedreich ataxia," Neurology, vol. 55(11):1719-21, Dec. 2000.
Seyer et al., "Open-label pilot study of interferon gamma-1b in Friedreich ataxia," Acta Neurologica Scandinavica, vol. 132:7-15, Jul. 2015.
St John Sutton et al., "Longitudinal Strain in Friedreich Ataxia: A Potential Marker for Early Left Ventricular Dysfunction," Echocardiography, vol. 31(1):50-7, Jul. 2013.
Sturm et al., "Recombinant human erythropoietin: effects on frataxin expression in vitro," Eur J Clin Invest., vol. 35(11):711-7, Nov. 2005.
Subramony et al., "Measuring Friedreich Ataxia: Interrater Reliability of a Neurologic Rating Scale," Neurology, vol. 64(7):1261-2, Apr. 2005.

(56)     References Cited

OTHER PUBLICATIONS

Suno et al., "Inhibition of lipid peroxidation by a novel compound (CV-2619) in brain mitochondria and mode of action of the inhibition," Biochem Biophys Res Commun., vol. 125(3):1046-52, Dec. 1984.

Tsot et al., "Mortality in Friedreich ataxia," J Neurol Sci., vol. 307(1-2):46-49, Aug. 2011.

Velasco-Sanchez et al., "Combined therapy with idebenone and deferiprone in patients with Friedreich's ataxia," Cerebellum, vol. 10:1-8, Mar. 2011.

Vogel et al., "Clinical Assessment of Dysphagia in Neurodegeneration (Cadn): Development, Validity and Reliability of a Bedside Tool for Dysphagia Assessment," J Neurol., vol. 264(6): 1107-1117, Jun. 2017.

Yoon et al., "Iron-sulfur cluster biosynthesis. Characterization of frataxin as an iron donor for assembly of [2Fe—2S] clusters in ISU-type proteins," Journal of the American Chemical Society, vol. 125:6078-6084, May 2003.

FIG 1A

```
HUMAN_FRATAXIN            ATGTGGACTCTCGGGGCGGCGGCGCGCAGTAGCCGGCCTCCTGGCGTCACCCAGCCCAGCCCAG   60
HUMAN_FXN_CODON-OPTIMIZED ATGTGGACACTTGGCCCGGCCGCAGAGCTGTTGCTGGCCTGCTTGCTTCTCCCATCTCCGGCTCAA   60
                          * ****** *  ***  *  *  * ** * ** *  ** *  ** * **  ** ***

HUMAN_FRATAXIN            GCCCAGACCCTCACCCGGGTCCCGGGCCGGCAGAGTTGGCCCCACTCTCGCGGCGGCGGT  120
HUMAN_FXN_CODON-OPTIMIZED GCCCAGACACTGACCAGAGTGCCTAGACCTGGCCCTGAACTGGCCCCTCTGTGTGGCAGAAGA  120
                          ******** *  ***  * ** * ***  ** * ***  ****  ** * ***  *

HUMAN_FRATAXIN            GGCCTGCGCACCGACATCGATGCGGACCTGCACGGCCCCGCGGCCCGGCAAGTTCGAACCAACGT  180
HUMAN_FXN_CODON-OPTIMIZED GGCCTGAGAACCGACCTGGGACACCCACATGCACGCCCACCTAGAAGGGCCAGCAGCAATCAGCGG  180
                          ****** * ****** *  *  *****  ** ** **  *  *  ** *  ** * **

HUMAN_FRATAXIN            GGCCTCAACCAGCAGATTGGAATGTCAAAAAGCAGAGTGTCTATTGATGAATTTGAGGAAA  240
HUMAN_FXN_CODON-OPTIMIZED GGCCTGAATCAGATCTGGAACGTGAAGAAACAGAGCGTGTACCTGATGAACCTGAGAGAAAG  240
                          ***** ** *** *  ***** ** ** *** ***** ** ** ***** * *** *

HUMAN_FRATAXIN            TCTGGAACTTTGGGCCACCCCAGGCTCTCCTAGATGAGACCACCTATGAAAGACTAGCAGAG  300
HUMAN_FXN_CODON-OPTIMIZED AGCGGCACCCCTGGGACACCCCTGGAAGCCTGGACAGCACCTACGAGAGACTACGGCCGGAG  300
                          * **  ** *  ***  *****  ** *  * ***  ** ***** * ****  * ***

HUMAN_FRATAXIN            GAAACGCCTGGACTCTTTAGCACAGAGTTTTGAAGACCTTGCAGACAAGCCCATACACGTTT  360
HUMAN_FXN_CODON-OPTIMIZED GAAACCCCTGGATTCCCTGGCCGAGTTCTTCGAGGACCTGGCCGATAAGCCCTACACCTTC  360
                          ***** ***** ** *  **  * **** *  ** ***** ** *  ***** ** * *

HUMAN_FRATAXIN            GAGGACTATGATGTCTCCTTTGGGAGTGGTGTCTTAAACTGTCAAAACTGGGTGGAGATCTA  420
HUMAN_FXN_CODON-OPTIMIZED GAGGATTACGACGTGTCCTTTGGCAGCGGCGTGCTGACAGTGAAACTGGGCGGCGAGATCTG  420
                          ***** ** ** ** ******** ** ** ** * *  ** ***** ** ** ******

HUMAN_FRATAXIN            GGAACCTATGTGATCAACAAGCAGACGCCAAAACAAGCAAATCTGGCTATCTTCTCCATCC  480
HUMAN_FXN_CODON-OPTIMIZED GGCACCTACGTGATCAACAAGCAGACCCCTAACAAACAGATCTGGCTGAGCAGCCCTAGC  480
                          ** ***** ***************** ** * *** ** * ******  * *** * *
```

FIG 1B

```
HUMAN_FRATAXIN            AGTGGGACCTAAGCGTTATGACTGGGACTGGGAAAAACTGGGTGTACTCCCACGACGGCGTG    540
HUMAN_FXN_CODON-OPTIMIZED AGCGGCGCCCAAGAGAGATACGATTGGACCGGCAAGAACTGGGTGTACAGCCACGACGGCGTG   540
                          ** ** **** ** **** ** ****** *** ****************** ***********

HUMAN_FRATAXIN            TCCCTCCATGAGCTGCTGGCCGCGCAGAGCTCACTAAAGCCTAAAAACCAAACTGGACTTG    600
HUMAN_FXN_CODON-OPTIMIZED TCCCTGCACGAACTGCTGGCTGCCGAACTGACAAGGCCCTGAAAAACAAAGCTGGACCTG    600
                          ***** ** ** ******** ** ** ** *** ** *** ** **** * *** ***** * *

HUMAN_FRATAXIN            TCTTCCTTGGCCTATTCCGGAAAAAGATGCT    630
HUMAN_FXN_CODON-OPTIMIZED TCCAGCCTGGCCTACTCTGGCAAGGATGCC    630
                          ** * ******** ** ** ** ******
``` rAAV, recombinant adeno-associated virus; ddPCR, droplet digital polymerase chain reaction; GC, genome copies; Ph. Eur., European Pharmacopoeia; USP, United States Pharmacopeia.

AEX, anion exchange; ddPCR, droplet digital polymerase chain reaction

COMPOSITIONS FOR TREATING FRIEDREICH'S ATAXIA

CROSS-REFERENCE TO RELATED APPLICATIONS

This is a National Stage Entry under 35 U.S.C. 371 of International Patent Application No. PCT/US2020/066167, filed Dec. 18, 2020, which claims the benefit of U.S. Provisional Application No. 62/950,834, filed Dec. 19, 2019. These applications are incorporated by reference herein in their entirety.

BACKGROUND OF THE INVENTION

Friedreich's ataxia (FRDA) is a rare genetic disorder characterized by progressive neurological symptoms, cardiomyopathy and increased risk of diabetes. Patients typically present in late childhood or early adolescence with ataxia, dysarthria and spasticity [Harding, A. E. Friedreich's ataxia: a clinical and genetic study of 90 families with an analysis of early diagnostic criteria and intrafamilial clustering of clinical features. Brain: a journal of neurology 104, 589-620 (1981)]. Most become wheelchair dependent in the third decade due to worsening ataxia, though lower extremity strength often remains intact [Harding, cited above]. Sensory neuropathy predominately affecting proprioception presents early and shows little progression later in the disease course [Koeppen, A. H. Friedreich's ataxia: pathology, pathogenesis, and molecular genetics. Journal of the neurological sciences 303, 1-12 (2011)]. Most FRDA patients develop a hypertrophic cardiomyopathy which is frequently the cause of death in the fifth or sixth decade. Virtually all FRDA patients exhibit impaired glucose tolerance, and about 10% develop diabetes [Harding, cited above; Koeppen, cited above].

FRDA is caused by recessively inherited mutations in the gene encoding frataxin, a ubiquitous mitochondrial protein involved in iron metabolism. The most common pathogenic allele is a large noncoding trinucleotide repeat expansion in the first intron of the frataxin gene [Cocozza, S., Koenig, M. & Pandolfoll, M. Friedreich's ataxia: autosomal recessive disease caused by an intronic GAA triplet repeat expansion. Science (New York, N.Y.) 271, 1423 (1996)]. The expansion inhibits transcription of the gene, resulting in a 70-80% reduction in frataxin protein [Planese L., et al. Real time PCR quantification of frataxin mRNA in the peripheral blood leucocytes of Friedreich ataxia patients and carriers. Journal of Neurology, Neurosurgery & Psychiatry 75, 1061-1063 (2004)]. Additional loss-of-function mutations have been identified in some FRDA patients, indicating that the repeat expansion causes disease through inhibition of expression rather than a toxic gain-of-function mechanism [Cocozza, cited above]. Residual frataxin protein expression is inversely proportional to repeat length, and patients with longer repeat expansions have earlier symptom onset [Filla, A., et al. The relationship between trinucleotide (GAA) repeat length and clinical features in Friedreich ataxia. American Journal of Human Genetics 59, 554-560 (1996)]. The neurological phenotype of FRDA can be localized to three cell types that are selectively susceptible to frataxin deficiency [Koeppen, cited above; Filla, cited above]. Neurons in the dentate nuclei of the cerebellum demonstrate marked degeneration, which correlates clinically with ataxia, dysmetria and dysarthria. There is also degeneration of upper motor neurons and the corresponding axons in the corticospinal tract, giving rise to spasticity. The sensory neuropathy is caused by death of sensory neurons in the dorsal root ganglia. The central nervous system lesions of FRDA are remarkably specific to these three cell types, with sparing of the rest of the brain and spinal cord in most patients [Koeppen, cited above; Filla, cited above].

Adeno-associated virus (AAV), a member of the Parvovirus family, is a small non-enveloped, icosahedral virus with single-stranded linear DNA (ssDNA) genomes of about 4.7 kilobases (kb) long. The wild-type genome comprises inverted terminal repeats (ITRs) at both ends of the DNA strand, and two open reading frames (ORFs): rep and cap. Rep is composed of four overlapping genes encoding rep proteins required for the AAV life cycle, and cap contains overlapping nucleotide sequences of capsid proteins: VP1, VP2 and VP3, which self-assemble to form a capsid of an icosahedral symmetry.

AAV is assigned to the genus, Dependovirus, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

What is desirable are alternative therapeutics for treatment of patients having conditions associated with an abnormal FXN gene.

SUMMARY OF THE INVENTION

A therapeutic, recombinant (r), replication-defective, adeno-associated virus (AAV) is provided which is useful for treating and/or reducing the symptoms associated with Freidreich's ataxia (FA or FRDA) in human patients in need thereof. A recombinant adeno-associated virus (rAAV) is provided which comprises an AAV capsid and a vector genome comprising an FXN gene having the sequence of SEQ ID NO: 3 or a sequence 95% identical thereto that encodes a human frataxin, and regulatory sequences which direct expression of the FXN gene in targeted human cells. In certain embodiments, the FXN gene encodes for an amino acid sequence of SEQ ID NO: 2 or a sequence at least about 95% identical thereto. In certain embodiments, the vector genome comprises an AAV2 5' inverted terminal repeat (ITR) a CB7 promoter, an intron, the FXN gene, a polyA, and an AAV2 3' ITR. In certain embodiments, the vector genome comprises See, SEQ ID NO: 8, or See, also, SEQ ID NO: 12. In certain embodiments, the vector genome comprises a 5' ITR, nucleotides 198 to 2737 of SEQ ID NO: 8 and a 3' ITR. In the embodiments, the vector genome comprises a 5' ITR, nucleotides 198 to 2736 of SEQ ID NO: 12, and a 3' ITR. In some embodiments, the vector genome comprises at least one, at least two, or at least three tandem repeats of dorsal root ganglion (DRG)-specific miRNA targeted sequences. In certain embodiments, the AAV capsid is selected from AAVrh.91 or AAVhu68. In some embodiments, the AAVhu68 capsid comprise a heterogeneous population of vp1 (aa Ito 736 of SEQ ID NO: 5; encoded by nt 1 to 2211 of SEQ ID NO: 4), vp2 (aa 138 to 736 of SEQ ID NO: 5; encoded by nt 412 to 2211 of SEQ ID NO: 4), and vp3 (aa 203 to 736 of SEQ ID NO: 5; encoded by nt 607 to 2211 SEQ ID NO: 4) proteins.

Also provided herein is a pharmaceutical composition comprising a formulation buffer and a stock of a rAAV.FXN as described herein. In certain embodiments, the formulation buffer comprises an artificial cerebrospinal fluid which comprises of a buffered saline and one or more of sodium, calcium, magnesium, potassium, or mixtures thereof, and a surfactant. In some embodiments, the pharmaceutical composition is at a pH in the range of 7.5 to 7.8, or 6.2 to 7.7, or about 7.

Also provided herein is a regimen comprising dual-route of administration of the rAAV or the pharmaceutical composition wherein such regimen comprising of intravenous administration and intraparenchymal (dentate nucleus) administration to a patient in the need thereof. In some embodiments, intravenous administration and intraparenchymal administration are performed sequentially and within 24-hours of each other. In some embodiments, the regimen comprising intravenous and intrathecal administration of the rAAV or the pharmaceutical composition.

In certain embodiments, the rAAV or the pharmaceutical composition provided herein are useful in treatment of FRDA, wherein the treatment comprises of a dual-route administration, and includes amelioration of FRDA by reducing of cardiac and/or neurological symptoms. In some embodiments, the amelioration of FRDA includes increased average life span, reduction in progression towards neuromuscular decline, improvement in neuromuscular development, reduction in progression towards cardiomyopathy and/or improvement in cardiac symptoms. In certain embodiments, the rAAV or the pharmaceutical composition is suitable for intravenous, intraparenchymal and/or intrathecal administration to a patient in the need thereof.

In certain embodiments, a method or a use of a composition is provided for treating FRDA in a subject with FRDA and/or ameliorating one or more symptoms of FRDA, wherein the method or the use of a composition comprising administering of the rAAV or the pharmaceutical composition provided herein to a subject via intravenous, intraparenchymal, and/or intrathecal delivery In certain embodiments, a method or a use of a composition, comprises dual-route administration including intravenous and intraparenchymal administration, wherein the rAAV or the pharmaceutical composition is administered at a ratio of about 20:1 to about 1:1, preferably about 10:1 (intravenous:intraparenchymal). In certain embodiments, the dual route of administration may be used for delivery in combination with an rAAV.FXN and a second active component for treating FA patients.

Also provided herein is a plasmid comprising an expression cassette which comprises a FXN gene having the sequence of SEQ ID NO: 3 or a sequence 95% identical thereto that encodes human frataxin. In certain embodiments, the FXN gene encodes a frataxin protein having the sequence of SEQ ID NO: 2, or a sequence at least 95% identical thereto. In certain embodiments, the plasmid comprises a vector genome which comprises AAV2 5' ITR, CB7 promoter, an intron, a polyA, and an AAV2 3' ITR. Host cells comprising the plasmids described herein are also provided. In certain embodiments, the vector genome comprises See, SEQ ID NO: 8, or See, also, SEQ ID NO: 12. In certain embodiments, the vector genome comprises a 5' ITR, nucleotides 198 to 2737 of SEQ ID NO: 8 and a 3' ITR. In the embodiments, the vector genome comprises a 5' ITR, nucleotides 198 to 2736 of SEQ ID NO: 12, and a 3' ITR.

The activity of a rAAV.hFXN via intravenous administration has been evaluated in a murine model of FRDA cardiomyopathy. rAAV.hFXN administration increased heart frataxin levels and significantly improved survival.

Studies in nonhuman primates have demonstrated that the rAAV.hFXN can efficiently express frataxin in key cellular targets with an acceptable safety profile. In certain embodiments, rAAV.hFXN may be suitable for combined central and intravenous routes of administration to address the cardiac and neurological features of FRDA.

These and other aspects of the invention are apparent from the following detailed description of the invention.

BRIEF DESCRIPTION OF THE DRAWINGS

FIGS. 1A and 1B provide an alignment of wild-type human frataxin (SEQ ID NO: 1) and an engineered human frataxin coding sequence (Human FXN) (SEQ ID NO: 3). FIG. 1A provides an alignment of nucleic acids 1 to 480 of wild-type and an engineered human frataxin coding sequence. FIG. 1B provides an alignment of nucleic acid 481 to 630 of wild-type and an engineered human frataxin coding sequence. The sequences are about 73% identical as determined using an online BLAST tool (blast.ncbi.nlm.nih-.gov).

FIG. 2A provides a graph of body weight (grams±SEM) of untreated control mice or mice intravenously administered rAAVhu68.hFXN over time (0-20 weeks). At 30 days of age Fxn cKO mice were IV-administered rAAVhu68.hFXN at a dose of $2.0×10^{11}$ GC. Age-matched Fxn cKO mice and Fxn unaffected mice remained untreated and served as controls. Body weights were recorded weekly until human euthanasia criteria were met. Average body weights are presented. Error bars represent the standard error of the mean. Abbreviations: Fxn, frataxin (gene, mouse); GC, genome copies; Fxn cKO, cardiac conditional knockout affected mice (Fxn$^{flox/null}$::Ckmm-Cre); Fxn unaffected mice (Fxn$^{flox/null}$); GC, genome copies; IV, intravenous; SEM, standard error of the mean. The triangles represent Fxn$^{flox/null}$::Ckmm-Cre+ rAAVhu68.hFXN ($2×10^{11}$ genome copies (GC) intravenous (iv) at 5 weeks (n=7). The circles represent results in Fxn$^{flox/null}$::Ckmm-Cre mice (n=7). The squares represent Fxn$^{flox/null}$(n=7). FIG. 2B provides percent survival of untreated control mice or mice intravenously administered rAAVhu68.hFXN over time (0 to 20 weeks). At 30 days of age Fxn cKO mice were IV-administered rAAVhu68.hFXN at a dose of $2.0×10^{11}$ GC. Age-matched Fxn cKO mice and Fxn unaffected control mice remained untreated and served as controls. Survival was monitored. Abbreviations: Fxn, frataxin (gene, mouse); GC, genome copies; Fxn cKO, cardiac conditional knockout affected mice (Fxn$^{flox/null}$:: Ckmm-Cre); Fxn unaffected control mice (Fxn$^{flox/null}$).

FIG. 4A provides the upstream manufacturing process flow diagram. FIG. 4B provides the downstream manufacturing process flow diagram.

DETAILED DESCRIPTION OF THE INVENTION

Figure 2A:
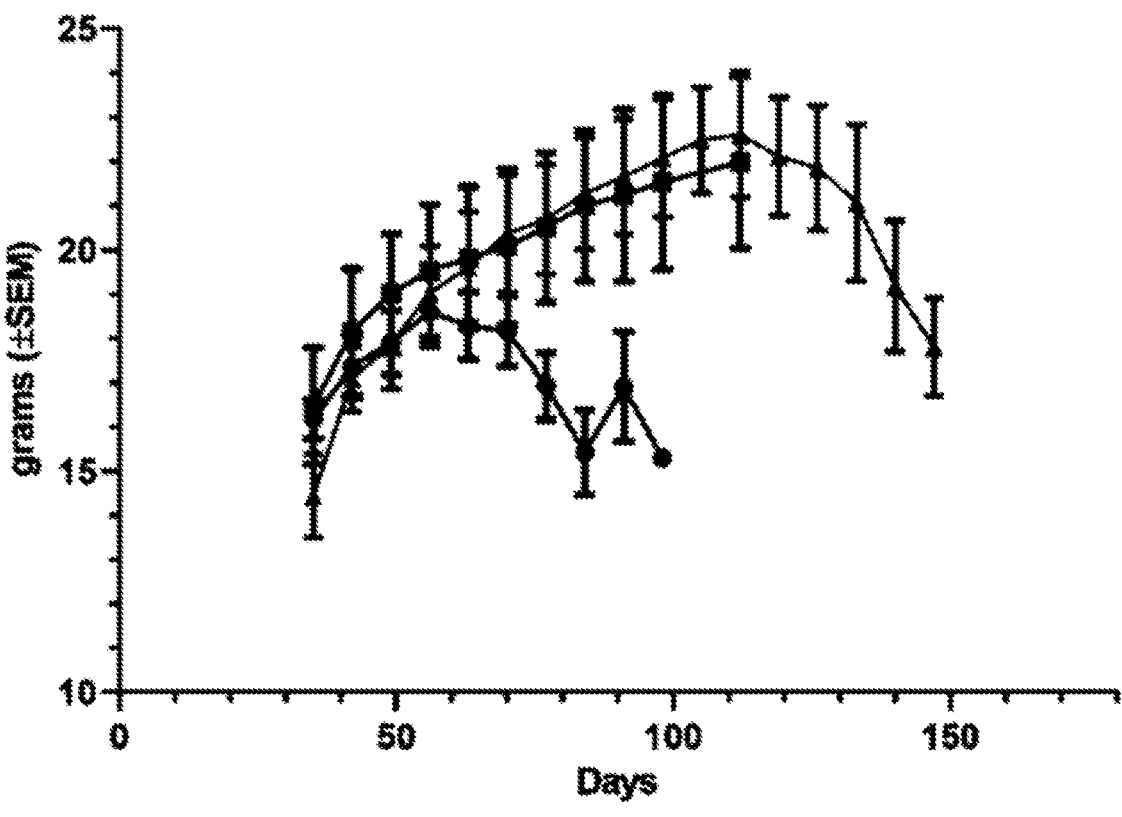
FIGS. 2A and 2B provide the results of a pilot cardiac gene therapy study in a $FXN^{-flox}$; Ckmm-Cre$^{+/-}$ FA mouse model.

Adeno-associated virus (AAV) based compositions and methods for treating Friedreich's ataxia (FRDA or FA) are provided herein. The rAAV is desirably replication-defective and carries a vector genome comprising a hFXN gene encoding human(h) frataxin under the control of regulatory sequences which direct its expression in targeted human cells; this rAAV may be termed as rAAV.hFXN as used herein. In certain embodiments, the rAAV comprises an AAVhu68 capsid. This rAAV is termed herein rAAVhu68.hFXN, but in certain instances the terms rAAVhu68.HFXN vector, rAAVhu68.hFXN, or AAVhu68.hFXN vector are used interchangeable to reference the same embodiment. In certain embodiments, the vector genome is entirely exogenous to the AAVhu68 capsid, as it contains no AAVhu68 genomic sequences. In certain embodiments, a capsid other than the AAVhu68 capsid may be utilized (e.g. AAVrh91). In a further embodiment, the rAAV has a capsid is suitable for delivering a vector genome into the central nervous system (CNS) and/or intravenously. For example, a vector capsid may target the dentate nuclei in the cerebellum, the cerebellum, the brain, or other cells in the CNS. In certain embodiments, the rAAV compositions Additionally, provided are methods, vectors (viral or non-viral vectors, such as plasmids), and cells for use in production (for example, generation and/or purification) of the rAAV. An effective amount of genome copies (GC) of a recombinant AAV (rAAV) having an AAVhu68 capsid and carrying a vector genome encoding a frataxin (FXN) enzyme (rAAVhu68.FXN) is delivered to the patient. Desirably, this rAAVhu68.FXN is formulated with an aqueous buffer. In certain embodiments, the suspension is suitable for intrathecal injection/infusion, intravenous injection/infusion, or intraparenchymal injection/infusion. In certain embodiments, rAAVhu68.FXN is rAAVhu68.hFXN, in which the FAN gene (i.e., frataxin (also termed as FXN protein) is under the control of regulatory sequences. In certain embodiments, a single route of administration is used for targeting cardiac tissue and/or the central nervous system (e.g., dorsal root ganglia). In certain embodiments, two or more routes of delivery are used. In certain embodiments, one route of delivery is intravenous and the second route of delivery is intraparenchymal.

Reduced expression of frataxin (encoded by the FXN gene) is the cause of Friedreich's ataxia, a neurodegenerative disease. FRDA is characterized by ataxia, sensory loss and cardiomyopathy. With reference to SEQ ID NO: 2, the full-length human frataxin protein is 210 amino acids in length. See, e.g., UniProtKB.org/uniprot/Q16595. The human frataxin protein contains an N-terminal transit peptide (e.g, amino acids 1 to 41, or a fragment thereof). Various forms of frataxin have been described and may have biological function, including a frataxin intermediate form (e.g., about amino acid 20 to about amino acid 210, or about amino acid 42 to about amino acid 210). In certain embodiments, the mature frataxin includes about amino acid 81 to about amino acid 210, which may be sufficient to provide frataxin's biological function. However, in certain embodiments, additional forms of frataxin, e.g., about amino acid 56 to about amino acid 210 of SEQ ID NO:2, or about amino acids 78 to about amino acid 210 of SEQ ID NO: 2 may provide the desired frataxin biological function. In certain embodiments, more than one form of frataxin is produced following expression of the FXN gene. In certain embodiments, frataxin may be present as a monomer. In certain embodiments, frataxin may be present as an oligomer.

As used herein, "treating Friedrich's ataxia" means to increase expression levels of the human frataxin protein, or a functional form thereof, to a level which improves one or more symptoms of FRDA and/or which prevents progression of the symptoms in a subject. Such symptoms may include one or more of: neurodegeneration and cardiomyopathy, ataxia (impaired ability to coordinate voluntary movements), dysarthria (slurred speech, progressive), spasticity, weakness (progressive), sensory neuropathy, diabetes, nystagmus, diminished or absent tendon reflexes, Babinski sign, impairment of position and vibratory senses, scoliosis (curvature of the spine), pes *cavus*. and hammer toe. About a third of the people with FRDA develop diabetes mellitus, which usually manifests before adolescence. In some embodiments, onset is between 10 and 15 years and most people are diagnosed before age 25. Late-onset FRDA/very late onset FRDA affect about 15% of FRDA patients. Late-onset FRDA is typically from ages 26 to 39 and very late onset FRDA is typically after 40 years of age. In certain embodiments, treating FRDA includes dual-routes of administration, wherein a composition is administered systemically and to the central nervous system (CNS). In some embodiments, the dual-routes of administration include intravenous (IV) and intraparenchymal (dentate nucleus) (IDN) routes of administration. The dual-routes of administration addresses an unmet need in FRDA patients to stabilize and/or improve the ataxic symptoms of FRDA (CNS) and to prevent cardiac manifestation of FRDA (systemic). Furthermore, the IDN route of administration of a composition addresses neurological manifestations in the dentate nuclei and DRG and treats ataxia, dysmetria, dysarthria along with peripheral neuropathy observed in FRDA patients.

The gene therapy vectors provided herein, i.e., rAAV.FXN (for example, rAAVhu68.FXN), and the compositions comprising the same are useful for treatment of conditions associated with deficiencies in levels of frataxin in a subject. As used herein, a gene therapy vector refers to a rAAV as described herein, which is suitable for use in treating a patient. In certain embodiments, the gene therapy vector or the pharmaceutical composition provided herein is useful for treating FRDA.

In certain embodiments, an "effective amount" of rAAV.FXN (for example, rAAVhu68.hFXN) as provided herein is the amount which achieves amelioration of one or more symptoms associated with FRDA. The rAAV.FXN described herein, and compositions comprising the same, contain a FXN gene (i.e., frataxin coding sequence) which encodes and expresses human frataxin protein (which may be also termed as FXN enzyme), or a functional fragment thereof. In one embodiment, the FXN gene is engineered to have the sequence of SEQ ID NO: 3, or a sequence at least 95% identical thereto. In certain embodiments, the FXN gene encodes a frataxin protein having an amino acid sequence of SEQ ID NO: 2, or a sequence at least 95% identical thereto. As shown in FIG. 1, SEQ ID NO: 3 is less than 80% identical to the wild-type FXN gene, which is reproduced in SEQ ID NO: 1. As used herein, the term "functional frataxin" refers to an enzyme having the amino acid sequence of the full-length native (wild-type) protein (as shown in SEQ ID NO: 2), a variant thereof, a mutant thereof with a conservative amino acid replacement, a fragment thereof, a full-length or a fragment of any combination of the variant and the mutant with a conservative amino acid replacement, which provides at least about 10%, at least about 20%, at least about 30%, at least about 40%, at least about 50%, at least about 60%, at least about 70%, at least about 75%, at least about 80%, at least about 90%, or about the same, or greater than 100% of the biological activity level of a native (wild-type) frataxin.

In certain embodiments, the native leader sequence of the human FXN gene (e.g., amino acids 1 to 41) may be removed in full or in part and replaced with an exogenous leader sequence. In one embodiment, the leader is from human IL2 or a mutated leader. In another embodiment, a human serpinF1 secretion signal is used as a leader peptide.

The term "expression" is used herein in its broadest meaning and comprises the production of RNA and/or protein. With respect to RNA, the term "expression" or "translation" relates in particular to the production of peptides or proteins. Expression may be transient or may be stable.

It is to be noted that the term "a" or "an", refers to one or more, for example, "an enhancer", is understood to represent one or more enhancer(s). As such, the terms "a" (or "an"), "one or more," and "at least one" is used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As described above, the term "about" when used to modify a numerical value means a variation of ±10%, unless otherwise specified.

As described above, the terms "increase" "decrease" "reduce" "ameliorate" "improve" "delay" "earlier" "slow" "cease" or any grammatical variation thereof, or any similar terms indication a change, means a variation of about 5 fold, about 2 fold, about 1 fold, about 90%, about 80%, about 70%, about 60%, about 50%, about 40%, about 30%, about 20%, about 10%, about 5% compared to the corresponding reference (e.g., untreated control, corresponding level of a FA patient or a FA patient at a certain stage or a healthy subject or a healthy human without FA)), unless otherwise specified.

"Patient" or "subject" as used herein refer to a mammalian animal, including a human, a veterinary or farm animal, a domestic animal or pet, and animals normally used for clinical research. In one embodiment, the subject of these methods and compositions is a human. In certain embodiments, the patient has FA.

Unless defined otherwise in this specification, technical and scientific terms used herein have the same meaning as commonly understood by one of ordinary skill in the art and by reference to published texts, which provide one skilled in the art with a general guide to many of the terms used in the present application.

1. rAAV

In certain embodiments, provided herein is a rAAV comprising an AAV capsid and a vector genome packaged therein. The vector genome includes an AAV 5' inverted terminal repeat (ITR), a nucleic acid sequence encoding a FXN gene as described herein, regulatory sequences which directs expression FXN in a target cell, and an AAV 3' ITR. Such rAAV are suitable for use in the treatment of Friedreich's ataxia. The gene therapy vectors provided herein, i.e., rAAV.FXN (for example, rAAVhu68.FXN), and the compositions comprising the same are useful for treatment of conditions associated with deficiencies in levels of frataxin in a subject.

As used herein, a "rAAV.hFXN" refers to a rAAV having a vector genome that includes an hFXN coding sequence. A "rAAVhu68.hGLA" refers to rAAV having an hu68 capsid and a vector genome that includes an hFXN coding sequence.

AAVhu68 varies from another Clade F virus AAV9 by two encoded amino acids at positions 67 and 157 of vp1, based on the numbering of SEQ ID NO: 5. In contrast, the other Clade F AAV (AAV9, hu31, hu31) have an Ala at position 67 and an Ala at position 157. AAVhu68 capsids have a valine (Val or V) at position 157 and a glutamic acid (Glu or E) at position 67, based on the numbering of SEQ ID NO: 5. Another suitable capsid is AAVrh91. See WO 2020/223231, published Nov. 5, 2020, U.S. Patent Application No. 63/065,616, filed Aug. 14, 2020, and U.S. Patent Application Ser. No. 63/109,734, filed Nov. 4, 2020, which are incorporated herein by reference.

As used herein, the term "clade" as it relates to groups of AAV refers to a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, Molecular Evolution and Phylogenetics (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades. See, e.g., G Gao, et al, J Virol, 2004 Jun; 78(10): 6381-6388, which identifies Clades A, B, C, D, E and F, and provides nucleic acid sequences of novel AAV, GenBank Accession Numbers AY530553 to AY530629. See, also, WO 2005/033321.

AAVhu68 is described in WO 2018/160582, which incorporated by reference in its entirety herein, and in this detailed description. In certain embodiments, an AAVhu68 capsid is further characterized by one or more of the following: AAVhu68 vp1 proteins produced by expression from a nucleic acid sequence which encodes the predicted amino acid sequence of 1 to 736 of SEQ ID NO: 5, vp1 proteins produced from SEQ ID NO: 4, or vp1 proteins produced from a nucleic acid sequence at least 70% identical to SEQ ID NO: 4 which encodes the predicted amino acid sequence of 1 to 736 of SEQ ID NO: 5; AAVhu68 vp2 proteins produced by expression from a nucleic acid sequence which encodes the predicted amino acid sequence of at least about amino acids 138 to 736 of SEQ ID NO: 5, vp2 proteins produced from a sequence comprising at least nucleotides 412 to 2211 of SEQ ID NO: 4, or vp2 proteins produced from a nucleic acid sequence at least 70% identical to at least nucleotides 412 to 2211 of SEQ ID NO: 4 which encodes the predicted amino acid sequence of at least about amino acids 138 to 736 of SEQ ID NO: 5; and/or AAVhu68 vp3 proteins produced by expression from a nucleic acid sequence which encodes the predicted amino acid sequence of at least about amino acids 203 to 736 of SEQ ID NO: 5, vp3 proteins produced from a sequence comprising at least nucleotides 607 to 2211 of SEQ ID NO: 4, or vp3 proteins produced from a nucleic acid sequence at least 70% identical to at least nucleotides 607 to 2211 of SEQ ID NO: 4 which encodes the predicted amino acid sequence of at least about amino acids 203 to 736 of SEQ ID NO: 5.

The AAVhu68 vp1, vp2 and vp3 proteins are typically expressed as alternative splice variants encoded by the same nucleic acid sequence which encodes the full-length vp1 amino acid sequence (amino acid (aa) 1 to 736). Optionally the vp1-encoding sequence is used alone to express the vp1, vp2 and vp3 proteins. Alternatively, this sequence may be co-expressed with one or more of a nucleic acid sequence which encodes the AAVhu68 vp3 amino acid sequence (about aa 203 to 736) without the vp1-unique region (about aa 1 to about aa 137) and/or vp2-unique regions (about aa 1 to about aa 202), or a strand complementary thereto, the corresponding mRNA or tRNA (for example, the mRNA transcribed from about nucleotide (nt) 607 to about nt 2211 of SEQ ID NO: 4), or a sequence at least 70% to at least 99% (e.g., at least 85%, at least 90%, at least 95%, at least 97%, at least 98% or at least 99%) identical to SEQ ID NO: 4 which encodes aa 203 to 736 of SEQ ID NO: 5. Additionally, or alternatively, the vp1-encoding and/or the vp2-encoding sequence may be co-expressed with the nucleic acid sequence which encodes the AAVhu68 vp2 amino acid sequence of SEQ ID NO: 5 (about aa 138 to 736) without the vp1-unique region (about aa 1 to about 137), or a strand complementary thereto, the corresponding mRNA or tRNA (for example, the mRNA transcribed from nt 412 to 2211 of SEQ ID NO: 4), or a sequence at least 70% to at least 99% (e.g., at least 85%, at least 90%, at least 95%, at least 97%, at least 98% or at least 99%) identical to SEQ ID NO: 4 which encodes about aa 138 to 736 of SEQ ID NO: 5.

As described herein, a rAAVhu68 has a rAAVhu68 capsid produced in a production system expressing capsids from an AAVhu68 nucleic acid sequence which encodes the vp1 amino acid sequence of SEQ ID NO: 5, and optionally additional nucleic acid sequences, e.g., encoding a vp3 protein free of the vp1 and/or vp2-unique regions. The rAAVhu68 resulting from production using a single nucleic acid sequence vp1 produces the heterogeneous populations of vp1 proteins, vp2 proteins and vp3 proteins. More particularly, the AAVhu68 capsid contains subpopulations within the vp1 proteins, within the vp2 proteins and within the vp3 proteins which have modifications from the predicted amino acid residues in SEQ ID NO: 5. These subpopulations include, at a minimum, deamidated asparagine (N or Asn) residues. For example, asparagines in asparagine—glycine pairs are highly deamidated.

In one embodiment, the AAVhu68 vp1 nucleic acid sequence has the sequence of SEQ ID NO: 4, or a strand complementary thereto, e.g., the corresponding mRNA or tRNA.

In certain embodiments, the vp2 and/or vp3 proteins may be expressed additionally or alternatively from different nucleic acid sequences than the vp1, e.g., to alter the ratio of the vp proteins in a selected expression system. In certain embodiments, also provided is a nucleic acid sequence which encodes the AAVhu68 vp3 amino acid sequence of SEQ ID NO: 5 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 4). In certain embodiments, also provided is a nucleic acid sequence which encodes the AAVhu68 vp2 amino acid sequence of SEQ ID NO: 5 (about aa 138 to 736) without the vp1-unique region (about aa 1 to about 137), or a strand complementary thereto, the corresponding mRNA or tRNA (nt 412 to 2211 of SEQ ID NO: 4).

However, other nucleic acid sequences which encode the amino acid sequence of SEQ ID NO: 5 may be selected for use in producing rAAVhu68 capsids. In certain embodiments, the nucleic acid sequence has the nucleic acid sequence of SEQ ID NO: 4 or a sequence at least 70% to 99% identical, at least 75%, at least 80%, at least 85%, at least 90%, at least 95%, at least 97%, at least 99%, identical to SEQ ID NO: 4 which encodes SEQ ID NO: 5. In certain embodiments, the nucleic acid sequence has the nucleic acid sequence of SEQ ID NO: 4 or a sequence at least 70% to 99%, at least 75%, at least 80%, at least 85%, at least 90%, at least 95%, at least 97%, at least 99%, identical to about nt 412 to about nt 2211 of SEQ ID NO: 4 which encodes the vp2 capsid protein (about aa 138 to 736) of SEQ ID NO: 5. In certain embodiments, the nucleic acid sequence has the nucleic acid sequence of about nt 607 to about nt 2211 of SEQ ID NO: 4 or a sequence at least 70% to 99%, at least 75%, at least 80%, at least 85%, at least 90%, at least 95%, at least 97%, at least 99%, identical to nt 607 to about nt 2211 of SEQ ID NO: 4 which encodes the vp3 capsid protein (about aa 203 to 736) of SEQ ID NO: 5.

As used herein when used to refer to vp capsid proteins, the term "heterogeneous" or any grammatical variation thereof, refers to a population consisting of elements that are not the same, for example, having vp1, vp2 or vp3 monomers (proteins) with different modified amino acid sequences. SEQ ID NO: 5 provides the encoded amino acid sequence of the AAVhu68 vp1 protein. The term "heterogeneous" as used in connection with vp1, vp2 and vp3 proteins (alternatively termed isoforms), refers to differences in the amino acid sequence of the vp1, vp2 and vp3 proteins within a capsid. The AAV capsid contains subpopulations within the vp1 proteins, within the vp2 proteins and within the vp3 proteins which have modifications from the predicted amino acid residues. These subpopulations include, at a minimum, certain deamidated asparagine (N or Asn) residues. For example, certain subpopulations comprise at least one, two, three or four highly deamidated asparagines (N) positions in asparagine—glycine pairs and optionally further comprising other deamidated amino acids, wherein the deamidation results in an amino acid change and other optional modifications.

AAVrh.91 is described in WO 2020/223231, as well as in U.S. Provisional Patent Application No. 63/065,616, filed Aug. 17, 2020 and U.S. Provisional Patent Application No. 63/109,734, filed Nov. 4, 2020, each of which is incorporated by reference in its entirety herein. In certain embodiments, an AAVrh.91 capsid is characterized by one or more of the following: 1) AAVrh.91 vp1 proteins produced by expression from a nucleic acid sequence which encodes the predicted amino acid sequence of 1 to 736 of SEQ ID NO: 10, vp1 proteins produced from SEQ ID NO: 9, or vp1 proteins produced from a nucleic acid sequence at least 70% identical to SEQ ID NO: 9 which encodes the predicted amino acid sequence of 1 to 736 of SEQ ID NO: 10; 2) AAVrh.91 vp2 proteins produced by expression from a nucleic acid sequence which encodes the predicted amino acid sequence of at least about amino acids 138 to 736 of SEQ ID NO: 10, vp2 proteins produced from a sequence comprising at least nucleotides 412 to 2211 of SEQ ID NOs: 9, or vp2 proteins produced from a nucleic acid sequence at least 70% identical to at least nucleotides 412 to 2211 of SEQ ID NO: 9 which encodes the predicted amino acid sequence of at least about amino acids 138 to 736 of SEQ ID NO: 10; and/or 3) AAVhu68 vp3 proteins produced by expression from a nucleic acid sequence which encodes the predicted amino acid sequence of at least about amino acids 203 to 736 of SEQ ID NO: 10, vp3 proteins produced from a sequence comprising at least nucleotides 607 to 2211 of SEQ ID NO: 9, or vp3 proteins produced from a nucleic acid sequence at least 70% identical to at least nucleotides 607 to 2211 of SEQ ID NO: 9 which encodes the predicted amino acid sequence of at least about amino acids 203 to 736 of SEQ ID NO: 10.

In certain embodiments, an AAVrh.91 capsid is characterized by one or more of the following: 1) AAVrh.91 vp1 proteins produced by expression from a nucleic acid sequence which encodes the predicted amino acid sequence of 1 to 736 of SEQ ID NO: 10, vp1 proteins produced from SEQ ID NO: 11, or vp1 proteins produced from a nucleic acid sequence at least 70% identical to SEQ ID NO: 11 which encodes the predicted amino acid sequence of 1 to 736 of SEQ ID NO: 10; 2) AAVrh.91 vp2 proteins produced by expression from a nucleic acid sequence which encodes the predicted amino acid sequence of at least about amino acids 138 to 736 of SEQ ID NO: 10, vp2 proteins produced from a sequence comprising at least nucleotides 412 to 2211 of SEQ ID NOs: 11, or vp2 proteins produced from a nucleic acid sequence at least 70% identical to at least nucleotides 412 to 2211 of SEQ ID NO: 11 which encodes the predicted amino acid sequence of at least about amino acids 138 to 736 of SEQ ID NO: 10; and/or 3) AAVhu68 vp3 proteins produced by expression from a nucleic acid sequence which encodes the predicted amino acid sequence of at least about amino acids 203 to 736 of SEQ ID NO: 10, vp3 proteins produced from a sequence comprising at least nucleotides 607 to 2211 of SEQ ID NO: 11, or vp3 proteins produced from a nucleic acid sequence at least 70% identical to at least nucleotides 607 to 2211 of SEQ ID NO: 11 which encodes the predicted amino acid sequence of at least about amino acids 203 to 736 of SEQ ID NO: 10.

As used herein, a "subpopulation" of vp proteins refers to a group of vp proteins which has at least one defined characteristic in common and which consists of at least one group member to less than all members of the reference group, unless otherwise specified. For example, a "subpopulation" of vp1 proteins is at least one (1) vp1 protein and less than all vp1 proteins in an assembled AAV capsid, unless otherwise specified. A "subpopulation" of vp3 proteins may be one (1) vp3 protein to less than all vp3 proteins in an assembled AAV capsid, unless otherwise specified. For example, vp1 proteins may be a subpopulation of vp proteins; vp2 proteins may be a separate subpopulation of vp proteins, and vp3 are yet a further subpopulation of vp proteins in an assembled AAV capsid. In another example, vp1, vp2 and vp3 proteins may contain subpopulations having different modifications, e.g., at least one, two, three or four highly deamidated asparagines, e.g., at asparagine—glycine pairs.

Unless otherwise specified, highly deamidated refers to at least 45% deamidated, at least 50% deamidated, at least 60% deamidated, at least 65% deamidated, at least 70%, at least 75%, at least 80%, at least 85%, at least 90%, at least 95%, at least 97%, at least 99%, or up to about 100% deamidated at a referenced amino acid position, as compared to the predicted amino acid sequence at the reference amino acid position (e.g., at least 80% of the asparagines at amino acid 57 based on the numbering of SEQ ID NO: 5 (AAVhu68) may be deamidated based on the total vp1 proteins may be deamidated based on the total vp1, vp2 and vp3 proteins).

Such percentages may be determined using 2D-gel, mass spectrometry techniques, or other suitable techniques.

Deamidation in the rAAV may be determined using 2D gel electrophoresis, and/or mass spectrometry (MS), and/or protein modelling techniques. Online chromatography may be performed with an Acclaim PepMap column and a Thermo UltiMate 3000 RSLC system (Thermo Fisher Scientific) coupled to a Q Exactive HF with a NanoFlex source (Thermo Fisher Scientific). MS data is acquired using a data-dependent top-20 method for the Q Exactive HF, dynamically choosing the most abundant not-yet-sequenced precursor ions from the survey scans (200-2000 m/z). Sequencing is performed via higher energy collisional dissociation fragmentation with a target value of 1e5 ions determined with predictive automatic gain control and an isolation of precursors was performed with a window of 4 m/z. Survey scans were acquired at a resolution of 120,000 at m/z 200. Resolution for HCD spectra may be set to 30,000 at m/z200 with a maximum ion injection time of 50 ms and a normalized collision energy of 30. The S-lens RF level may be set at 50, to give optimal transmission of the m/z region occupied by the peptides from the digest. Precursor ions may be excluded with single, unassigned, or six and higher charge states from fragmentation selection. Bio-Pharma Finder 1.0 software (Thermo Fischer Scientific) may be used for analysis of the data acquired. For peptide mapping, searches are performed using a single-entry protein FASTA database with carbamidomethylation set as a fixed modification; and oxidation, deamidation, and phosphorylation set as variable modifications, a 10-ppm mass accuracy, a high protease specificity, and a confidence level of 0.8 for MS/MS spectra. Examples of suitable proteases may include, e.g., trypsin or chymotrypsin. Mass spectrometric identification of deamidated peptides is relatively straightforward, as deamidation adds to the mass of intact molecule+0.984 Da (the mass difference between —OH and —NH$_2$ groups). The percent deamidation of a particular peptide is determined by the mass area of the deamidated peptide divided by the sum of the area of the deamidated and native peptides. Considering the number of possible deamidation sites, isobaric species which are deamidated at different sites may co-migrate in a single peak. Consequently, fragment ions originating from peptides with multiple potential deamidation sites can be used to locate or differentiate multiple sites of deamidation. In these cases, the relative intensities within the observed isotope patterns can be used to specifically determine the relative abundance of the different deamidated peptide isomers. This method assumes that the fragmentation efficiency for all isomeric species is the same and independent on the site of deamidation. It is understood by one of skill in the art that a number of variations on these illustrative methods can be used. For example, suitable mass spectrometers may include, e.g, a quadrupole time of flight mass spectrometer (QTOF), such as a Waters Xevo or Agilent 6530 or an orbitrap instrument, such as the Orbitrap Fusion or Orbitrap Velos (Thermo Fisher). Suitably liquid chromatography systems include, e.g., Acquity UPLC system from Waters or Agilent systems (1100 or 1200 series). Suitable data analysis software may include, e.g., MassLynx (Waters), Pinpoint and Pepfinder (Thermo Fischer Scientific), Mascot (Matrix Science), Peaks DB (Bioinformatics Solutions). Still other techniques may be described, e.g., in X. Jin et al, Hu Gene Therapy Methods, Vol. 28, No. 5, pp. 255-267, published online Jun. 16, 2017.

In addition to deamidations, other modifications may occur do not result in conversion of one amino acid to a different amino acid residue. Such modifications may include acetylated residues, isomerizations, phosphory-lations, or oxidations. Modulation of Deamidation: In certain embodiments, the AAV is modified to change the glycine in an asparagine-glycine pair, to reduce deamidation. In other embodiments, the asparagine is altered to a different amino acid, e.g., a glutamine which deamidates at a slower rate; or to an amino acid which lacks amide groups (e.g., glutamine and asparagine contain amide groups); and/or to an amino acid which lacks amine groups (e.g., lysine, arginine and histidine contain amine groups). As used herein, amino acids lacking amide or amine side groups refer to, e.g., glycine, alanine, valine, leucine, isoleucine, serine, threonine, cystine, phenylalanine, tyrosine, or tryptophan, and/or proline. Modifications such as described may be in one, two, or three of the asparagine-glycine pairs found in the encoded AAV amino acid sequence. In certain embodiments, such modifications are not made in all four of the asparagine—glycine pairs. Thus, a method for reducing deamidation of AAV and/or engineered AAV variants having lower deamidation rates. Additionally, or alternative one or more other amide amino acids may be changed to a non-amide amino acid to reduce deamidation of the AAV. In certain embodiments, a mutant AAV capsid as described herein contains a mutation in an asparagine—glycine pair, such that the glycine is changed to an alanine or a serine. A mutant AAV capsid may contain one, two or three mutants where the reference AAV natively contains four NG pairs. In certain embodiments, an AAV capsid may contain one, two, three or four such mutants where the reference AAV natively contains five NG pairs. In certain embodiments, a mutant AAV capsid contains only a single mutation in an NG pair. In certain embodiments, a mutant AAV capsid contains mutations in two different NG pairs. In certain embodiments, a mutant AAV capsid contains mutation is two different NG pairs which are located in structurally separate location in the AAV capsid. In certain embodiments, the mutation is not in the VP1-unique region. In certain embodiments, one of the mutations is in the VP1-unique region. Optionally, a mutant AAV capsid contains no modifications in the NG pairs, but contains mutations to minimize or eliminate deamidation in one or more asparagines, or a glutamine, located outside of an NG pair.

Nucleic acid sequences encoding the capsid of the clade F adeno-associated virus termed AAVhu68 are utilized in the production of the AAVhu68 capsid and recombinant AAV (rAAV) carrying a vector genome. The rAAVhu68.FXN described herein are well suited for delivery of the vector genome comprising the FXN gene to cardiac cells and/or cells within the central nervous system (CNS) (e.g., brain, cerebellum). In certain embodiments, an rAAVhu68.hFXN is used in combination with a second rAAV.hFXN vector having a different capsid, optionally delivered via the same route or via a different route. In certain embodiments, an rAAV.hFXN as described herein has a different capsid, which is suitable for delivering a vector genome to the CNS, cardiac, or another cell type. Suitable capsids include, for example, AAVcy02, AAV8, AAVrh43, AAV9, AAVrh08, AAVrh10, AAVbb01, AAVhu37, AAVrh20, AAVrh39, AAV1, AAVhu48, AAVcy05, AAVhu11, AAVhu32, AAVrh.91 and AAVpi02, among others.

As used herein, the term "vector genome" refers to a nucleic acid molecule which is packaged in a viral capsid, for example, an AAV capsid, and is capable of being delivered to a host cell or a cell in a patient. In certain embodiments, the vector genome is an expression cassette having inverted terminal repeat (ITR) sequences necessary for packaging the vector genome into the AAV capsid at the extreme 5' and 3' end and containing therebetween a FXN gene as described herein operably linked to sequences which direct expression thereof.

As used herein, an "AAV9 capsid" is a self-assembled AAV capsid composed of multiple AAV9 vp proteins. The AAV9 vp proteins are typically expressed as alternative splice variants encoded by a nucleic acid sequence of SEQ ID NO: 6 or a sequence at least 70%, at least 75%, at least 80%, at least 85%, at least 90%, at least 95%, at least 97%, at least 99% thereto, which encodes the vp1 amino acid sequence of GenBank accession: AAS99264. In certain embodiments, "AAV9 capsid" includes an AAV having an amino acid sequence which is 99% identical to AAS99264 or 99% identical to SEQ ID NO: 7. See, also U.S. Pat. No. 7,906,111 and WO 2005/033321. As used herein "AAV9 variants" include those described in, e.g., WO2016/049230, U.S. Pat. No. 8,927,514, US 2015/0344911, and U.S. Pat. No. 8,734,809.

Methods of generating the capsid, coding sequences therefore, and methods for production of rAAV have been described. See, e.g., Gao, et al, Proc. Natl. Acad. Sci. U.S.A. 100 (10), 6081-6086 (2003) and US 2013/0045186A 1.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV9 sequences as a reference point. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13): 2682-2690 (1999).

rAAVs have been previously described as suitable vehicles for gene delivery. Typically, an exogenous expression cassette comprising the transgene (for example, the FXN gene) for delivery by the rAAV replaces the functional rep genes and the cap gene from the native AAV source, resulting in a replication-incompetent vector. These rep and cap functions are provided in trans during the vector production system but absent in the final rAAV.

As indicated above, a rAAV is provided which has an AAV capsid and a vector genome which comprises, at a minimum, AAV inverted terminal repeats (ITRs) required to package the vector genome into the capsid, a FXN gene and regulatory sequences which direct expression of the FXN gene. In certain embodiments, the AAV capsid is from AAVhu68. The examples herein utilize a single-stranded AAV vector genome, but in certain embodiments, a rAAV be utilized in the invention which contains a self-complementary (sc) AAV vector genome.

The regulatory control elements necessary are operably linked to the gene (e.g., FXN) in a manner which permits its transcription, translation and/or expression in a cell which takes up the rAAV. As used herein, "operably linked" sequences include both expression control sequences that are contiguous with the gene of interest and expression control sequences that act in trans or at a distance to control the gene of interest. Such regulatory sequences typically include, e.g., one or more of a promoter, an enhancer, an intron, a polyA, and a self-cleaving linker (e.g., furin, furin-F2A, an IRES). The examples below utilize the CB7 promoter (e.g., nt 198-579 of SEQ ID NO: 8 (CMV IE promoter) through CB promoter (nt 582-863 of SEQ IDNO: 8)) for expression of the FAN gene. However, in certain embodiments, other promoters, or an additional promoter, may be selected.

In certain embodiments, in addition to the FXN gene, a non-AAV sequence encoding another one or more of gene products may be included in the vector genome. Such gene products may be, e.g., a peptide, polypeptide, protein, functional RNA molecule (e.g., miRNA, miRNA inhibitor) or other gene product, of interest. Useful gene products may include miRNAs. miRNAs and other small interfering nucleic acids regulate gene expression via target RNA transcript cleavage/degradation or translational repression of the target messenger RNA (mRRNA). miRNAs are natively expressed, typically as final 19-25 non-translated RNA products, miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The AAV vector genome typically includes cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are about 145 base pairs (bp) in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid. In one embodiment, the ITR sequences are from AAV2. A shortened version of the 5' ITR, termed AITR, has been described in which the D-sequence and terminal resolution site (trs) are deleted. In certain embodiments, the vector genome includes a shortened AAV2 ITR of 130 base pairs, wherein the external A elements is deleted. The shortened ITR is reverted back to the wild type length of 145 base pairs during vector DNA amplification using the internal A element as a template. In other embodiments, the full-length AAV 5' and 3' ITRs are used. See, SEQ ID NO: 8. See, also, SEQ ID NO: 12. However, ITRs from other AAV sources may be selected. Where the source of the ITRs is from AAV2 and the AAV capsid is from another AAV source, the resulting rAAV may be termed pseudotyped. However, other configurations of these elements may be suitable.

In certain embodiments, an additional or alternative promoter sequence may be included as part of the expression control sequences (regulatory sequences), e.g., located between the selected 5' ITR sequence and the coding sequence. Constitutive promoters, regulatable promoters (see, e.g., WO 2011/126808 and WO 2013/04943), tissue specific promoters (for example, a neuron specific promoter or a glial cell specific promoter, or a CNS specific promoter), or a promoter responsive to physiologic cues may be utilized in the rAAVs described herein. The promoter(s) can be selected from different sources, e.g., human cytomegalovirus (CMV) immediate-early enhancer/promoter, the SV40 early enhancer/promoter, the JC polyomavirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. Other suitable promoter may include a CB7 promoter. In addition to a promoter, a vector genome may contain one or more other appropriate transcription initiation sequences, transcription termination sequences, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the regulatory sequences comprise one or more expression enhancers. In one embodiment, the regulatory sequences contain two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g., the chicken beta-actin intron. In certain embodiments, the intron is a chimeric intron (C1)—a hybrid intron consisting of a human beta-globin splice donor and immunoglobulin G (IgG) splice acceptor elements. Other suitable introns include those known in the art, e.g., such as are described in WO 2011/126808. Examples of suitable polyA sequences include, e.g., SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence (see, e.g., MA Zanta-Boussif, et al, *Gene Therapy* (2009) 16: 605-619). In certain embodiments, no WPRE sequence is present.

In certain embodiments, vector genomes are constructed which comprise a 5' AAV ITR—promoter—optional enhancer—optional intron—FXN gene—polyA—3' ITR. In certain embodiments, the ITRs are from AAV2. In certain embodiments, the vector genome comprises SEQ ID NO: 8 or SEQ ID NO: 12. In certain embodiments, the vector genome comprises a 5' ITR, nucleotides 198 to 2737 of SEQ ID NO: 8 and a 3' ITR. In the embodiments, the vector genome comprises a 5' ITR, nucleotides 198 to 2736 of SEQ ID NO: 12, and a 3' ITR. In certain embodiments, more than one promoter is present. In certain embodiments, the enhancer is present in the vector genome. In certain embodiments, more than one enhancer is present. In certain embodiments, an intron is present in the vector genome. In certain embodiments, the enhancer and intron are present. In certain embodiments, the polyA is a rabbit beta-globin (RBG) poly A. In certain embodiments, the vector genome comprises a 5' AAV ITR—CB7 promoter—FXN gene—RBG poly A—3' ITR. In certain embodiments, the FAN gene includes SEQ ID NO: 3. In certain embodiments, the vector genome has the sequence of SEQ ID NO: 8 or a sequence at least about 85%, 90%, 91%, 92%, 93%, 94%, 95%, 96%,97%, 98%, or 99%, to about 99.9% identical thereto. In certain embodiments, the vector genome has the sequence of SEQ ID NO: 12 or a sequence at least about 85%, 90%, 91%, 92%, 93%, 94%, 95%, 96%,97%, 98%, or 99%, to about 99.9% identical thereto.

In certain embodiments, the vector genome further comprises a dorsal root ganglion (DRG)-specific miRNA target sequence, which allows for modulation of frataxin expression wherein expression of frataxin is repressed in DRG neurons. Such modulation of FXN transgene expression allows for decreased toxicity, thereby improving safety. See, e.g., PCT/US19/67872, filed Dec. 20, 2019 and now published as WO 2020/132455. See, also, U.S. Provisional Patent Application No. 63/023,593, filed May 12, 2020; U.S. Provisional Patent Application No. 63/038,488, filed Jun. 12, 2020; U.S. Provisional Patent Application No. 63/043, 562, filed Jun. 24, 2020; and U.S. Provisional Patent Application No. 63/079,299, filed Jun. 24, 2020, which are incorporated herein by reference.

In certain embodiments, provided herein are vector genomes comprising at least one copy of DRG-specific miRNA target sequence operably linked to a FX transgene to repress expression of the transgene in DRG and/or reduce or eliminate DRG toxicity and/or axonopathy. In certain embodiments, the vector genome comprises multiple DRG-specific miRNA target sequences, such that the number of miRNA target sequences is sufficient to reduce or minimize transgene expression in DRG to reduce and/or eliminate DRG toxicity and/or axonopathy. In some embodiments, the vector genome comprises at least two, or at least three tandem repeats of dorsal root ganglion (DRG)-specific miRNA target sequences, optionally separated by a spacer. In some embodiments, the DRG-specific miRNA target sequence/s are located at 5' end of FX transgene. In some embodiments, the DRG-specific miRNA target sequence/s are located at 3' end of FXN transgene. In certain embodiments, the vector genome comprises a 5' AAV ITR—CB7 promoter—FA gene—one, two, or three DRG-specific miRNA targeting sequence/s—RBG poly A—3' ITR. Such vector genome may be delivered via any suitable carrier system, viral vector or non-viral vector, via any route, but is particularly useful for intrathecal and intraparenchymal administration.

II. rAAV Production

Vector genomes for use in producing an AAV viral vector (e.g., a recombinant (r) AAV) can be carried on any suitable vector, e.g., a plasmid, which is delivered to a packaging host cell. Plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, Adeno-associated virus as a gene therapy vector: Vector development, production and clinical applications, *Adv. Biochem. Engin Biotechnol.* 99: 119-145; Buning et al., 2008, Recent developments in adeno-associated virus vector technology, J Gene Med. 10:717-733; and the references cited below, each of which is incorporated herein by reference in its entirety. For packaging a gene into virions, the ITRs are the only AAV components required in cis in the same construct as the nucleic acid molecule containing the gene. The cap and rep genes can be supplied in trans.

In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product (for example, 0-gal). These empty capsids are non-functional to transfer the gene of interest to a host cell. In certain embodiment, the rAAV.FXN or the composition as described herein may be at least about 80%, 85%, 90%, 95%, 96%, 97%, 98%, 99% or 99.9% free from an AAV intermediate, i.e., containing less than 20%, 15%, 10%, 5%, 4%, 3%, 2%, 1%, or 0.1% AAV intermediates.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette composed of, at a minimum, AAV inverted terminal repeats (ITRs) and a transgene; and sufficient helper functions to permit packaging of the expression cassette into the AAV capsid protein. Methods of generating the capsid, coding sequences therefor, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, a production cell culture useful for producing a recombinant AAV (such as rAAVhu68) is provided. Such a cell culture contains a nucleic acid which expresses the AAV capsid protein in the host cell; a nucleic acid molecule suitable for packaging into the AAV capsid, e.g., a vector genome which contains AAV ITRs and a FXN gene operably linked to regulatory sequences which direct expression of the gene in a cell (for example, a cell in a patient in need); and sufficient AAV rep functions and adenovirus helper functions to permit packaging of the vector genome into the recombinant AAV capsid. In one embodiment, the cell culture is composed of mammalian cells (e.g., human embryonic kidney 293 cells, among others) or insect cells (e.g., *Spodoptera frugiperda* (Sf9) cells). In certain embodiments, baculovirus provides the helper functions necessary for packaging the vector genome into the recombinant AAVhu68 capsid.

Optionally the rep functions are provided by an AAV other than the capsid source AAV. In certain embodiments, at least parts of the rep functions are from AAVhu68. In another embodiment, the rep protein is a heterologous rep protein other than AAVhu68 rep, for example but not limited to, AAV1 rep protein, AAV2 rep protein, AAV3 rep protein, AAV4 rep protein, AAV5 rep protein, AAV6 rep protein, AAV7 rep protein, AAV8 rep protein; or rep 78, rep 68, rep 52, rep 40, rep68/78 and rep40/52; or a fragment thereof; or another source. Any of these AAVhu68 or mutant AAV capsid sequences may be under the control of exogenous regulatory control sequences which direct expression thereof in a host cell.

In one embodiment, vectors are manufactured in a suitable cell culture (e.g., HEK 293 or Sf9) or suspension. Methods for manufacturing the gene therapy vectors described herein include methods well known in the art such as generation of plasmid DNA used for production of the gene therapy vectors, generation of the vectors, and purification of the vectors. In some embodiments, the gene therapy vector is a rAAV and the plasmids generated are an AAV cis-plasmid encoding the AAV vector genome comprising the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, Adenovirus-adeno-associated virus hybrid for large-scale recombinant adeno-associated virus production, Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The crude cell harvest may thereafter be subject method steps such as concentration of the rAAV harvest, diafiltration of the rAAV harvest, microfluidization of the rAAV harvest, nuclease digestion of the rAAV harvest, filtration of microfluidized intermediate, crude purification by chromatography, crude purification by ultracentrifugation, buffer exchange by tangential flow filtration, and/or formulation and filtration to prepare bulk rAAV. A two-step affinity chromatography purification at high salt concentration followed anion exchange resin chromatography are used to purify the rAAV drug product and to remove empty capsids. These methods are described in more detail in WO 2017/160360, International Patent Application No. PCT/US2016/065970, filed Dec. 9, 2016 and its priority documents, US Patent Application Nos. 62/322,071, filed Apr. 13, 2016 and 62/226,357, filed Dec. 11, 2015 and entitled "Scalable Purification Method for AAV9", which is incorporated by reference herein.

To calculate empty and full particle content, VP3 band volumes for a selected sample (e.g., in examples herein an iodixanol gradient-purified preparation where # of genome copies (GC)=# of particles) are plotted against GC particles loaded. The resulting linear equation ($y=mx+c$) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles. In certain embodiments, the AAV viral capsid purity is greater than or equal to about 90% virion protein as measured with SDS-PAGE.

Generally, methods for assaying for empty capsids and rAAV particles with packaged vector genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the rAAV is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb 14.

In brief, the method for separating rAAV particles having packaged genomic sequences from genome-deficient rAAV intermediates involves subjecting a suspension comprising rAAV viral particles and rAAV capsid intermediates to fast performance liquid chromatography, wherein the rAAV viral particles and rAAV intermediates are bound to a strong anion exchange resin equilibrated at a pH of about 10.2, and subjected to a salt gradient while monitoring eluate for ultraviolet absorbance at about 260 nanometers (nm) and about 280 nm. Although less optimal for rAAVhu68, the pH may be in the range of about 10.0 to 10.4. In this method, the AAVhu68 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/hu68 serotype. Under these ionic conditions, a significant percentage of residual cellular DNA and proteins flow through the column, while AAV particles are efficiently captured.

The rAAV.FXN (for example, rAAVhu68.FXN) is suspended in a suitable physiologically compatible composition (e.g., a buffered saline). This composition may be frozen for storage, later thawed and optionally diluted with a suitable diluent. Alternatively, the rAAV.FXN may be prepared as a composition which is suitable for delivery to a patient without proceeding through the freezing and thawing steps.

Also provided herein is a production vector (such as a plasmid) or a host cell for producing the vector genome and/or the rAAV.FXN as described herein. As used herein, a production vector carries a vector genome to a host cell for generating and/or packaging a gene therapy vector as described herein. In certain embodiments, a plasmid with an expression cassette having a FXN gene with the sequence of SEQ ID NO: 3 or a sequence 95% identical thereto that encodes human frataxin is provided. In further embodiments, the plasmid has a FXN gene that encodes a human frataxin protein having a sequence of SEQ ID NO: 2, or a sequence at least 95% identical thereto. In certain embodiments, the plasmid includes a vector genome having at least a 5' AAV ITR, promoter, FXN gene, polyA, and a 5' AAV ITR. In certain embodiments, the plasmid includes SEQ ID NO: 8 or 12, or a sequence at least 95% identical to SEQ ID NO: 8 or 12. In another embodiment, a host cell containing a plasmid as described herein is provided.

III. Pharmaceutical Compositions and Methods of Treatment

Provided herein are compositions containing a rAAV and an optional carrier, excipient and/or preservative.

As used herein, a "stock" of rAAV refers to a population of rAAV. Despite heterogeneity in their capsid proteins due to deamidation, rAAV in a stock are expected to share an identical vector genome. A stock can include rAAV having capsids with, for example, heterogeneous deamidation patterns characteristic of the selected AAV capsid proteins and a selected production system. The stock may be produced from a single production system or pooled from multiple runs of the production system. A variety of production systems, including but not limited to those described herein, may be selected.

In particular, the compositions provided are for the treatment of FRDA. In one embodiment, the composition is suitable for administration to a patient having FRDA or a patient who is 18 months of age or younger. In one embodiment, the composition is suitable for administration to a patient having FRDA which is 16 years old or older, and wherein the onset of FRDA was at 14 years old or younger. In one embodiment, the composition is suitable for administration to a patient in need thereof to ameliorate one or more symptoms of FA, or ameliorate one or more neurological symptoms of FRDA, or ameliorate one or more cardiac symptoms of FRDA. In some embodiments, the composition is for use in the manufacture of a medicament for the treatment of FRDA. In some embodiments, the composition is for use in the manufacture of a medicament for treatment of FRDA in patients of 16 years old or older, and wherein onset of FRDA was at 14 years old or younger. In certain embodiments, the patient is 10 years of age or younger to 25 years of age or older. In certain embodiments, the patient receiving the rAAV.FXN is 10 years to 40 years of age. In certain embodiments, the patient receiving the rAAV.FXN is from 10 years to 40 years of age, from 10 years to 15 years of age, or from 15 years to 40 years of age.

In certain embodiments, the gene therapy vector provided herein is useful for treatment of neurological conditions associated with deficiencies in levels of functional frataxin in a subject. In certain embodiments, the gene therapy vector or the composition provided herein is useful for amelioration of cardiac symptoms associated with FRDA. In certain embodiments, the gene therapy vector or the composition provided herein is useful for amelioration of diabetes symptoms associated with FRDA. In certain embodiments, amelioration of the following symptoms associated with FRDA are observed following treatment. Such improvement may include, e.g., improvement in cardiac symptoms (e.g., permitting reduction or elimination of anti-arrhythmic agents and/or anti-cardiac failure medication). In certain embodiments, treatment of the subject includes dietary modification, oral hypoglycemic therapeutics, and/or insulin for controlling diabetes mellitus. In certain embodiments, vision and hearing problems in the subject may be alleviated with either corrective devices and/or drugs. In certain embodiments, the subject's intelligence remains unaffected. In certain embodiments, psychological counseling may be helpful to relieve emotional strain that affects patients and their families. In certain embodiments, speech therapy is included to help the subject maximize verbal communication skills.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

In certain embodiments, provided herein is a composition comprising a rAAV.FXN as described herein and a pharmaceutically acceptable carrier. The phrase "pharmaceutically-acceptable" refers to molecular entities and compositions that do not produce an allergic or similar untoward reaction when administered to a host.

In certain embodiments, provided herein is a composition comprising a rAAV.FXN as described herein and a delivery vehicle. Delivery vehicles such as liposomes, nanocapsules, microparticles, microspheres, lipid particles, vesicles, and the like, may be used for the introduction of the compositions of the present invention into suitable host cells.

In particular, the rAAV delivered vector genomes may be formulated for delivery either encapsulated in a lipid particle, a liposome, a vesicle, a nanosphere, or a nanoparticle or the like.

In one embodiment, a composition includes a final formulation suitable for delivery to a subject/patient, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. In one embodiment, the surfactant may be present in an amount up to about 0.0005% to about 0.001% (based on weight ratio, w/w %) of the suspension. In another embodiment, the surfactant may be present in an amount up to about 0.0005% to about 0.001% (based on volume ratio, v/v %) of the suspension. In yet another embodiment, the surfactant may be present in an amount up to about 0.0005% to about 0.001% of the suspension, wherein n % indicates n gram per 100 mL of the suspension.

The rAAV.FXN is administered in sufficient amounts to transduce cells of the subject and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., brain, CSF, heart), oral, inhalation, intranasal, intrathecal, intratracheal, intraarterial, intraocular, intravenous, intramuscular, subcutaneous, intradermal, intraparenchymal, intracerebroventricular, intrathecal, ICM, lumbar puncture and other parenteral routes of administration. Routes of administration may be combined, if desired.

Dosages of the rAAV.FXN depend primarily on factors such as the condition being treated, the age, weight and health of the patient, and can thus vary among patients. For example, a therapeutically effective human dosage of the rAAV.FXN is generally in the range of from about 25 to about 1000 microliters to about 100 mL of solution containing concentrations of from about $1 \times 10^9$ to $1 \times 10^{16}$ vector genome copies. In certain embodiments, a volume of about 1 mL to about 15 mL, or about 2.5 mL to about 10 mL, or about 5 mL suspension is delivered. In certain embodiments, a volume of about 1, about 2, about 3, about 4, about 5, about 6, about 7, about 8, about 9, about 10, about 11, about 12, about 13, about 14, or about 15 mL suspension is delivered.

In some embodiments, the composition is for administration in a single dose. In some embodiments, the composition is for administration via multiple routes of delivery.

In certain embodiments, delivery via intravenous administration is contemplated with a dose ranging from about $8 \times 10^{12}$ genome copies (GC)/kg of rAAV.FXN to about $3 \times 10^{14}$ GC of rAAV.FXN per kg is administered. In certain embodiments, a dose is about $1 \times 10^{13}$ GC/kg to about $1 \times 10^{14}$ GC of rAAV.FXN per patient, or about $3 \times 10^{13}$ GC/kg. In certain embodiments, delivery via intravenous administration is contemplated with a dose of about $3 \times 10^{12}$ GC/kg to about $1 \times 10^{14}$ GC/kg, further including doses of about $3.0 \times 10^{13}$ GC/kg and about $1.0 \times 10^{13}$ GC/kg.

In certain embodiments, a dose from $1 \times 10^{10}$ GC of rAAV.FXN per g brain mass (GC/g brain mass) to $3.4 \times 10^{11}$ GC/g brain mass is administered in the volume as described herein. In certain embodiments, a dose from $3.4 \times 10^{10}$ GC/g brain mass to $3.4 \times 10^{11}$ GC/g brain mass, or from $1.0 \times 10^{11}$ GC/g brain mass to $3.4 \times 10^{11}$ GC/g brain mass, or about $1.1 \times 10^{11}$ GC/g brain mass, or from about $1.1 \times 10^{10}$ GC/g brain mass to about $3.3 \times 10^{11}$ GC/g brain mass is administered in the volume. In certain embodiments, a dose of about $3.0 \times 10^9$, about $4.0 \times 10^9$, about $5.0 \times 10^9$, about $6.0 \times 10^9$, about $7.0 \times 10^9$, about $8.0 \times 10^9$, about $9.0 \times 10^9$, about $1.0 \times 10^{10}$, about $1.1 \times 10^{10}$, about $1.5 \times 10^{10}$, about $2.0 \times 10^{10}$, about $2.5 \times 10^{10}$, about $3.0 \times 10^{10}$, about $3.3 \times 10^{10}$, about $3.5 \times 10^{10}$, about $4.0 \times 10^{10}$, about $4.5 \times 10^{10}$, about $5.0 \times 10^{10}$, about $5.5 \times 10^{10}$, about $6.0 \times 10^{10}$, about $6.5 \times 10^{10}$, about $7.0 \times 10^{10}$, about $7.5 \times 10^{10}$, about $8.0 \times 10^{10}$, about $8.5 \times 10^{10}$, about $9.0 \times 10^{10}$, about $9.5 \times 10^{10}$, about $1.0 \times 10^{11}$, about $1.1 \times 10^1$, about $1.5 \times 10^{11}$, about $2.0 \times 10^{11}$, about $2.5 \times 10^{11}$, about $3.0 \times 10^{11}$, about $3.3 \times 10^{11}$ about $3.5 \times 10^{11}$, about $4.0 \times 10^{11}$, about $4.5 \times 10^{11}$, about $5.0 \times 10^{11}$, about $5.5 \times 10^{11}$, about $6.0 \times 10^1$, about $6.5 \times 10^{11}$, about $7.0 \times 10^{11}$, about $7.5 \times 10^{11}$, about $8.0 \times 10^{11}$, about $8.5 \times 10^{11}$ about $9.0 \times 10^{11}$ GC per gram brain mass is administered in the volume.

The replication-defective virus compositions can be formulated in dosage units to contain an amount of replication-defective virus (for example, rAAV.FXN, rAAVhu68.FXN, or rAAVhu68.CB7.FXN) that is in the range of about $1.0 \times 10^9$ GC to about $1.0 \times 10^{16}$ GC (to treat an subject) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$ $6 \times 10^{10}$, $7 \times 10^{10}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{11}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{11}$, $4 \times 10^{10}$, $5 \times 10^{10}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 μL. In one embodiment, the volume is about 50 μL. In another embodiment, the volume is about 75 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 225 μL. In yet another embodiment, the volume is about 250 μL. In yet another embodiment, the volume is about 275 μL. In yet another embodiment, the volume is about 300 μL. In yet another embodiment, the volume is about 325 μL. In another embodiment, the volume is about 350 μL. In another embodiment, the volume is about 375 μL. In another embodiment, the volume is about 400 μL. In another embodiment, the volume is about 450 μL. In another embodiment, the volume is about 500 μL. In another embodiment, the volume is about 550 μL. In another embodiment, the volume is about 600 μL. In another embodiment, the volume is about 650 μL. In another embodiment, the volume is about 700 μL. In another embodiment, the volume is from about 700 to 1000 μL.

In certain embodiments, the dose may be in the range of about $1 \times 10'$ GC/g brain mass to about $1 \times 10^{12}$ GC/g brain mass. In certain embodiments, the dose may be in the range of about $3 \times 10^{10}$ GC/g brain mass to about $3 \times 10^{11}$ GC/g brain mass. In certain embodiments, the dose may be in the range of about $5 \times 10^{10}$ GC/g brain mass to about $1.85 \times 10^{11}$ GC/g brain mass.

In one embodiment, the viral constructs may be delivered in doses of from at least about least $1 \times 10^9$ GC to about $1 \times 10^{15}$, or about $1 \times 10^{11}$ to $5 \times 10^{13}$ GC. Suitable volumes for delivery of these doses and concentrations may be determined by one of skill in the art. For example, volumes of about 1 μL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage may be adjusted to balance the therapeutic benefit against any side effects and such dosages may vary depending upon the therapeutic application for which the rAAV.FXN is employed.

In certain embodiments, the rAAV or composition may be delivered via intraparenchymal (dentate nucleus) (IDN) at a dose of about $1\times10^{11}$ to about $3\times10^{13}$, or about 1 to $2\times10^{13}$, or about $1.7\times10^{13}$ GC in 200 μL (i.e., unilateral administration). In some embodiments, the rAAV or a composition may be delivered via IDN at a dose of about $1\times10^{11}$ to about $3\times10^{13}$, or about $8\times10^{12}$ GC in 100 μL (i.e., bilateral administration). In some embodiments, the rAAV or composition may be delivered via IDN at a dose of about $3\times10^{12}$ GC.

In certain embodiments, the composition is administered in each dentate nucleus injected at a rate of 0.5 μL/min initially, and then at an increased rate of up to 5 μL/min, 10 μL/min, 15 μL/min, or 20 μL/min based or idn refers on clinician discretion during the procedure. Such procedure may take approximately 5-6 hours and the subjects are anesthetized for the duration of the procedure.

The above-described rAAV.FXN may be delivered to a subject according to published methods. The rAAV, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.0 to 7.5, or pH 6.2 to 7.7, or pH 6.5 to 7.5, pH 7.0 to 7.7, or pH 7.2 to 7.8, or about 7.0. In certain embodiments, the formulation is adjusted to a pH of about 6.0, about 6.1, about 6.2, about 6.3, about 6.4, about 6.5, about 6.6, about 6.7, about 6.8, about 6.9, about 7.0, about 7.1, about 7.2, about 7.3 about 7.4, about 7.5, about 7.6, about 7.7, or about 7.8. In certain embodiments, a pH of about 7.28 to about 7.32, about 6.0 to about 7.5, about 6.2 to about 7.7, about 7.5 to about 7.8, about 6.0, about 6.1, about 6.2, about 6.3, about 6.4, about 6.5, about 6.6, about 6.7, about 6.8, about 6.9, about 7.0, about 7.1, about 7.2, about 7.3 about 7.4, about 7.5, about 7.6, about 7.7, or about 7.8 may be desired for intrathecal delivery; whereas for intravenous delivery, a pH of about 6.8 to about 7.2 may be desired. However, other pHs within the broadest ranges and these subranges may be selected for other route of delivery.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo. A suitable surfactant, or combination of surfactants, may be selected from among non-ionic surfactants that are nontoxic. In one embodiment, a difunctional block copolymer surfactant terminating in primary hydroxyl groups is selected, e.g., such as Poloxamer 188 (also known under the commercial names Pluronic® F68 [BASF], Lutrol® F68, Synperonic® F68, Kolliphor® P188) which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy-oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate·$7H_2O$), potassium chloride, calcium chloride (e.g., calcium chloride·$2H_2O$), dibasic sodium phosphate, and mixtures thereof, in water. Suitably, for intrathecal delivery, the osmolarity is within a range compatible with cerebrospinal fluid (e.g., about 275 milliosmoles/liter (mOsm/L) to about 290 mOsm/L); see, e.g., emedicine.medscape.com/-article/2093316-overview.

Optionally, for intrathecal delivery, a commercially available diluent may be used as a suspending agent, or in combination with another suspending agent and other optional excipients. See, e.g., Elliotts B® solution [Lukare Medical]. In certain embodiments, the intrathecal final formulation buffer (ITFFB) formulation buffer comprises an artificial cerebrospinal fluid comprising buffered saline and one or more of sodium, calcium, magnesium, potassium, or mixtures thereof; and a surfactant. In certain embodiments, the surfactant comprises about 0.0005% to about 0.001% of the suspension. In a further embodiment, the percentage (%) is calculated based on weight (w) ratio (i.e., w/w). In certain embodiments, the composition containing the rAAVhu68.FXN (e.g., the ITFFB formulation) is at a pH in the range of 6.0 to 7.5, or 6.2 to 7.7, or 6.8 to 8, or 7.2 to 7.8, or 7.5 to 8. In certain embodiments, the final formulation is at a pH of about 7, or 7 to 7.4, or 7.2. In certain embodiments, for intrathecal delivery, a pH above 7.5 may be desired, e.g., 7.5 to 8, or 7.8. In certain embodiments, a pH of about 7 is desired for intrathecal delivery as well as other delivery routes.

In certain embodiments, the formulation may contain a buffered saline aqueous solution not comprising sodium bicarbonate. Such a formulation may contain a buffered saline aqueous solution comprising one or more of sodium phosphate, sodium chloride, potassium chloride, calcium chloride, magnesium chloride and mixtures thereof, in water, such as a Harvard's buffer. The aqueous solution may further contain Kolliphor® P188, a poloxamer which is commercially available from BASF which was formerly sold under the trade name Lutrol® F68. In certain embodiment, the aqueous solution may have a pH of 7.2. In certain embodiment, the aqueous solution may have a pH of about 7.

In another embodiment, the formulation may contain a buffered saline aqueous solution comprising 1 mM Sodium Phosphate ($Na_3PO_4$), 150 mM sodium chloride (NaCl), 3 mM potassium chloride (KCl), 1.4 mM calcium chloride ($CaCl_2$)), 0.8 mM magnesium chloride ($MgCl_2$), and 0.001% poloxamer (e.g., Kolliphor®) 188. In certain embodiments, the formulation has a pH of about 7.2. In certain embodiments, the formulation has a pH of about 7. See, e.g., harvardapparatus.com/harvard-apparatus-perfusion-fluid.html. In certain embodiments, Harvard's buffer is preferred due to better pH stability observed with Harvard's buffer. The below provides a comparison of Harvard's buffer and Elliot's B buffer.

TABLE 1

| Cerebrospinal Fluid (CSF) Compositions. | | | | |
|---|---|---|---|---|
| Component | Units | CSF | Elliot's B | Harvard's |
| $Na^+$ | mEq/L | 117-137 | 149 | 150 |
| $K^+$ | mEq/L | 2.3-4.6 | 4.0 | 3.0 |
| $Mg^+$ | mEq/L | 2.2 | 2.4 | 0.8 |
| $Ca^{2+}$ | mEq/L | 2.2 | 2.7 | 1.4 |
| $Cl^-$ | mEq/L | 113-127 | 132 | 155 |
| $HCO_3^-$ | mEq/L | 22.9 | 22.6 | 0 |
| Phos | mg/dL | 1.2-2.1 | 1.5 | 1.0 |
| Glucose | mg/dL | 45-80 | 80 | — |
| Pluronic | % | — | 0.001% (added) | 0.001% (added) |
| Osmolarity | mOsm/L | 295 | 288 | 290 |
| pH | | 7.31 | 6.0-7.5* Drift to 9+ (8.2+ w/o titratn) | 7.2 (titrated to) |

In certain embodiments, the formulation buffer is artificial CSF with Pluronic F68. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery. In one embodiment, the composition is formulated for administration via an intra-cisterna *magna* injection (ICM). In one embodiment, the composition is formulated for administration via a CT-guided sub-occipital injection into the cisterna *magna*.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna *magna*.

As used herein, the terms "intracisternal delivery" or "intracisternal administration" refer to a route of administration for drugs directly into the cerebrospinal fluid of the cisterna *magna* cerebellomedularis, more specifically via a suboccipital puncture or by direct injection into the cisterna *magna* or via permanently positioned tube.

As used herein, the term "intraparenchymal (dentate nucleus)" or IDN refers to a route of administration of a composition directly into dentate nuclei. IDN allows for targeting of dentate nuclei and/or cerebellum. In certain embodiments, the IDN administration is performed using ClearPoint® Neuro Navigation System (MRI Interventions, Inc., Memphis, TN) and ventricular cannula, which allows for MRI-guided visualization and administration. Alternatively, other devices and methods may be selected.

As used herein, the term "dual route(s) of delivery" refers to a route of administration for a composition comprising delivering the composition systemically (e.g., heart) and to the CNS (e.g., dentate nucleus, DRG sensory neurons, upper motor neurons).

As used herein, the term "NAb titer" refers to a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009.199(3): p. 381-390, which is incorporated by reference herein.

In some embodiments, the administration of the rAAV or a composition ameliorates symptoms of FRDA, such as neurological symptoms of FRDA. In some embodiments, following treatment, the patient has one or more of increased average life span, decreased need for a feeding tube, reduction in seizure incidence and frequency, reduction in progression towards neurocognitive decline and/or improvement in neurocognitive development.

As used herein, an "expression cassette" refers to a nucleic acid molecule which comprises a coding sequence, promoter, and may include other regulatory sequences therefor. In certain embodiments, a vector genome may contain two or more expression cassettes. In other embodiments, the term "transgene" may be used interchangeably with "expression cassette". Typically, such an expression cassette for generating a viral vector contains the coding sequence for the gene product described herein flanked by packaging signals of the viral genome and other expression control sequences such as those described herein.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

A "replication-defective virus" or "viral vector" refers to a synthetic or artificial viral particle in which a vector genome comprising an expression cassette containing a gene A comparison of the clinical features and disease progression of these murine KO mouse models and human adult FRDA patients is presented in Table 3.

TABLE 3

| | Mutation | Biochemical Abnormalities | Histopathology | Clinical Presentation |
|---|---|---|---|---|
| Fxn Cardiac Conditional Mouse | Deletion of exon 2 or 4 of the FXN gene | Reduced cellular respiration | Abnormal mitochondria Hypertrophic cardiomyopathy Iron accumulation Cardiac fibrosis | Decrease survival and body weight, progressive cardiomyopathy |
| Fxn Neurological Conditional Mouse | Deletion of exon 2 or 4 of the FXN gene | Reduced cellular respiration | Abnormal mitochondria Neurodegeneration Iron accumulation | Decrease survival and ataxia |
| Human FDRA Patients | GAA repeat expansion (different length) in intron 1 of the FXN gene | Reduced cellular respiration | Abnormal mitochondria Hypertrophic cardiomyopathy Cardiac fibrosis Neurodegeneration | Decrease survival, ataxia and cardiomyopathy | of interest (for example, FXN) is packaged in a viral capsid (e.g., AAV or bocavirus) or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the gene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

An effective amount of an rAAV or composition may be determined based on an animal model, rather than a human patient. Examples of a suitable murine or NHP model are described herein. In certain embodiments, the animal model suitable for assessing the effective amount is Fxn cardiac conditional (Fxn$^{flox/null}$::Ckmm-Cre), wherein the phenotype resembles the cardiac pathology of FRDA in humans. In certain embodiments, the animal model suitable for assessing the effective amount is Fxn neurological conditional (Fxn$^{flox/null}$::Pvalb-Cre) murine model, which exhibits exhibit similar neurodegeneration of DRG neurons and Purkinje cells accompanied by partial morphological abnormalities of mitochondria and impaired mitochondrial activity (Piguet, F et al., Rapid and complete Reversal of Sensory Ataxia by Gene Therapy in a novel Model of Freidrich Ataxia, Mol. Ther., 2018, 26(8):P1940-1952, epub May 10, 2018). In some embodiments, the assessment in cardiac conditional Fxn cKO mice comprises the efficacy of rAAV.FXN, administered via IV, on the onset of cardiac symptoms using echocardiograms and heart succinate dehydrogenase (SDH) activity. In some embodiments, the assessment in neurological conditional Fxn KO mice evaluates the efficacy of rAAV.FXN administered, via IV, on body weight, survival, neurological and neuromuscular function endpoints. In some embodiments, the assessment comprises survival, body weight, clinical signs, cardiac function, biomarkers (e.g., growth differentiation factor 15 (GDF-15)), transgene expression (e.g., in heart, brain, DRG, spinal cord), and histopathological assessments.

In some embodiments, rAAV.FXN is administered IV at doses of $1 \times 10^{11}$ to $1 \times 10^{11}$ GC/kg In some embodiments, rAAV.FXN is administered IDN at a dose of about $1.5 \times 10^{12}$ GC bilaterally, for a total dose of $1 \times 10^{11}$ to $3 \times 10^{12}$ GC/kg.

In certain embodiments, the rAAV.FXN is administered by a method of dual-route administration to a patient in a need thereof, wherein a dose is administered IV, and approximately a log (10×) lower dose is administered IDN. In some embodiments, the rAAV.FXN is administered to a patient of 16 years old or older, wherein the diagnosed onset of FRDA was at 14 years old or younger at a dose as determined from the above-described scaling studies in mice and NHPs. The patient population of 16 years old or older, and wherein FRDA onset is at 14 years old or younger, presents with both the neurological and cardiac manifestations of the disease, progresses at a faster rate, and are more homogeneous in their disease presentation than late-onset patients, making them the most appropriate population for whom a stabilizing, disease-modifying therapy is most beneficial. These patients also represent a population with high unmet need. The early-onset form of FRDA has a variable age of onset occurring between 10.5-15.5 years old (Harding, 1981; Filla et al., 1990; Dürr et al., 1996; Parkinson et al., 2013). The age of disease onset is correlated to severity of disease, with younger patients generally experiencing more severe symptoms and a faster rate of disease progression (Reetz et al., 2015).

In some embodiments, a treatment regimen for FRDA comprises of rAAV.FXN administered by a method of dual-route administration to a patient in a need thereof, wherein two stocks of rAAV.FXN are used and one of the rAAV.FXN includes a vector genome having one or more DRG-specific miR target sequences (as described above). In certain embodiments, a rAAV.FXN is delivered by IV, and a rAAV.FXN having a vector genome with one or more DRG-specific miR target sequences is delivered by IDN. In another embodiment, the rAAV.FXN having a vector genome with one or more DRG-specific miR target sequences is delivered IV, and another rAAV.FXN is delivered IDN. In certain embodiments, two different stocks of rAAV.FXN are utilized, which may have miR target sequences which are the same, or which differ from each other. In certain embodiments, the rAAV.FXN have different capsids.

Optionally, an immunosuppressive co-therapy may be included in the treatment of a subject in need. Such an immunomodulatory regimen may include, e.g., but are not limited to immunosuppressants such as, a glucocorticoid, steroids, antimetabolites, T-cell inhibitors, a macrolide (e.g., a rapamycin or rapalog), and cytostatic agents including an alkylating agent, an anti-metabolite, a cytotoxic antibiotic, an antibody, or an agent active on immunophilin. The immune suppressant may include a nitrogen mustard, nitrosourea, platinum compound, methotrexate, azathio-prine, mercaptopurine, fluorouracil, dactinomycin, an anthracycline, mitomycin C, bleomycin, mithramycin, IL-2 receptor-(CD25-) or CD3-directed antibodies, anti-IL-2 antibodies, cyclosporin, tacrolimus, sirolimus, IFN-0, IFN-γ, an opioid, or TNF-α (tumor necrosis factor-alpha) binding agent. In certain embodiments, the immunosuppressive therapy may be started prior to the gene therapy adminis-tration. Such therapy may involve co-administration of two or more drugs, the (e.g., prednelisone, micophenolate mofetil (MMF) and/or sirolimus (i.e., rapamycin)) on the same day. One or more of these drugs may be continued after gene therapy administration, at the same dose or an adjusted dose. Such therapy may be for about 1 week, about 15 days, about 30 days, about 45 days, 60 days, or longer, as needed.

Still other co-therapeutics may include, e.g., anti-IgG enzymes, which have been described as being useful for depleting anti-AAV antibodies (and thus may permit admin-istration to patients testing above a threshold level of anti-body for the selected AAV capsid), and/or delivery of anti-FcRN antibodies which is described, e.g., in U.S. Pro-visional Patent Application No. 63/040,381, filed Jun. 17, 2020, entitled "Compositions and Methods for Treatment of Gene Therapy Patients", and/or one or more of a) a steroid or combination of steroids and/or (b) an IgG-cleaving enzyme, (c) an inhibitor of Fc-IgE binding; (d) an inhibitor of Fc-IgM binding; (e) an inhibitor of Fc-IgA binding; and/or (f) gamma interferon.

IV. Apparatus and Method for Delivery of a Pharmaceutical Composition

In one aspect, the rAAV or composition provided herein may be administered intrathecally via the method and/or the device provided in this section and described in WO 2018/160582, which is incorporated by reference herein. Alter-natively, other devices and methods may be selected.

In certain embodiments, the method comprises the steps of CT-guided sub-occipital injection via spinal needle into the cisterna magna of a patient. As used herein, the term Computed Tomography (CT) refers to radiography in which a three-dimensional image of a body structure is constructed by computer from a series of plane cross-sectional images made along an axis.

On the day of treatment, the appropriate concentration of rAAV.FXN is be prepared. A syringe containing 5.6 mL of rAAV.FXN at the appropriate concentration is delivered to the procedure room. The following personnel are present for study drug administration: interventionalist performing the procedure; anesthesiologist and respiratory technician(s); nurses and physician assistants; CT (or operating room) technicians; site research coordinator. Prior to drug admin-istration, a lumbar puncture is performed to remove a predetermined volume of CSF and then to inject iodinated contrast intrathecally (IT) to aid in visualization of relevant anatomy of the cisterna magna. Intravenous (IV) contrast may be administered prior to or during needle insertion as an alternative to the intrathecal contrast. The decision to used IV or IT contrast is at the discretion of the interventionalist. The subject is anesthetized, intubated, and positioned on the procedure table. The injection site are prepped and draped using sterile technique. A spinal needle (22-25 G) are advanced into the cisterna magna under fluoroscopic guid-ance. A larger introducer needle may be used to assist with needle placement. After confirmation of needle placement, the extension set are attached to the spinal needle and allowed to fill with CSF. At the discretion of the interven-tionalist, a syringe containing contrast material may be connected to the extension set and a small amount injected to confirm needle placement in the cisterna magna. After the needle placement is confirmed by CT guidance +/–contrast injection, a syringe containing 5.6 mL of rAAV.FXN is connected to the extension set. The syringe contents are slowly injected over 1-2 minutes, delivering a volume of 5.0 mL. The needle is slowly removed from the subject.

In one aspect, the rAAV or composition provided herein may be administered via intraparenchymal (dentate nucleus) (IDN) route by a method and/or the device using Clear-Point® Neuro Navigation System and ventricular cannula. Alternatively, other devices and methods may be selected. In some embodiments, the rAAV or compositions are admin-istered via IDN to address neurological manifestation of FRDA.

In certain embodiments, the methods comprises using the ClearPoint® injection system wherein the system consists of a monitor to visualize the brain and injection procedure in real time, a head fixation frame that is secured to the skull, and an MRI-compatible SmartFrame® (MRI Interventions Inc., Memphis, TN) trajectory device that enables MRI-guided alignment during the procedure. This system allows for the direct injection to be combined with real-time visualization of the injection tract by MRI. To enable visu-alization of rAAV or composition distribution, the injection material containing the vector is mixed with gadolinium, which is contrast agent (final concentration of 1-2 mM gadolinium). During the direct injection procedure, the injection cannula is placed through the ClearPoint® frame to the correct position on the skull and the frame maintains the correct trajectory. The final position of the injection cannula is confirmed using real-time MRI images, and then the rAAV or composition is injected into the parenchyma of the deep cerebellar nuclei using convection-enhanced delivery. Each subject receives administration of the rAAV or com-position plus gadolinium in each dentate nucleus injected at a rate of 0.5 µL/min initially, and then at an increased rate of up to 5 µL/min based on clinician discretion during the procedure. The procedure takes approximately 5-6 hours and subjects are anesthetized for the duration of the proce-dure.

In certain embodiments, the rAAV or composition is administered intravenously (IV). In some embodiments, IV administration is by IV infusion into peripheral vein. In some embodiments, the IV infusion rate and/or time is determined from nonclinical NHP studies, as described herein. In some embodiments, the IV infusion is over no less than a 20-minute interval using a syringe infusion pump via an IV administration set. In some embodiments, the IV infusion is 20-minutes to 1-hour long. In some embodi-ments, the IV infusion is 1-hour or longer, as per discretion of investigator, wherein a lower infusion rate may be nec-essary. The IV infusion occurs no longer than 24 hours prior to the IDN procedure occurring the following day. In some embodiments, the IV administration allows for observations of acute hypersensitivity to the rAAV or composition. In some embodiments, the rAAV or composition is adminis-tered by IV to address cardiac manifestation of FRDA.

In certain embodiments, the rAAV or composition provided herein may be administered via a method of dual-route administration comprising intravenous (IV) and intraparenchymal (dentate gyrus) (IDN), as two sequential doses within 24 hours of one another. The dual route of administration target peripheral organs, i.e., cardiac myocytes (i.e., IV) and central organs, cerebellum and sensory DRG neurons (i.e., IDN). In some embodiments, the IDN administration is unilateral. In some embodiments, the IDN administration is bilateral. In some embodiments, the rAAV or composition is administered via unilateral and/or bilateral MRI guided direct injection into the deep cerebellar nuclei (DCN) via convection-enhanced delivery (CED). In some embodiments, the rAAV is administered at a dose of $3.0 \times 10^{13}$ GC/kg via IV and at a dose of $1.5 \times 10^{12}$ GC in 50 μL via IDN (bilaterally, total dose of $3.0 \times 10^{12}$ GC/kg). The volume of IV infusion is determined based on the dose level and the weight of the subject. In some embodiments, the rAAV or composition is administered via IV and IDN (i.e., dual-routes of administration) to address both cardiac and neurological manifestations of FRDA. In some embodiments, the rAAV or composition is delivered via dual-routes of administration, wherein the amount of vector delivered by IV to the amount of vector delivered by IDN is at the ratio of about 10 to about 1. In further embodiments, the ratio of vector delivered by IV to vector delivered by IDN comprises of ration of about 2:1 to about 8:1, or about 3:1 to about 5:1, and inclusive of the values in between.

In certain embodiments, the efficacy of dual routes of administration of a rAAV or a composition is determined through the following endpoints:

General:
  Survival
  Levels of frataxin expression in serum samples evaluated at 1-year rAAV or composition treatment
  Quality of Life (QoL) as assessed by a FRDA-specific patient reported outcome questionnaire currently being developed by the Friedreich's Ataxia Research Alliance at 2 years post-rAAV or composition treatment
Neurological Endpoints:
  mFARS assessment as compared to baseline score to measure overall disease state over time (FARS scale is an exam-based rating scale that assesses neurological function over 5 areas of disease involvement (bulbar, upper limb, lower limb, peripheral nervous system, and upright stability) (Subramony et al., 2005)).
  Fine motor skills assessment with a 9-hole peg test (9HPT) measuring if subject is able to perform in <5 minutes; or use a spoon dexterity test if subject is unable to complete the 9HPT,
  Ambulation assessment by a 25-foot walk test at 2 years post-rAAV or composition treatment
  Dysarthia assessment (e.g., via speech analysis software)
Cardiac Endpoints:
  Electrocardiogram changes
  Cardiac MRI assessment
  Absence of progression of cardiac symptoms, including ICD and heart failure hospitalization.
Additional or alternate routes of administration to the intrathecal method described herein include, for example, systemic, oral, intravenous, intraperitoneal, subcutaneous, or intramuscular administration.

In one embodiment, doses may be scaled by brain mass, which provides an approximation of the size of the CSF compartment. In a further embodiment, dose conversions are based on a brain mass of 0.4 g for an adult mouse, 90 g for a juvenile rhesus macaque, and 800 g for children 4-18 months of age. The following Table 2 provides illustrative doses for a murine MED study, NHP toxicology study, and equivalent human doses.

TABLE 2

Illustrative doses for study in mouse and NHP.

| Dose (GC/g brain mass) | Mouse (GC) | NHP (GC) | Human (GC) |
|---|---|---|---|
| $3.33 \times 10^{11}$ | $1.30 \times 10^{11}$ | $3.00 \times 10^{13}$ | $2.70 \times 10^{14}$ |
| $1.11 \times 10^{11}$ | $4.40 \times 10^{10}$ | $1.00 \times 10^{13}$ | $8.90 \times 10^{13}$ |
| $3.33 \times 10^{10}$ | $1.30 \times 10^{10}$ | $3.00 \times 10^{12}$ | $2.70 \times 10^{13}$ |
| $1.11 \times 10^{10}$ | $4.40 \times 10^{9}$ | — | $8.90 \times 10^{12}$ |

In certain embodiments, a rAAV.FXN is administered to a subject in a single dose. In certain embodiments, the concentration in GC is illustrated as GC per spinal tap. In certain embodiments, the concentration in CG is illustrated as GC per mL.

A co-therapy may be delivered with the rAAV.FXN compositions provided herein. Co-therapies such as described earlier in this application are incorporated herein by reference.

EXAMPLES

The following examples are illustrative only and are not intended to limit the present invention.

| Abbreviation | Description |
|---|---|
| A | Absorbance |
| aa | Amino Acids |
| AE | Adverse Events |
| AEX | Anion Exchange |
| AmpR | Ampicillin Resistance (gene) |
| AUC | Analytical Ultracentrifugation |
| BA | Chicken β-Actin |
| BAER | Brainstem Auditory Evoked Response |
| BBB | Blood-Brain Barrier |
| BCA | Bicinchoninic Acid |
| BMT | Bone Marrow Transplant |
| bp | Base Pairs |
| BSA | Bovine Serum Albumin |
| BSE | Bovine Spongiform Encephalopathy |
| BSID-III | Bayley Scales of Infant and Toddler Development, Third Edition |
| BWCB | Bacterial Working Cell Bank |
| cap | Capsid (gene) |
| cDNA | Complementary Deoxyribonucleic Acid |
| CFR | Code of Federal Regulations |
| CFU | Colony Forming Units |
| cGMP | Current Good Manufacturing Practice |
| Cho | Choline |
| CI | Chimeric Intron |
| CMC | Chemistry Manufacturing and Controls |
| CMO | Contract Manufacturing Organization |
| CMV IE | Cytomegalovirus Immediate-Early Enhancer |
| CNS | Central Nervous System |
| CPE | Cytopathic Effects |
| CRISPR-Cas9 | Clustered Regularly Interspaced Short Palindromic Repeats/CRISPR-Associated Protein 9 |
| CRL | Charles River Laboratories |
| CSF | Cerebrospinal Fluid |
| CT | Computed Tomography |
| ddPCR | Droplet Digital Polymerase Chain Reaction |
| DLS | Dynamic Light Scattering |
| DMEM | Dulbecco's Modified Eagle Medium |

-continued

| Abbreviation | Description |
| --- | --- |
| DNA | Deoxyribonucleic Acid |
| DO | Dissolved Oxygen |
| DP | Drug Product |
| DRG | Dorsal Root Ganglia |
| DS | Drug Substance |
| DSMB | Data and Safety Monitoring Board |
| DT-MRI | Diffusion-Tensor Magnetic Resonance Imaging |
| E1A | Early Region 1A (gene) |
| ECG | Electrocardiogram |
| EDTA | Ethylenediaminetetraacetic Acid |
| ELISA | Enzyme-Linked Immunosorbent Assay |
| ELISpot | Enzyme-Linked Immunospot |
| ERT | Enzyme Replacement Therapy |
| EU | Endotoxin Units |
| F | Female |
| FBS | Fetal Bovine Serum |
| FDP | Filled Drug Product |
| FFB | Final Formulation Buffer |
| FIH | First-in-Human |
| GC | Genome Copies |
| GFP | Green Fluorescent Protein |
| GLP | Good Laboratory Practice |
| GMP | Good Manufacturing Practice |
| GvHD | Graft Versus Host Disease |
| HCDNA | Host Cell Deoxyribonucleic Acid |
| HCP | Host Cell Protein |
| HD | High Dose |
| HEK293 | Human Embryonic Kidney 293 |
| ICH | International Council for Harmonisation |
| ICV | Intracerebroventricular |
| IDN | Intraparenchymal (dentate gyrus) |
| IFN-$\gamma$ | Interferon Gamma |
| IND | Investigational New Drug Application |
| IT | Intrathecally |
| ITFFB | Intrathecal Final Formulation Buffer |
| ITR | Inverted Terminal Repeat |
| IU | Infectious Unit |
| IV | Intravenous |
| KanR | Kanamycin Resistance (gene) |
| Lac | Lactate |
| LAL | Limulus Amoebocyte Lysate |
| LFTs | Liver Function Tests |
| LOD | Limit of Detection |
| LTFU | Long-Term Follow-Up |
| M | Male |
| MBR | Master Batch Record |
| MCB | Master Cell Bank |
| MD | Mid-dose |
| MED | Minimum Effective Dose |
| MRI | Magnetic Resonance Imaging |
| mRNA | Messenger Ribonucleic Acid |
| MRS | Magnetic Resonance Spectroscopy |
| MS | Mass Spectrometry |
| MTD | Maximum Tolerated Dose |
| N | Number of Subjects or Animals |
| N/A | Not Applicable |
| NAbs | Neutralizing Antibodies |
| NCV | Nerve Conduction Velocity |
| NGS | Next-Generation Sequencing |
| NHP | Non-Human Primate |
| NOAEL | No-Observed-Adverse-Effect Level |
| OL | Open-Label |
| PBS | Phosphate-Buffered Saline |
| PEI | Polyethylenimine |
| PES | Polyethersulfone |
| PI | Principal Investigator |
| POC | Proof-of-Concept |
| PolyA | Polyadenylation |
| QA | Quality Assurance |
| QC | Quality Control |
| qPCR | Quantitative Polymerase Chain Reaction |
| rAAV | Recombinant Adeno-Associated Virus |
| rcAAV | Replication-Competent Adeno-Associated Virus |
| rBG | Rabbit β-Globin |
| rDNA | Ribosomal Deoxyribonucleic Acid |
| rep | Replicase (gene) |
| RNA | Ribonucleic Acid |

-continued

| Abbreviation | Description |
| --- | --- |
| RPM | Revolutions Per Minute |
| SAE | Serious Adverse Events |
| SDS | Sodium Dodecyl Sulfate |
| SDS-PAGE | Sodium Dodecyl Sulfate Polyacrylamide Gel Electrophoresis |
| SMN | Survival Motor Neuron (gene) |
| SOP | Standard Operating Procedure |
| SRT | Safety Review Trigger |
| ssDNA | Single-Stranded Deoxyribonucleic Acid |
| TBD | To Be Determined |
| TCID$_{50}$ | 50% Tissue Culture Infective Dose |
| TE | Tris-EDTA |
| TFF | Tangential Flow Filtration |
| TSE | Transmissible Spongiform Encephalopathy |
| UPLC | Ultra-Performance Liquid Chromatography |
| US | United States |
| USP | United States Pharmacopeia |
| WCB | Working Cell Bank |
| WHO | World Health Organization |

Example 1—Recombinant AAVhu68.hFXN rAAVhu68.CB7.CL.hFXN.polyA (also rAAVhu68.hFXN) includes the coding sequence for human frataxin, regulatory element derived from the chicken P3-actin (BA) promoter and human cytomegalovirus immediate-early enhancer (CMV IE), chimeric intron consisting of a chicken BA splice donor and a rabbit P3-globin (rBG) splice acceptor element polyadenylation (PolyA) signal derived from the rBG gene, two inverted terminal repeat sequences (ITRs). Vectors are constructed from cis-plasmids containing a coding sequence for human FXN (SEQ ID NO: 3) expressed from the chicken beta actin promoter with a cytomegalovirus enhancer (CB7) flanked by AAV2 inverted terminal repeats. The vectors are packaged in an AAV serotype hu68 capsid (WO 2018/160582) by triple transfection of adherent HEK 293 cells and purified by iodixanol gradient centrifugation as previously described in Lock, M., et al. Rapid, Simple, and Versatile Manufacturing of Recombinant Adeno-Associated Viral Vectors at Scale. Human Gene Therapy 21, 1259-1271 (2010). More particularly, AAV.CB7.CI.hFXN is produced by triple plasmid transfection of HEK293 working cell bank (WCB) cells with the AAV cis plasmid (pENN.AAV.CB7.CI.hFXN), the AAV trans plasmid encoding the AAV2 rep and AAVhu68 cap genes (pAAV2/hu68.KanR), and the helper adenovirus plasmid (pAdAF6.KanR). The AAV hu68 capsid proteins are provided in SEQ ID NO: 5. The CB7.CI.hFXN packaged vector genome is provided in SEQ ID NO: 12, which is 2954 bases. SEQ ID NO: 12 comprises a shortened AAV2 ITR sequence of 130 base pairs, wherein external A element is deleted compared to the wild type ITR sequence, which is 145 base pairs. The shortened ITR sequence is reverted back to the wild type length of 145 base pairs during vector DNA amplification using the internal A element as a template, therefore producing a vector genome having a predicted size of 2984 bases.

More detailed, the cis plasmid contains the following vector genome sequence elements:

Inverted Terminal Repeat (ITR): The ITRs are identical, reverse complementary sequences derived from AAV2 (130 base pairs [bp], GenBank: NC_001401) that flank all components of the vector genome. The ITRs function as both the origin of vector DNA replication and the packaging signal for the vector genome when AAV and adenovirus helper functions are provided in trans. As such, the ITR sequences represent the only cis sequences required for vector genome replication and packaging.

Human Cytomegalovirus Immediate-Early Enhancer (CMV IE): This enhancer sequence obtained from human-derived CMV (382 bp, GenBank: K03104.1) increases expression of downstream transgenes;

Chicken D-Actin Promoter (BA): This ubiquitous promoter (281 bp, GenBank: X00182.1) was selected to drive transgene expression in any CNS cell type; Chimeric Intron (CI): The hybrid intron consists of a chicken 0-actin splice donor (973 bp, GenBank: X00182.1) and rabbit β-globin splice acceptor element. The intron is transcribed, but removed from the mature mRNA by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This feature in gene vectors intended for increased levels of gene expression;

Coding sequence: The engineered cDNA of the human FXN gene encodes human frataxin protein, which is located in mitochondria and plays a role in iron biosynthesis and chaperon (630 bp; 210 amino acids [aa], GenBank: NP_000135); and Rabbit β-Globin Polyadenylation Signal (rBG PolyA): The rBG PolyA signal (127 bp, GenBank: V00882.1) facilitates efficient polyadenylation of the transgene mRNA in cis. This element functions as a signal for transcriptional termination, a specific cleavage event at the 3' end of the nascent transcript and the addition of a long polyadenyl tail.

Alternatively, the manufacturing process for rAAvhu68.hFXN involves transient transfection of human embryonic kidney 293 (HEK293) cells with plasmid DNA. The HEK293 master cell bank (MCB) used in the production has been tested and qualified as detailed in FDA and International Council for Harmonization (ICH) guidelines. To support clinical development, a single batch or multiple batches of the bulk drug substance (BDS) is produced by polyethylenimine-(PEI-) mediated triple transfection of HEK293 cells in bioreactors. Harvested AAV material is purified sequentially by clarification, tangential flow filtration (TFF), affinity chromatography, and anion exchange chromatography in disposable, closed bioprocessing systems where possible. The rAAVhu68.hFXN which are used for both the IV and IDN administrations are formulated in Intrathecal Final Formulation Buffer (ITFFB): 1 mM sodium phosphate, pH 7.2, 150 mM NaCl, 3 mM KCl, 1.4 mM $CaCl_2$), 0.8 mM $MgCl_2$, 0.001% Poloxamer 188. The rAAVhu68.hFXN is manufactured from BDS batch or batches that is frozen, subsequently thawed, pooled if necessary, adjusted to the target concentration, and sterile-filtered through a 0.2 μm filter, and filled into vials.

Additionally, a controlled bioreactor platform is implemented: where small-scale bioreactor is a linearly scaled with the respect of the cell growth surface to the large-scale bioreactor. The use of the small-scale bioreactor and the large-scale bioreactor allows for scalable manufacturing with minimal process and material impact. The large-scale bioreactor and/or the small-scale bioreactor are utilized for the production of the toxicology lot(s). The large-scale bioreactor is used for the production of the good manufacturing practice (GMP) drug substance (DS) lot(s). Large-scale GMP production batch sizes are be generated with multiple batches planned and pooled, if necessary, to satisfy the needed vector amount for drug product (DP) supply. When transferring manufacturing to the CMO for clinical use, the critical quality attributes are anticipated to not be modified. Critical source materials remains the same, including the MCB and source of the Fetal Bovine Serum (FBS)

although the PEI and plasmid DNA utilized for GMP manufacturing is produced in a manner that is designed to meet the requirements for current good manufacturing practice (cGMP) intermediates.

As the scale-up manufacturing process to the large-scale bioreactor is implemented and further optimized, and based on the combined manufacturing experience in the current bioreactor platform any potential impact related to changes in the process through comparability testing to ensure there is no change to identity, purity, potency, and safety of the product are addressed. The comparability testing that is conducted to compare a new lot manufactured with an updated procedure or with new material to a previous lot consists of a subset of tests included in the certificate of analysis (COA).

Example 2—rAAVhu68.hFXN delivery in Mouse Models of Friedreich's Ataxia Fxn cKO Mouse Studies (Cardiac conditional Fxn Mouse model)

A. Natural History Study in the Cardiac Conditional Fxn Knockout Mouse (Fxn cKO)(Nonclinical Study 1)

The activity of a rAAV.hFXN via intravenous administration has been evaluated in a murine model of FRDA cardiomyopathy.

The purpose of this non-GLP-compliant natural history study (Nonclinical Study 1) was to establish the natural disease progression of the Fxn cKO mouse model ($Fxn^{flox/null}$::Ckmm-Cre). Thirteen newborn (PND 0) mice were enrolled in the study, including Fxn cKO mice ($Fxn^{flox/null}$::Ckmm-Cre) displaying the disease phenotype and Fxn unaffected control littermates ($Fxn^{flox/null}$). Weekly body weights were recorded, and animals euthanized upon reaching a humane endpoint defined by weight loss >20% of maximal body weight. Survival was recorded.

Body weight of untreated Fxn cKO mice peaked at 18.6 g by 60 days of age (8 weeks of age), after which, the mice started to lose weight until they reached a humane endpoint (FIG. 2A). This study confirmed previous reports in the Fxn cKO mice regarding initial body weight loss by 9 weeks of age (~63 days of age) and a mean survival of 89 days of age.

B. Study in Cardiac Conditional Fxn Knockout Mice (Nonclinical Study 2)

The objective of this non-GLP-compliant pilot POC study was to determine the survival of Fxn cKO mice ($Fxn^{flox/null}$i::Ckmm-Cre) following IV administration of rAAVhu68.hFXN. Adult (31-34 days of age) Fxn cKO mice were administered rAAVhu68.hFXN at an IV dose of 2.0× $10^{11}$ GC. The dose was selected based on experience with similar AAV therapies where this dose was found to be non-toxic and lead to efficacy. The age (31-34 days of age) was selected to increase the likelihood of observing disease rescue and mirrors the intended clinical trial population. Weekly body weights were recorded. Animals were euthanized upon reaching a humane endpoint defined by weight loss ≥20% of maximal body weight, and survival was recorded. At the time of euthanasia, blood was collected for GDP-15, a measurement of cardiac stress, analysis via an ELISA assay. IV administration of rAAVhu68.hFXN, delayed body weight loss and extended survival to 140 days compared to 89 days in the untreated controls in the natural history study (Nonclinical Study 1).

Fxn cKO mice administered rAAVhu68.hFXN gained weight during the study and had comparable body weight to Fxn unaffected control mice until 120 days of age (17 weeks of age; FIG. 2A). Average weights for the Fxn cKO treated mice was 22.6 g and Fxn unaffected control mice was 21.98 g (Nonclinical Study 1). Fxn cKO mice administered rAAVhu68.hFXN began to loss weight after 120 days of age with the weight loss continuing until 150 days of age (21 weeks of age) when all mice reached humane endpoint criteria.

Figure 3:
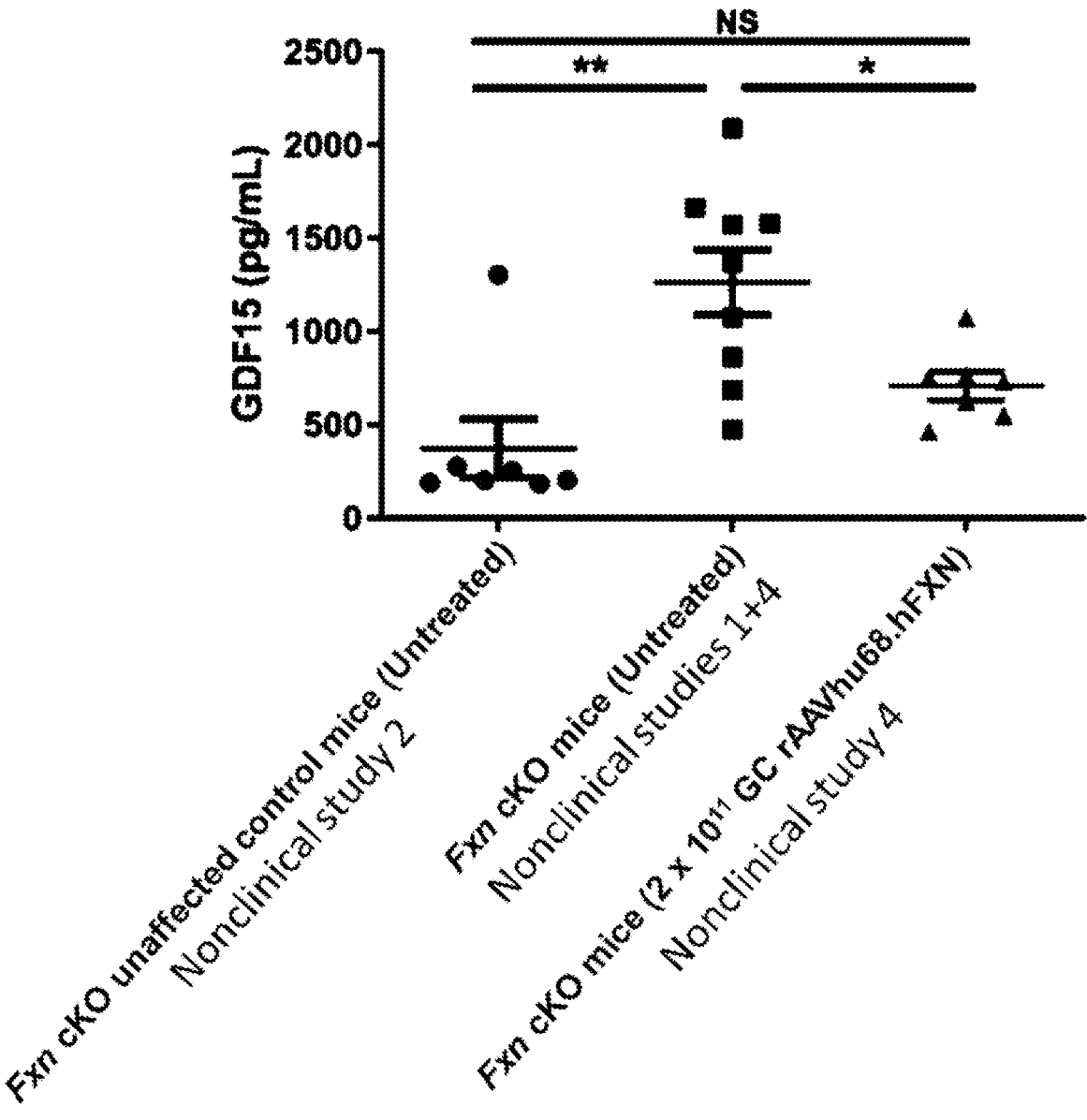
FIG. 3 provides the GDF-15 levels in the serum following IV administration of rAAVhu68.hFXN in FA mouse model. At 30 days of age Fxn cKO mice were IV-administered rAAVhu68.hFXN at a dose of $2.0×10^{11}$ GC. Age-matched Fxn cKO mice and Fxn unaffected control mice remained untreated and served as controls. Blood was collected at necropsy when mice reached the humane euthanasia criteria. **p=0.001 and * p=0.45 based on a statistical analysis using a one-way ANOVA followed by Tukey's. Abbreviations: ANOVA, analysis of variance; Fxn, frataxin (gene, mouse); GC, genome copies; Fxn cKO, cardiac conditional knockout affected mice (Fxn$^{flox/null}$::Ckmm-Cre); Fxn unaffected control mice (Fxn$^{flox/null}$).

FIG. 2A provides the results of a pilot cardiac gene therapy study (Nonclinical Study 1 and 2) in a Fxn$^{flox/null}$::Ckmm-Cre FA mouse model. FIG. 2A provides a graph of body weight (grams ±SEM) over time (0-20 weeks). The triangles represent Fxn$^{flox/null}$::Ckmm-Cre rAAVhu68.hFXN ($2\times10^{11}$ genome copies (GC) intravenous (iv) at 5 weeks (n=7). The circles represent results in Ckmm-cre; fxn-/flox (n=7). The squares represent Ckmm-cre; fxn-/flox (n=7). At 30 days of age Fxn cKO mice were IV-administered rAAVhu68.hFXN at a dose of $2.0\times10^{11}$ GC (Nonclinical Study 2). Age-matched Fxn cKO mice and Fxn unaffected mice remained untreated and served as controls (Nonclinical Study 1). rAAVhu68.hFXN IV administration to Fxn cKO mice reduced GDF-15 serum levels indicating normalization of cardiac stress (FIG. 3).

These data demonstrated that the administration of rAAVhu68.hFXN to cFxn cKO mice resulted in delayed weight loss, improved survival, and normalization of GDF-15 levels.

C. Survival Study in Cardiac Conditional Fxn Knockout Mice (Nonclinical Study 3)

This non-GLP-compliant study evaluated if a higher IV dose of rAAVhu68.hFXN could further extend survival in Fxn cKO (Fxn$^{flox/null}$::Ckmm-Cre) mice. Fxn cKO mice (26-29 days of age) were administered rAAVhu68.hFXN IV at a dose of $5.0\times10^{11}$ GC. The IV dose was selected based on experience with similar AAV therapies where this dose was found to be non-toxic but was efficacious. Treatment at 26-29 days of age was selected to increase the likelihood of observing disease rescue and mirrors the intended early adulthood population for the clinical trial. Animals were euthanized upon reaching a humane endpoint (defined by weight loss), and survival was recorded. IV administration of rAAVhu68.hFXN extended survival to 196 days compared to 140 days for $2.0\times10^{11}$ GC GTP-212 treated mice (Nonclinical Study 2).

This study demonstrated that increasing the of rAAVhu68.hFXN could further increase survival in Fxn cKO mice.

D. Pharmacology Study in Cardiac Conditional Fxn Knockout mice (Nonclinical Study 4)

The purpose of this non-GLP-compliant study was to evaluate the efficacy of rAAVhu68.hFXN administered IV in the Fxn cKO (Fxn$^{flox/null}$::Ckmm-Cre) mouse model. Adult (30 days of age) Fxn cKO mice were administered rAAVhu68.hFXN at a dose of $2.0\times10^{11}$ GC. Age-matched control animals included, untreated Fxn cKO and untreated Fxn unaffected control (Fxn$^{flox/null}$) mice. At the time of euthanasia (80 days of age), the heart was harvested for assessment of iron accumulation and blood was collected for GDF-15, a measurement of cardiac stress, analysis using an ELISA assay.

Figure 2B:
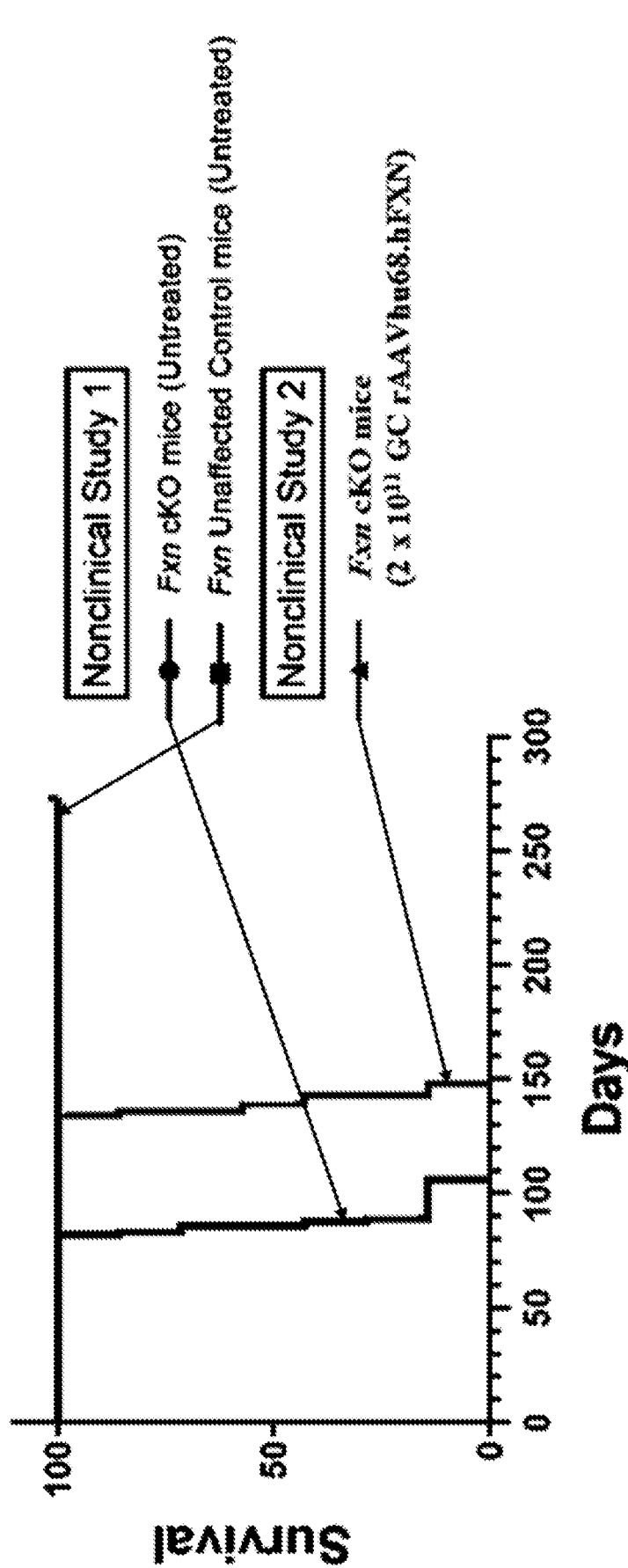

Administration of rAAVhu68.hFXN led to an increase in survival of Fxn cKO mice compared to untreated Fxn cKO mice. Untreated FXN cKO mice had an average life span of 89 days, FXN cKO mice treated with 2e13 GC hu68.hFXN had an average life span of 140 days. The 2e11 GC treated mouse that survived the longest reached 148 days of age. (FIG. 2B). Fxn unaffected control mice survived to 273 days of age when the study was terminated.

rAAVhu68.hFXN administration to Fxn cKO mice reduced GDF-15 circulating serum levels to untreated Fxn unaffected control mice levels (FIG. 3). The reduction indicates normalization of cardiac stress. Circulating GDF-15 levels in the serum were increased in untreated Fxn cKO mice compared to untreated Fxn unaffected control mice.

rAAVhu68.hFXN administered IV at a dose of $2.0\times10^{11}$ GC to Fxn cKO mice resulted in delayed body weight loss through 120 days of age (17 weeks of age), increased survival to 148 days of age, and normalized serum levels of GDF-15.

E. Study in Cardiac Conditional Fxn Knockout Mice

The objectives of this non-GLP-compliant study are to: 1) establish when cardiac symptoms begin to manifest in the Fxn cKO mice (Fxn$^{flox/null}$::Ckmm-Cre); and 2) to determine the efficacy of IV administration of rAAVhu68.hFXN to correct cardiac pathology without leading to cardiomyopathy. For the first study objective, adult Fxn cKO mice (Fxn$^{flox/null}$::Ckmm-Cre) (Group 5) and Fxn unaffected Cre mice (Fxn$^{flox/null}$::Ckmm-Cre; Group 6) are enrolled in the study when they are 21 days of age (Table 4). Echocardiogram is performed when mice are 28 days of age to assess hypertrophic cardiomyopathy. Hypertrophic cardiomyopathy such as cardiac output, left ventricle mass, end-systolic dimension, and shortening fraction has been previously reported (Belbellaa et al., 2019). After echocardiograms at 28 days of age mice are necropsied and hearts harvested for histopathological assessment of cardiac pathology, such as fibrosis, and a disease-relevant biomarker, SDH (mitochondrial respiratory complex II) activity.

For the second study objective, adult Fxn cKO mice that are 21 or 28 days of age are IV administered rAAVhu68.hFXN at a dose $3\times10^{13}$ GC/kg or vehicle (Table 4). Age-matched Fxn cKO and Fxn unaffected Cre mice are administered vehicle at 21 days of age as controls. Body weights and blood are collected during the study to evaluate circulating levels of GDF-15, a cardiac stress marker. At 70 days of age all mice have echocardiogram assessments to assess hypertrophic cardiomyopathy and then necropsied and hearts harvested for histopathological assessment of cardiac pathology and changes in SDH activity. Comparison of these parameters are used to assess the efficacy of GTP-212 treatment on cardiac pathology of different ages where there is the possibility of overexpression of frataxin.

TABLE 4

| | Group Designations. | | | | | |
| --- | --- | --- | --- | --- | --- | --- |
| Group | Study Objective 2 | | | | Study Objective 1 | |
| Number | 1 | 2 | 3 | 4 | 5 | 6 |
| Animals age at enrollment | 21 (±2) days | 21 (±2) days | 21 (±2) days | 21 (±2) days | 21 (±2) days | 21 (±2) days |
| Genotype | Fxn cKO | Fxn cKO | Fxn cKO | Fxn unaffected controls | Fxn cKO | Fxn unaffected controls |

TABLE 4-continued

| | Group Designations. | | | | | |
|---|---|---|---|---|---|---|
| Group | | Study Objective 2 | | | Study Objective 1 | |
| Number | 1 | 2 | 3 | 4 | 5 | 6 |
| Treatment | rAAVhu68.hFXN | rAAVhu68.hFXN | Vehicle (PBS) | Vehicle (PBS) | Untreated | Untreated |
| ROA | IV | IV | IV | IV | NA | NA |
| Administration Day | 21 (±2) days old | 28 (±2) days old | 21 (±2) days old | 21 (±2) days old | NA | NA |
| Dose (GC/kg) | $3 \times 10^{13}$ | $3 \times 10^{13}$ | NA | NA | NA | NA |
| Necropsy Day | 70 (±5) days of age | 70 (±5) days of age | 70 (±5) days of age | 70 (±5) days of age | 28 (±4) days of age | 28 (±4) days of age |
| N | 8 | 8 | 8 | 8 | 8 | 8 |

Abbreviations:
Fxn, frataxin (gene, mouse);
GC, genome copies;
Fxn cKO, cardiac conditional knockout affected mice (Fxn$^{flox/null}$::Ckmm-Cre);
Fxn unaffected controls (Fxn$^{flox/null}$);
GC, genome copies;
IV, intravenous,
N, number of animals;
NA, not applicable;
PBS, phosphate buffered saline;
ROA, route of administration.

F. Survival Study in Neurological Conditional Fxn Knock-out Mice (Fxn ncKO) (Nonclinical Study 6)

The purpose of this non-GLP-compliant study is to determine the efficacy of IV administration rAAVhu68.hFXN on survival and ataxic behavior in the Fxn ncKO mouse model. Fxn ncKO mice (Fxn$^{flox/null}$:Pvalb-Cre) 31 days of age are administered rAAVhu68.hFXN IV at a dose of $3.0 \times 10^{13}$ GC/kg GC or vehicle (PBS). Age-matched wild type mice are also be IV administered vehicle (PBS) as a control. The dose of rAAVhu68.hFXN was selected based on robust heart and DRG transduction observed in Nonclinical Study 7 (data not shown). Body weights are assessed weekly throughout the study. Neurological assessment (Neuroscore) is performed at baseline and weekly thereafter (Table 5). Briefly, mice are suspended by the tail to assess collapse of leg extension towards the lateral midline. Mice are then placed in a cage where the other ataxic phenotype are assessed.

Neuromotor function (rotarod) is performed at 56 days of age and every 4 weeks. Briefly, mice are habituated to the RotaRod then testing trials are performed to measure how long each mouse can remain on the rotating rod while it is accelerating. For each animal, the testing trial is considered terminated when the mouse falls off the rod, completes two passive revolutions, or 300 seconds elapses. The fall latency (defined as the time between the initiation of rod acceleration and trial termination) is then recorded. A total of three sequential test replicates are performed for the mice in each trial, with a 2 minute pause between runs to allow the animals to rest in the collecting box.

All assessments are performed until the mice reach the humane euthanasia endpoint which is defined by weight loss >20% of maximal body weight or a Neuroscore of 4.

TABLE 5

| Neuroscore Assessment | |
|---|---|
| Observation | Score |
| Mouse walking/behaving normally. Full extension of hind legs away from lateral midline when mouse is suspended by its tail, and mouse can hold this for 2 seconds, suspended 2-3 times. | 0 |
| Collapse or partial collapse of leg extension towards lateral midline (weakness) or trembling of hind legs during suspension. Possible minor head bobble behavior. | 1 |
| Toes curl under at least twice during walking of 12 inches, or any part of foot is dragging along cage bottom/table, walk is slightly wobbly, feet wider apart, occasionally throws out a leg to catch itself, or has "high-stepping" behavior, occasional stargazing behavior. | 2 |
| Staggering or erratic walk, occasional circling behavior frequent stargazing, loss of spatial sense or potential vision loss (running into cage-mates or walls), belly occasionally drags on ground, loss of balance. | 3 |
| Endpoint phenotype. Mouse frequently falls over, cannot control back limbs, belly frequently on ground, head and tail move erratically to keep balance. | 4 |

Assessments are based on scoring developed at Jackson Laboratories, (www.jax.org/) during characterization of the Fxn ncKO mouse model.

Example 3—rAAVhu68.hFXN Delivery in Nonhuman Primates

A. IV Dose Ranging Pharmacology, Biodistribution, and Safety Study in Non-Human Primates (Nonclinical Study 7)

The purpose of this non-GLP-compliant study was to determine the pharmacokinetic, safety profile and transduction efficiency of cardiomyocytes, DRG sensory neurons and region of interest in the CNS (dentate nucleus), following IV administration of rAAVhu68.hFXN. NHPs were selected for this study as they replicate the CNS, PNS, and heart anatomy of the intended FDRA patient population. Adult NHPs (3-6 years old) were administered one of three doses of rAAVhu68.hFXN, $1.0\times10^{13}$ GC/kg, $3.0\times10^{13}$ GC/kg, or $1.0\times10^{14}$ GC/kg. Age-matched NHPs were untreated and served as a control. In-life evaluations included daily clinical observations, physical exams, body weights, clinical pathology of the blood. Animals were necropsied 28 days post administration and a comprehensive list of tissues were harvested for histological evaluation and biodistribution.

Histopathological examination was performed for the liver, heart, spinal cord, and DRG sensory neurons. Transgene expression was evaluated for the heart and DRG sensory neurons by in-situ hybridization (ISH) and further validated in the heart by immunohistochemistry (IHC).

rAAVhu68.hFXN related pathological findings included mild hepatocellular loss and individual cell apoptosis in portal areas with moderate chronic inflammation and secondary hepatic changes including minimal hepatocellular regeneration, bile duct hyperplasia and portal fibrosis. These findings were observed in NHPs administered the highest dose, $1.0\times10^{14}$ GC/kg (1/2 animals). These liver findings, albeit more severe, have been reported in the literature associated with high dose IV AAV9 and AAV9-like vector administration with different transgenes and are likely not related to rAAVhu68.hFXN administration (Hinderer et al., 2018). Minimal myocardial infiltrates were observed in the heart in the majority of rAAVhu68.hFXN-treated NHPs. This finding has been reported as background findings in NHPs and are not considered rAAVhu68.hFXN treatment-related (Sato et al., 2012). No histopathological findings were observed in the DRG in any of the rAAVhu68.hFXN treated groups.

Dose-dependent transduction of the heart was observed in all rAAVhu68.hFXN treatment NHPs. Robust transgene expression in cardiomyocytes of the heart (data not shown) and DRG sensory neurons (data not shown) was observed in NHPs treated with doses of $3.0\times10^{13}$ GC/kg and $1.0\times10^{14}$ GC/kg. IHC staining revealed minimal transgene expression in the dentate nucleus and upper motor neurons (data not shown).

In Nonclinical study 7, safety and transduction efficiency of the heart and DRG was assessed after IV administration of rAAVhu68.hFXN at a dose of $1.0\times10^{13}$ GC/kg, $3.0\times10^{13}$ GC/kg, and $1.0\times10^{14}$ GC/kg. Higher doses were not evaluated due to of risk of systemic toxicity in higher doses such as $2.0\times10^{14}$ GC/kg (Hinderer et al., 2018). The study duration was 28 days, allowing peak transgene expression to be achieved. However systemic administration has poor transduction profile of deep brain regions such as the dentate nucleus, which is an important area leading to FRDA neuropathology. Nonclinical study 8 assessed the safety and transduction efficiency of unilaterally and bilaterally MRI-guided direct injection of rAAVhu68.hFXN into the deep cerebellar nuclei (DCN) via convection-enhanced delivery (CED) in two adult NHPs. The dose was chosen to ensure high transduction and assess the safety of introducing high levels of the transgene into the dentate nucleus. Due to the achieved transgene expression in Nonclinical Study 7 and results from Nonclinical Study 8, the toxicology studies includes both IV administration of rAAVhu68.hFXN (Nonclinical Study 11) and the dual ROA (Nonclinical Study 12). The IV dose(s) were chosen based on robust transgene expression of frataxin in the heart (Nonclinical Study 7) and the IDN dose chosen based on robust transgene expression in the dentate nucleus (Nonclinical Study 8). Study duration of the toxicology studies (Nonclinical Study 11 and Nonclinical Study 12) are 120 days to allow for a comprehensive assessment of safety and transgene expression in target organs.

rAAVhu68.hFXN at doses of $3.0\times10^{13}$ GC/kg and $1.0\times10^{14}$ GC/kg administered IV to NHPs lead to transduce of cardiomyocytes and DRG sensory neurons providing evidence for the potential of rAAVhu68.hFXN treatment to impact cardiac and PNS disease affected in FRDA patients. Minimal transduction of the dentate nucleus and upper motor neurons were observed suggesting IV administration of rAAVhu68.hFXN may not be the optimal ROA to target CNS tissues.

B. Distribution of AAV Serotype hu68 Vector in the Non-Human Primates (NHP) Dentate Nucleus of the Cerebellum (Nonclinical Study 8)

The purpose of this non-GLP-compliant study was to assess the safety and distribution of unilaterally and bilaterally MRI-guided direct injection of rAAVhu68.hFXN into the deep cerebellar nuclei (DCN) via convection-enhanced delivery (CED) in two adult (5-10 years old) NHPs. The devices used for DCN delivery is the same as in the Phase 1/2 FIH clinical trial (ClearPoint® System). The first animal was administered rAAVhu68.hFXN at a total dose of $1.71\times10^{13}$ GC with a contrast agent (2 mM ProHance®, Gadoteridol) in a volume of 200 µl via a single (unilateral) transfrontal trajectory through the left hemisphere that targeted the middle of the DCN. The second animal was administered rAAVhu68.hFXN at a dose of $8.56\times10^{12}$ GC with a contrast agent (2 mM ProHance®, Gadoteridol) in a volume of 100 µl per site via two (bilateral) transfrontal trajectories (one per hemisphere) that targeted the left and right DCN. In both animals, a cannula was first inserted into the brain directing the injection of rAAVhu68.hFXN into the DCN which was confirmed via hyperintense signal on magnetic resonance imaging (MRI) emitted by the contrast agent (ProHance®, Gadoteridol). In-life evaluations included daily cage side observations of animal health and neurological symptoms. Animals were necropsied 30 days post administration and the body was transcardially perfused with cold phosphate buffered saline (PBS) with 0.026% (2.64 IU/mL) heparin. The entire brain was harvested, placed in a brain matrix and coronally sliced into 9-mm blocks. Coronal blocks were transferred into buffered formalin and processed for histology. Representative samples of brain (complete), liver, spleen, kidneys, lung, CSF, heart, testes, spinal cord (sections of cervical, thoracic and lumbar) were harvested and transferred into buffered formalin. Histopathological evaluation was performed on the brain and spinal cord and transgene expression in the brain evaluated by ISH.

The majority of microscopic findings in the forebrain, thalamus and medulla were considered likely procedural related as these findings were typically small discrete foci consistent with linear tracts (i.e. cannula/needle tract) resulting from direct injection into the brain. The microscopic findings included minimal to mild infiltrates of gitter cells along with other glial cells. There was no microscopic evidence of neuronal degeneration or necrosis. Cerebellar histopathology demonstrated minimal gliosis and parenchymal loss. Cerebellar findings consisted of multifocal to regional gliosis with or without reactive astrocytosis and perivascular mononuclear cell infiltrates with occasional perivascular edema. There were variably-sized discrete regions composed of gitter cells, similarly representing neural tissue injury likely secondary to DCN injection; however, there was no evidence of neuronal degeneration or necrosis. The surrounding affected white matter tracts exhibited similar axonal damage as described above. Given that this was the target site of the injection, it was not unexpected that the microscopic findings were slightly more severe. For the most part these findings were considered likely proce-
dural related to the injection; however, test article associated
perivascular mononuclear cells and edema, which were
restricted to the DCN (target site), cannot be ruled out. The
animals were behaviorally normal throughout the study with
no associated neurologic deficits. Transgene expression in
both animals was confined to the cerebellum (data not
shown), with the most robust transgene expression occurring
following bilateral IDN injections of rAAVhu68.hFXN (data
not shown).

Robust and local transduction of the dentate nucleus with
no dose limiting toxicity was observed following unilateral
and bilateral IDN administration of rAAVhu68.hFXN lead-
ing the possibility to impact the neurological symptoms in
FRDA patient.

Example 4—Pharmacology and Toxicology Studies
with rAAVhu68.hFXN

A. Efficacy of rAAVhu68.hFXN Following Intravenous
Administration in Cardiac Conditional Knockout Fxn Mice
to Determine the Minimum Effective Dose (MED) (Non-
clinical Study 9)

This study evaluates the efficacy and determine the MED
of rAAVhu68.hFXN following IV administration to Fxn
cKO mice (Fxn$^{flox/null}$::Ckmm-Cre). The study is conducted
per GLP regulations or with Quality Assurance (QA) over-
sight (conduct per protocol and oversight of key phases of
the study and final report). Adult Fxn cKO mice (28 days
old) receive a single IV administration of rAAVhu68.hFXN
at one of four dose levels, $3.0\times10^{12}$ GC/kg, $1.0\times10^{13}$ GC/kg,
$3.0\times10^{13}$ GC/kg, or $1.0\times10^{14}$ GC/kg. Age-matched Fxn cKO
and Fxn unaffected Cre mice (Fxn$^{flox/null}$::Ckmm-Cre) are
administered vehicle (PBS) as controls. The age of the
animals was selected to mimic the proposed clinical trial
population. The selected doses are based on results from
Nonclinical Study 2 and Nonclinical Study 3. In-life assess-
ments include daily viability checks when animal are 7
weeks of age (~49 days of age), weekly body weight
measurements, and survival. Mice are necropsied 120 days
after administration or when animals reach the prespecified
euthanasia endpoint (determined by veterinarian or by 20%
weight loss from maximal weight). At necropsy, blood are
collected for complete blood counts (CBCs) and serum
clinical chemistries as toxicology readouts, and for mea-
surement of cardiac stress marker (GDF-15) as pharmacol-
ogy endpoint. A complete tissue list are harvested for
comprehensive histopathology evaluation. Heart tissue are
harvested to evaluate disease-relevant biomarker of mitochondrial function (SDH Activity) and cardiomyocyte trans-
duction are quantified by ISH or IHC.
B. Efficacy of rAAVhu68.hFXN Following Intravenous
Administration in Neurological Conditional Knockout Fxn
Mice to Determine the Minimum Effective Dose (MED)
(Nonclinical Study 10)

This study evaluates the efficacy and determine the MED
of rAAVhu68.hFXN following IV administration to Fxn
ncKO mice. The study is conducted per GLP regulations or
with QA oversight (conducted per protocol and oversight of
key phases of the study and final report). Adult Fxn ncKO
mice (28 days old) receive a single IV administration of
rAAVhu68.hFXN at one of four dose levels, $3.0\times10^{12}$
GC/kg, $1.0\times10^{13}$ GC/kg, $3.0\times10^{13}$ GC/kg, $1.0\times10^{14}$ GC/kg,
or vehicle (PBS). Age-matched Fxn unaffected mice are
administered vehicle (PBS) as a control. The age of the
animals was selected to mimic the proposed clinical trial
population. The selected doses are based on results from
Nonclinical Study 6 and Nonclinical Study 3. In-life assess-
ments include daily viability checks, weekly neurological
assessment (Neuroscore, See Nonclinical Study 6 and Table
5 for details of the assessment), and body weight measure-
ments, monthly neuromotor function (RotaRod, See Non-
clinical Study 6 for details of the assessment) starting at 56
days of age (8 weeks of age) and survival. Mice are
necropsied 120 days after administration or when animals
reach the prespecified euthanasia endpoint (determined by
veterinarian when mice reach 20% weight loss from maxi-
mal weight or a Neuroscore of 4). At necropsy, blood is
collected for complete blood counts (CBCs) and serum
clinical chemistries and tissues are harvested for compre-
hensive histopathology evaluation.
C. Toxicology of rAAVhu68.hFXN Administered Intrave-
nous in Adult Rhesus Macaques (Nonclinical Study 11)

A 120 day GLP-compliant safety study is conducted in
adult rhesus macaques (3-8 years of age) to investigate the
toxicology of rAAVhu68.hFXN following IV administra-
tion. Rhesus macaques receive one of three dose levels of
rAAVhu68.hFXN: $1.0\times10^{13}$ GC/kg, $3.0\times10^{13}$ GC/kg, or
$1.0\times10^{14}$ GC/kg (Table 6). Additional adult NHPs are
administered vehicle, intrathecal final formulation buffer
(ITFFB) as a control. The rAAVhu68.hFXN dose levels
selected are equivalent to three highest doses that are
evaluated in the MED studies (Nonclinical Study 9 and
Nonclinical Study 10). The 120 day evaluation period was
selected to allow sufficient time for a transgene product to
reach stable plateau levels following IV AAV administra-
tion. The age of administration was selected to be represen-
tative of the proposed clinical trial population in terms of
anatomy.

TABLE 6

Rhesus Macaque GLP Toxicology Study.

| | Group Designation | | | |
|---|---|---|---|---|
| | 1 | 2 | 3 | 4 |
| Number of Macaques | 2 | 3 | 3 | 3 |
| Sex | M + F | M + F | M + F | M + F |
| Age | Adult (3-8 years) | Adult (3-6 years) | Adult (3-6 years) | Adult (3-6 years) |
| Test Article | Vehicle (PBS) | rAAVhu68.hFXN | rAAVhu68.hFXN | rAAVhu68.hFXN |
| ROA | IV | IV | IV | IV |
| Vector Dose | NA | $1.0\times10^{13}$ GC/kg | $3.0\times10^{13}$ GC/kg | $1.0\times10^{14}$ GC/kg |
| Necropsy Day | 120 | 120 | 120 | 120 |

Abbreviations: F, female; GC, genome copies; GLP, good laboratory practice; ITFFB, intrathecal final formulation buffer; IV, intravenous; M, male; NA, not applicable; ROA, route of administration.

Baseline neurologic examinations, clinical pathology (cell counts with differentials, clinical chemistries, and a coagulation panel), CSF chemistry, and CSF cytology are performed. After rAAVhu68.hFXN or vehicle administration, the animals are monitored daily for signs of distress and abnormal behavior. Neurological assessments are divided into five sections evaluating the following: mentation, posture and gait, proprioception, cranial nerves, and spinal reflexes. The tests for each assessment are performed in the same order each time. Assessors are not formally blinded to the treatment group; however, assessors typically remain unaware of treatment group at the time of assessment. Numerical scores are given for each assessment category as applicable and are recorded (normal: 1; abnormal: 2; decreased: 3; increased: 4; none: 5; N/A: not applicable).

Blood and CSF clinical pathology assessments and neurologic examinations are performed on a weekly basis for 30 days following rAAVhu68.hFXN or vehicle administration, and every 30 days thereafter. Additional blood clinical pathology assessment are performed 3 days after administration. At baseline, study days 0, 30 and 120, anti-AAVhu68 NAbs and cytotoxic T lymphocyte (CTL) responses to AAVhu68 and the rAAVhu68.hFXN transgene product are assessed by an interferon gamma (IFN-γ) enzyme-linked immunospot (ELISpot) assay. Nerve conduction velocity (NCV) assessment is performed at baseline, study days 14, 30 and 120. Briefly, NCV assessments are performed on sedated NHPs. The stimulator probe is positioned over the median nerve with the cathode closest to the recording site and two needle electrodes are inserted subcutaneously on digit II at the level of the distal phalanx (reference electrode) and proximal phalanx (recording electrode), while the ground electrode is placed proximal to the stimulating probe (cathode). Following determination of the optimal stimulus location the stimulus strength is progressively increased and the stimulus responses are recorded and averaged. Responses are averaged, the distance (cm) from the recording site to the stimulation cathode are measured and the conduction velocity is calculated using the onset latency of the response and the distance (cm). Both the conduction velocity and the average of the SNAP amplitude are reported. The median nerve are tested bilaterally.

Echocardiogram assessment is performed at baseline, study days 14, 30, 60, 90 and 120. Animals are necropsied 120 days after administration and tissues harvested for biodistribution and a comprehensive histopathological examination. Additional specialized staining is performed for the heart. Cardiac and DRG transgene expression are evaluated with IHC or ISH. In addition, lymphocytes are harvested from the circulating compartment (peripheral blood mononuclear cells), spleen, and liver to evaluate the presence of T cells reactive to both the capsid and transgene product in these organs at the time of necropsy. Tissues are collected for vector biodistribution. Urine and feces are collected for vector excretion analysis using qPCR. The CSF and serum are also collected and archived for future possible analysis.

D. Toxicology of rAAVhu68.hFXN Administered Intravenous and Intraparenchymal (Dentate Nucleus) in Adult Rhesus Macaques (Nonclinical Study 12)

A 120 day safety study is conducted in adult rhesus macaques (3-8 years of age) to investigate the toxicology of rAAVhu68.hFXN following dual ROA, IV and IDN administration. Rhesus macaques receive an IV administration of rAAVhu68.hFXN at a dose of $3.0 \times 10^{13}$ GC/kg and a bilateral IDN injection of rAAVhu68.hFXN at a dose of $1.5 \times 10^{12}$ GC in 50 μL of ITFFB per injection for a total IDN dose of $3.0 \times 10^{12}$ GC/kg. The IV and IDN doses are based on the Nonclinical Study 7 and Nonclinical Study 8. The devices used for IDN administration is the same as in the Phase 1/2 FIH clinical trial (ClearPoint® System). The dosing regimen matches the Phase 1/2 FIH clinical trial (i.e., IV infusion followed by IDN injection). The 120 day evaluation period was selected to allow sufficient time for a transgene product to reach stable plateau levels following IV and IDN AAV administration. The age of administration was selected to be representative of the proposed clinical trial population. The study has QA oversight (conducted per protocol and oversight of key phases of the study and final report).

Baseline neurologic examinations (see Nonclinical Study 11 for details), clinical pathology (cell counts with differentials, clinical chemistries, and a coagulation panel), CSF chemistry, and CSF cytology are performed. After rAAVhu68.hFXN or vehicle administration, the animals are monitored daily for signs of distress and abnormal behavior.

Blood and CSF clinical pathology assessments and neurologic examinations are performed on a weekly basis for 30 days following rAAVhu68.hFXN or vehicle administration, and every 30 days thereafter. Additional blood clinical pathology assessment are performed 3 days after vector administration. At baseline, study days 0, 30 and 120, anti-AAVhu68 NAbs and cytotoxic T lymphocyte (CTL) responses to AAVhu68 and the rAAVhu68.hFXN transgene product are assessed by an interferon gamma (IFN-γ) enzyme-linked immunospot (ELISpot) assay. Nerve conduction velocity (NCV) assessment (see Nonclinical Study 11 for details) is performed at baseline, study days 14, 30 and 120. Echocardiogram assessments are performed at baseline, study days, 30, 60, 90 and 120.

Animals are necropsied 120 days after administration and tissues harvested for biodistribution and a comprehensive histopathological examination. In addition, lymphocytes are harvested from the circulating compartment (peripheral blood mononuclear cells), spleen, and liver to evaluate the presence of T cells reactive to both the capsid and transgene product in these organs at the time of necropsy. Tissues are collected for vector biodistribution. Urine and feces are collected for vector excretion analysis using qPCR. The CSF and serum are also be collected and archived for future possible analysis in case any finding warrants analysis.

Example 5—Cardiac and CNS co-administration of rAAVhu68.hFXN

Stocks of rAAVhu68.hFXN were formulated for intravenous delivery designed for targeting cardiomyocytes and DRG neurons and/or co-administration with rAAVhu68.hFXN formulated for direct injection to target dentate nuclei.

rAAVhu68.hFXN administration increased heart frataxin levels and significantly improved survival. Studies in non-human primates have demonstrated that the rAAVhu68.hFXN can efficiently express frataxin in key cellular targets with an acceptable safety profile. The IV ROA for rAAVhu68.hFXN was chosen to provide increased frataxin levels to the heart to address the cardiac manifestations of the disease, as cardiac failure is the cause of death for the majority of the population under study (early-onset FRDA patients). IDN administration for rAAVhu68.hFXN was chosen to increase frataxin level locally in the dentate nucleus to address the ataxic symptoms and prevent further impairment of speech, swallowing and gait in FRDA patients. In certain embodiments, rAAVhu68.hFXN may be suitable for combined central and intravenous routes of administration to address the cardiac and neurological features of FRDA.

Example 6—Method for Dose Scaling Between Species

A. Dose Scaling

The Fxn conditional murine disease models are utilized to demonstrate pharmacology of rAAVhu68.hFXN cannot be used to directly determine doses for human studies because of differences in target cells, ROA, and transduction differences between species. To determine the dose range for the Phase 1/2 FIH trial (Example 7), transduction data from the NHP toxicology studies is utilized. For the vector dose administered IV, the minimal effective dose (MED) is informed by data from the murine pharmacology study as well as the NHP toxicology study. The pharmacology study in the Fxn cKO mouse model is used to determine the relationship between the percentage of cardiomyocytes transduced and rescue of functional endpoints (e.g., a significant increase in survival). The NHP toxicology studies are then be utilized to identify a vector dose that achieves a similar level of cardiomyocyte transduction. The dose identified in NHP that yields a similar level of cardiomyocyte transduction to the minimum level associated with significant functional improvements in mice is considered the MED for the IV dose. The IV dose is scaled from NHPs to humans based on body mass.

For the vector dose administered to the dentate nuclei, a MED is determined in NHP based on transduction of target large neurons of the dentate nuclei. For scaling to human doses, the vector concentration is the same as that utilized in NHPs, but the total volume (and total vector dose) is linearly scaled based on the average relative volume of the dentate nuclei in NHPs and humans. Proportionally increasing the injection volume while maintaining a constant vector concentration allows the infusion to cover the entire dentate nucleus of each species while maintaining similar vector exposure to target cells.

B. Neuron Toxicity

Minimal to mild asymptomatic degeneration of DRG sensory neurons is not expected to appear in the rAAVhu68.hFXN GLP NHP toxicology study at all doses evaluated. However, the true risk of sensory neuron toxicity in humans is unknown. The current trial is designed to further improve on the safety profile of previous AAV clinical trials by using a dual ROA that requires lower doses of vector than those typically administered systemically, which appears to result in a lower degree of sensory neuron toxicity. This study also employs detailed monitoring for sensory changes as well as nerve conduction studies to detect even subclinical DRG toxicity. Given the severity of FRDA, the risk-benefit profile for dual route administration of rAAVhu68.hFXN is expected to remain favorable despite the unknown risk of sensory neuron toxicity.

C. Cardiotoxicity Potential of Frantaxin Overexpression

FRDA is caused by mutations in the FXN gene encoding the frataxin protein leading to a lack of frataxin and accumulation of iron in the mitochondria which predominantly affects cardiomyocytes and defined neuron populations in the CNS. rAAVhu68.hFXN is being developed to target peripheral organs, most notably cardiac myocytes (IV ROA) and central organs, cerebellum and sensory DRG neurons (IDN ROA), leading to supra-physiological levels of frataxin within days of administration. A recent publication explored the possibility of cardiotoxicity due to frataxin overexpression after gene therapy in Fxn conditional knock-out (Mck) mice compared to wild type mice using two different vectors (non-optimized and optimized; (Belbellaa et al., 2020)). The results from the three studies presented in the paper showed cardiotoxicity when frataxin is expressed at >20-fold the endogenous level but lack of cardiotoxicity when expressed at endogenous levels <9-fold. However, transgene expression and cardiotoxicity seemed to be higher when there was no frataxin present than if frataxin was already expressed.

The relevance of these results to our gene therapy program is unclear. Cardiotoxicity evaluation in NHP is more relevant to the proposed Phase 1/2 clinical trial than cardiotoxicity evaluation in mice. Cardiotoxicity was not observed in the completed NHP study (Nonclinical Study 7) when rAAVhu68.hFXN was administered IV at doses up to $1.0 \times 10^{11}$ GC/kg. However, this study was only 28 days in duration which may be too short to observe the hypertrophic cardiomyopathy as was reported and echocardiograms were not performed thus it is unclear if hypertrophic cardiomyopathy was present.

To evaluate possible cardiotoxicity due to frataxin overexpression after IV administration, echocardiogram assessments are conducted at different timepoints in the NHP toxicology studies (Nonclinical Study 11 and Nonclinical Study 12). In addition, following necropsy, a full histopathology evaluation of the heart is performed, while also assessing transgene expression in the heart. These assessments assist with the evaluation of co-localization of cardiac pathology and frataxin overexpression. Furthermore, in the MED study (Nonclinical Study 9), we perform full histopathology evaluation, and also evaluate SDH activity in the heart, since it was reported to be impaired due to frataxin overexpression.

Cardiotoxicity was apparent 8-14 weeks after gene therapy delivery. The proposed 120 day duration of the MED study (Nonclinical Study 9) and toxicology studies (Nonclinical Study 11 and Nonclinical Study 12) are sufficient duration to assess cardiotoxicity.

Example 7—Clinical Protocol

Figure 4A:
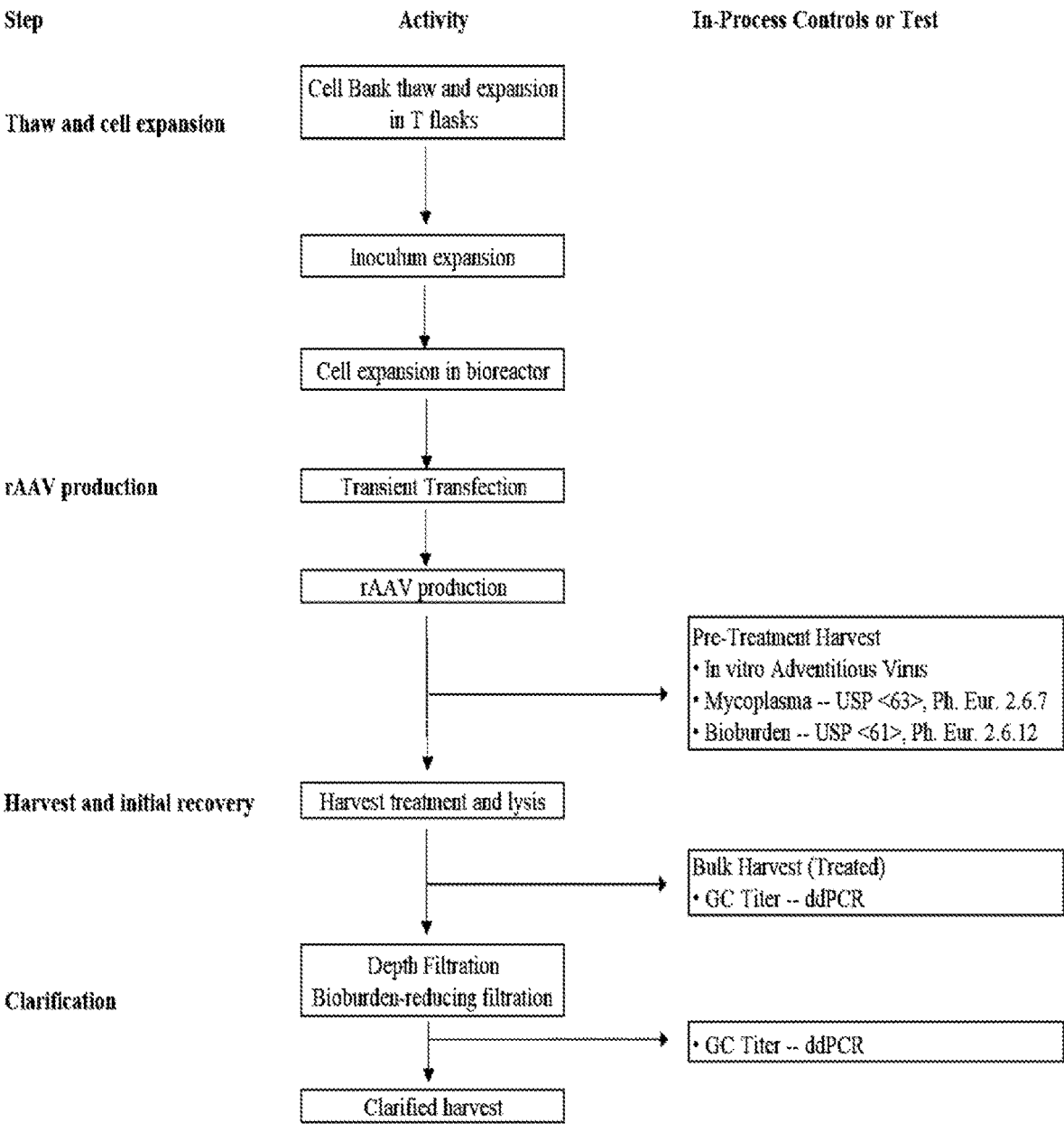
FIGS. 4A and 4B provide a manufacturing process flow diagram for drug substance.
Figure 4B:
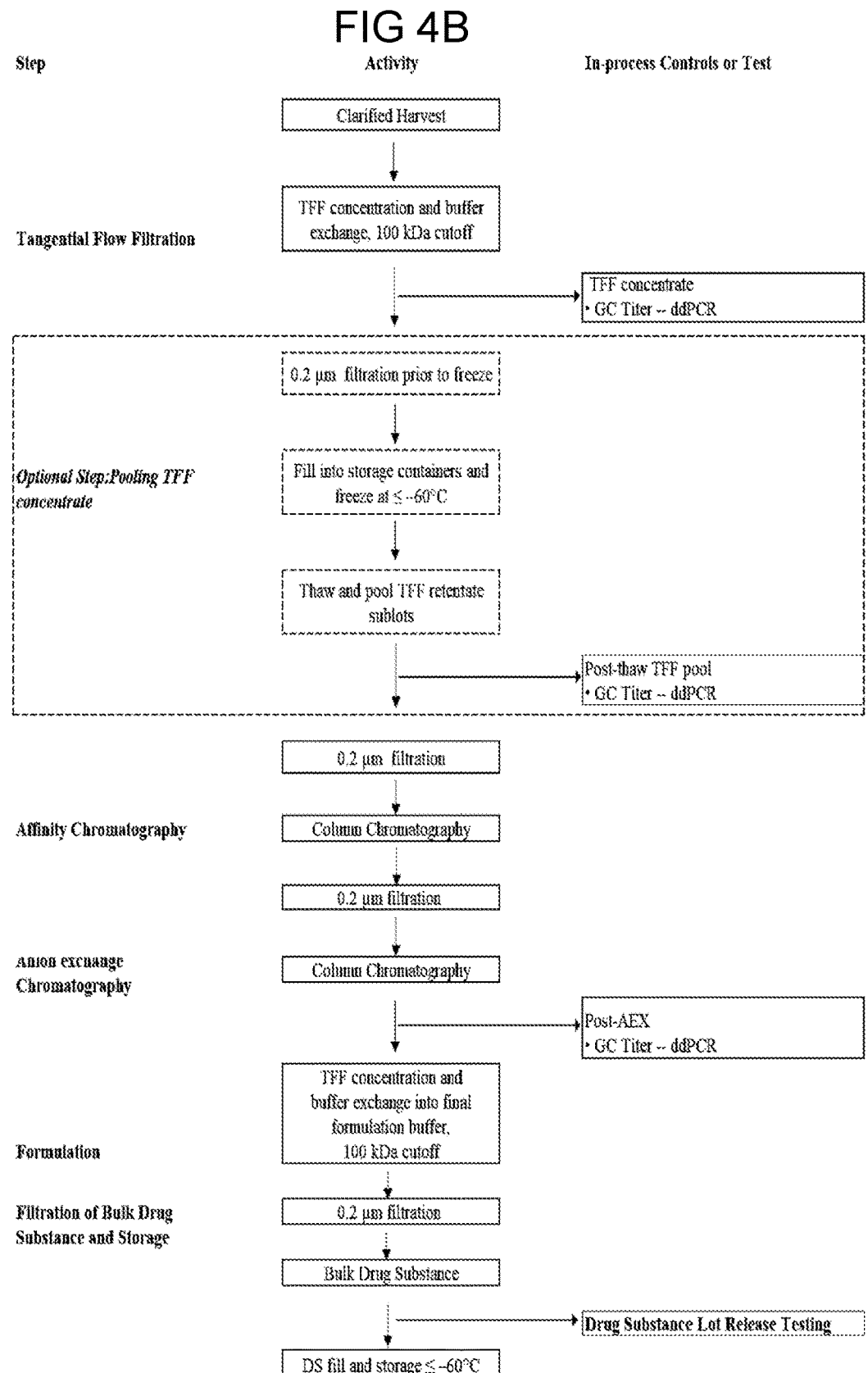

A. Manufacturing process for rAAVhu68.hFXN rAAVhu68.hFXN for the FIH trial is manufactured by transient transfection of HEK293 cells followed by downstream purification using a process previously developed. The product is produced at the CMO facility in a controlled environment consistent with FDA regulations ("Guidance for Industry—cGMP for Phase 1 Investigational Drugs," July 2008), which ensures the safety, identity, quality, purity, and strength of the manufactured biologic. A manufacturing process flow diagram is shown in FIGS. 4A and 4B. The proposed in-process tests are depicted on the right side of the diagram. A description of each production and purification step is also provided. Product manufacturing follows a linear flow of unit operations and utilizes disposable, closed bioprocessing systems unless otherwise specified. rAAVhu68.hFXN is the sole product manufactured within a specified production suite at a single time at the multiproduct CMO, with changeover controls in place between products. Cells are thawed in single use T-flasks and expanded into single use sterile shake flasks that are used to innoculate a fixed bed, controlled, single use production bioreactor. All seed train open manipulations are performed in class II biological safety cabinets (BSCs) in an ISO Class 5 environment. The purification process is performed using commercially supplied filters and chromatography resins. The Intrathecal Final Formulation Buffer (ITFFB) solution is manufactured by process comprising compounding of the ITFFB formulation buffer, sterile filtration, followed by aseptic filing into vials. The manufacturing process follows standard procedures for solution compounding and 0.2 μm sterile filtration followed by aseptic processing.

B. Overview of First-in-Human Trial

The FIH trial is a Phase 1/2, open-label, multi-center, dose escalation study of rAAVhu68.hFXN to evaluate safety, tolerability, pharmacodynamics, and efficacy in subjects with early onset Friedreich's Ataxia (FRDA) aged 16 years and older. A two-stage dosing design is utilized. Dosing in each stage and cohort consists of a one-time administration of two doses of rAAVhu68.hFXN, each delivered via a different route within 24 hours. The first dose is adminis- tered via intravenous (IV) infusion followed by a second dose administered to each of the dentate nuclei via intra- parenchymal dentate nucleus (IDN) injection. Stage 1 com- prises the dose escalation phase of the study and involves sequential administration of a low dose of dually-delivered rAAVhu68.hFXN (Cohort 1) followed by a high dose of dually-delivered rAAVhu68.hFXN (Cohort 2) in non-ambu- latory subjects. Both dose levels have the potential to confer therapeutic benefit, with the understanding that, if tolerated, the higher dose regimen is expected to be advantageous. The sequential evaluation of the low dose regimen (Cohort 1) followed by the high dose (Cohort 2) enables the identifi- cation of the maximum tolerated dose (MTD) of the two dose regimens tested. Based on Stage 1 data, ambulatory FRDA subjects (Cohort 3) are enrolled into Stage 2 and are dosed with the MTD of rAAVhu68.hFXN in a parallel fashion. The rAAVhu68.hFXN dose levels is determined based on data from the murine MED study (Examples 4A and 4B) and GLP NHP toxicology study (Examples 4C and 4D) and consists of a low dose (administered to Cohort 1) and a high dose (administered Cohort 2). Our standard approach is that a safety margin is applied so that the high dose selected for human subjects is 30-50% of the equiva- lent MTD in NHPs. The low dose is typically 2-3-fold less than the selected high dose provided it is a dose that exceeds the equivalent scaled MED in the animal studies.

The aim of the study is to evaluate the safety and tolerability of rAAVhu68.hFXN. Additionally, pharmacody- namic outcomes, as well as exploratory efficacy outcomes, are assessed to evaluate the potential of rAAVhu68.hFXN to improve or stabilize the symptoms of FRDA.

The study design staggers enrollment of each subject by a 30 day interval in both Cohort 1 (low dose) and Cohort 2 (high dose). The rationale for this approach is that the delivery method for rAAVhu68.hFXN is a novel procedure and this approach allows for additional safety monitoring after each subject undergoes the procedure. Furthermore, this 30-day window captures the time when maximal gene expression is expected based on nonclinical data.

An independent Data Safety Monitoring Board (DSMB) conducts a safety review of all accumulated safety data between cohorts and after full enrollment of the second cohort to make a recommendation regarding further conduct of the trial. The DSMB also conducts a review any time a safety review trigger (SRT) is observed. The 30-day dosing interval between each subject in Cohorts 1 and 2 allows for evaluation of AEs indicative of acute immune reactions, immunogenicity, or other dose-limiting toxicities during the interval in which maximal gene expression is expected. The DSMB review conducted at the end of Cohorts 1 and 2 is performed once 30 days of safety data from each patient in the respective cohort has been collected and fully analyzed. This data collection is expedited by the fact that the planned trial is open label and therefore data can be analyzed in real time. If there is a safety event that triggers a DSMB review outside of the specified checkpoints, this interval may be extended such that no new recruitment occurs until after a decision is made by the DSMB. The 30-day interval may also be extended to accommodate this review.

Provided that the DSMB recommends study continuation after completion of Cohort 2, additional subjects are enrolled in an expansion cohort that receive the MTD. Enrollment of these additional subjects does not require a 30-day observation window between subjects.

All treated subjects are followed for 2 years to evaluate the safety profile and characterize the pharmacodynamic and efficacy properties of rAAVhu68.hFXN. Subjects are fol- lowed for an additional 3 years (for a total of 5 years post-dose) during the LTFU period of the study to evaluate long-term clinical outcomes, which is in line with the draft "*FDA Guidance for Industry: Long Term Follow-Up after Administration of Human Gene Therapy Products*" (January 2020).

TABLE 7

| First-in-Human clinical Trial Protocol Synopsis. |
| --- |

| | |
| --- | --- |
| Protocol(s) Title | A Phase 1/2 Multi-Center, Dose Escalation Study to Assess the Safety, Tolerability, and Pharmacodynamics of Single Doses of Dual-Administration GTP-212 Delivered Intravenously (IV) and via Intraparenchymal Dentate Nucleus (IDN) injection of Subjects with Friedreich's Ataxia (FRDA) |
| Objectives and Endpoints | The primary objective of this study is to assess the safety and tolerability of a dual route administration of rAAVhu68.hFXN through evaluation of: Adverse events (AEs) and serious adverse events (SAEs) Vital signs and physical examinations Neurological examinations Cardiac monitoring Laboratory assessments (serum chemistry, hematology, coagulation studies, liver function tests [LFTs], urinalysis, and CSF chemistry and cytology) C-SSRS Immunogenicity of the vector and transgene product Vector shedding The secondary objectives of this study are to assess the pharmacodynamics and biological activity and efficacy of dual administration of rAAVhu68.hFXN as well as improvements in the quality of life of treated subjects over 2 years based on the following endpoints: Quality of Life (QoL) as assessed by the Activities of Daily Living (ADL) questionnaire at 2 years post-rAAVhu68.hFXN treatment |

TABLE 7-continued

First-in-Human clinical Trial Protocol Synopsis.

|  |  |
|---|---|
|  | Quality of Life (QoL) as assessed by the Patient- and Clinician-Global Impression of Change surveys (P-GIC and C-GIC, respectively) at 2 years post-rAAVhu68.hFXN treatment Change from baseline in ejection fraction assessed at the 2 years post-rAA Vhu68.hFXN treatment Heart strain and relative wall thickness (RWT) as measured by echocardiogram and cardiac MRI at 2 years post-rAAVhu68.hFXN treatment Further secondary key efficacy endpoints include: For Stage 1 (Cohorts 1 and 2): Change in speech ability, as assessed by a summative speech assessment score measuring multiple aspects of speech and voice quality at 2 years post-rAAVhu68.hFXN treatment For Stage 2 (Cohort 3): Ambulation as measured by change from baseline at the 2 year time point in the upright stability subsection of the mFARS assessment The exploratory objectives of the study are to further assess the efficacy of dual route administration of rAAVhu68.hFXN through the following endpoints: General: Survival Levels of frataxin expression in serum samples evaluated at 1year post-rAAVhu68.hFXN treatment Quality of Life (QoL) as assessed by a FRDA-specific patient reported outcome questionnaire currently being developed by the Friedreich's Ataxia Research Alliance at 2 years post-rAAVhu68.hFXN treatment Neurological Endpoints mFARS assessment as compared to baseline score to measure overall disease state over time 9-hole peg test (9HPT) if subject is able to perform in <5 minutes; or use a spoon dexterity test if subject is unable to complete the 9HPT Further exploratory neurological endpoints for subjects enrolled into Stage 2 only include: Ambulation as assessed by a 25-foot walk test at 2 years post-rAAVhu68.hFXN treatment Cardiac Endpoints Electrocardiogram changes Absence of progression of cardiac symptoms, including ICD and heart failure hospitalization |
| Study Design | This is a Phase 1/2 first-in-human, multi-center, dose escalation study to evaluate safety, tolerability, pharmacodynamics and efficacy of rAAVhu68.hFXN in up to 16 subjects, but at least 12 subjects with early onset FRDA with age of onset at <14 years old and current age 16 years old or older. The study provides proof of concept in assessing safety, tolerability, pharmacodynamics and exploratory efficacy of dual-route administration of rAAVhu68.hFXN, all of which assist in defining rAAVhu68.hFXN dose and endpoints for a registration trial. A two-stage dosing design, comprising 3 cohorts (described below), are utilized. Patients are administered corticosteroids immediately prior to and for 1-week post IDN administration to minimize any potential brain inflammation related to the study procedure. Furthermore, if at any time post-IV/IDN administration transaminase elevations are observed, the steroid dose are increased or reinitiated. A prolonged regimen of corticosteroids may also be utilized in order to mitigate potential immune-related injury, such as hepatoxicity. The final prophylactic steroid protocol is developed in line with GLP toxicology studies to be performed. In line with this corticosteroid administration, subjects are closely monitored for signs of brain inflammation and immune toxicity as well as issues related to steroid dosing. A full dosing regimen is provided in the eventual first-in-human study protocol. Dosing in each stage and cohort consist of a one-time administration of two doses of rAAVhu68.hFXN with the first dose delivered via the IV ROA followed by a second dose delivered via an IDN injection within 24 hours. This administration order is subsequently referred to as dual-route dosing. Dose administration occurs in an inpatient setting. Each patient is seen on a regular basis for completion of study-related procedures as listed in the Schedule of Events. An independent Data Safety Monitoring Board (DSMB) is utilized throughout the study. The DSMB specifically advises on continuation of dose escalation within Stage 1 of the study as well as provide continual safety monitoring oversight any time a safety review trigger (SRT) is observed. Stage 1 (n = 6) Stage 1 of this study is the dose escalation phase and assesses the safety and tolerability of a one-time, dual-route administration of rAAVhu68.hFXN in 2 treatment cohorts (Cohort 1 and Cohort 2). Each cohort consists of 3 non-ambulatory FRDA subjects. Sequential dosing, with a 30-day dosing interval between each subject in each cohort, is utilized to assess adverse events (AEs) |

TABLE 7-continued

First-in-Human clinical Trial Protocol Synopsis.

|  |  |
|---|---|
|  | indicative of acute immune reactions, immunogenicity, and other dose-limiting toxicities. Both dose levels evaluated in Stage 1 are anticipated to confer therapeutic benefit, with the understanding that, if tolerated, the higher dose is expected to be advantageous.<br>Cohort 1 (low dose rAAVhu68.hFXN): This cohort consists of 3 subjects (Subjects 1-3) who receive dual route administration of rAAVhu68.hFXN with both procedures being performed within 24 hours. Dosing in this cohort is sequential, with each subject dosing separated by 30 days. All available Cohort 1 safety data are evaluated by an DSMB 30 days after Subject 3 is administered rAAVhu68.hFXN. Based on their review, the DSMB provide a recommendation on the initiation of Cohort 2 dosing.<br>Cohort 2 (high dose rAAVhu68.hFXN): This cohort consists of 3 new subjects (Subjects 4-6) who receive dual route administration of rAAVhu68.hFXN with both procedures being performed within 24 hours. Dosing in this cohort is sequential, with each subject dosing separated by 30 days. All available Cohort 2 safety data are evaluated by the DSMB 30 days after Subject 6 is administered rAAVhu68.hFXN to make a recommendation on study continuation.<br>At this time, the DSMB also performs a combined review of all available Cohort 1 and Cohort 2 safety data to enable the identification of the maximum tolerated dose (MTD) to be evaluated in Stage 2 of this study.<br>Stage 2 (n = 6 to 10)<br>Stage 2 assesses the safety, tolerability, pharmacodynamics and efficacy of a one-time, dual-route administration of rAAVhu68.hFXN (with both procedures performed within 24 hours) in a single Cohort (Cohort 3) comprised of at least 6 (and up to 10) ambulatory FRDA subjects. All Cohort 3 subjects are dosed in parallel with the rAAVhu68.hFXN selected for evaluation based on the Stage 1 data review. |
| Study Duration | The duration of participation in this protocol is 5 years in accordance with "FDA Guidance for Industry: Long Term Follow-Up after Administration of Human Gene Therapy Products" (January 2020). |
| Number of Subjects | Up to 16 FRDA subjects are enrolled as follows:<br>6 non-ambulatory FRDA subjects; 3 in each of the Stage 1 cohorts (Cohorts 1 and 2)<br>6 to 10 ambulatory FRDA subjects in the Stage 2 cohort (Cohort 3) |
| Study Center | Multi-center<br>Centers in the US and outside of the US capable of performing administration of gene product serve as rAAVhu68.hFXN dosing centers for all enrolled study participants<br>Study follow-up visits and assessments are performed at select regional medical centers that are a part of the Friedreich's Ataxia Research Alliance (FARA) network in the US and EU by physicians who treat FRDA patients |
| Main Inclusion Criteria | All subjects are required to meet the following criteria:<br>Age ≥16 years<br>Genetically confirmed FRDA with age of onset <14 years<br>Men and women of child-bearing potential (WCBP) must use a highly effective method of birth control defined as those, alone or in combination, that result in a low failure rate, i.e, less than 1% per year when used consistently and correctly.<br>A baseline serum AAVhu68 neutralizing antibody titer ≤1:10<br>Subjects must be able to comprehend and be willing to provide an institutional review board/ethics committee (IRB/EC) approved Informed Consent Form (ICF) either themselves if over the age of 18 or with assent from the patient and an ICF signed by a parent or legal guardian if ages 16-<18.<br>Subjects must be willing to comply with all study-related procedures and be available for the duration of the study.<br>Additional Criteria for Stage 1 (Cohorts 1 and 2):<br>Subjects are required to have lost ambulation, defined as having a Functional Staging of Ataxia score of either 5.0 or 5.5 (out of 6)<br>Subjects are required to have some level of spontaneous speech, defined as a score of <3 (out of 3) on the Spontaneous speech mFARS sub-assessment<br>Subjects meeting any of the following structural cardiac criteria:<br>Left ventricular end diastolic diameter (LVEDD) > ULN<br>Septal wall thickness (SWT) > ULN found on baseline ECHO/cMRI findings<br>LV mass > ULN on baseline ECHO/cMRI findings<br>Additional criteria for Stage 2 (Cohort 3):<br>Ability to walk independently, with or without an assistive device, as defined by having the ability to both:<br>Stand with feet apart and eyes open for >1 minute<br>Complete a 25-foot walk test in <1 minute<br>Subject has an mFARS score of >30 at baseline<br>Subject has a septal wall thickness OR left ventricular (LV) mass >ULN on baseline ECHO/cMRI findings |

TABLE 7-continued

First-in-Human clinical Trial Protocol Synopsis.

| | |
|---|---|
| Main Exclusion Criteria | The following exclusion criteria apply to subjects in both study Stages: Subjects who are compound heterozygous with 1154F or G130V point mutations for FRDA Subjects with severe dysarthria who would, in the opinion of the investigator, be unable to perform the speech related tasks Patients with vision worse than 20/200 or deaf patients at baseline Active arrhythmia OR ejection fraction <35% at baseline Diagnosed coronary heart disease Diagnosed symptomatic heart failure Uncontrolled diabetes defined as HbA1c >8% at baseline Any contraindication to the direct injection administration procedure into the dentate nucleus, including contraindications to fluoroscopic imaging Any contraindication to MRI or lumbar puncture (LP) Chronic renal insufficiency defined as estimated GFR <30 mL/min/1.73 m$^2$ Abnormal liver function tests (LFTs) at screening (AST or ALT >2 × upper limit of normal (ULN) and/or total bilirubin of >1.5 × ULN unless subject has unconjugated hyperbilirubinemia due to Gilbert's syndrome). History of cirrhosis or chronic liver disease based on documented histological evaluation or non-invasive imaging or testing. Patients with a positive test result for human immunodeficiency virus (HIV) or untreated Hepatitis C (HepC) Active tuberculosis, systemic fungal disease, or other chronic infection. Any clinically significant neurocognitive deficit not attributable to FRDA that may, in the opinion of the Investigator, confound interpretation of study results Any current or previous condition or physical exam or laboratory test finding that, in the opinion of the Investigator, would put the subject at undue risk or would interfere with evaluation and interpretation of the investigational product safety or efficacy results Enrollment in any other clinical study with an investigational product within 4 weeks prior to screening or within 5 half-lives of the investigational product used in that clinical study, whichever is longer, or any subject who has had any other prior gene therapy. |
| Investigational Product | rAAVhu68.hFXN |
| Reference Therapy | None |
| Route of Administration and Procedure | rAAVhu68.hFXN is administered via 2 routes (dual-route injection) as two sequential doses to in-patient participants: subjects receive one dose via a peripheral vein by IV infusion and the other by IDN injection. The volume of the IV infusion depends on the dose level and the weight of the subject. |
| Safety Assessments | Safety assessments, including collection of AEs and SAEs, physical and neurologic examinations, vital signs, clinical laboratory tests (serum chemistry, hematology, coagulation, LFTs, urinalysis), cardiac parameters, nerve conduction studies, and CSF cytology and chemistry (cell counts, protein, glucose) are performed at the times indicated in the study schedule). Additional safety assessments are added to the clinical trial protocol based on the findings of the GLP toxicology study. For instance, minimal to mild asymptomatic degeneration of DRG sensory neurons has been observed in NHP studies using AAV gene products (Hordeaux et al., 2018a; Hordeaux et al., 2018b; Hordeaux et al., 2018c) and is a potential risk for gene therapy products in general. It is not expected that this DRG toxicity to be observed for this program as it does not utilize an intracisterna magna route of administration and both doses for this trial are less than the dose at which this toxicity was observed using an IV administration (Hordeaux et al,, 2018c). Furthermore, based on existing non-clinical and clinical data for other AAV programs, it is anticipated that these sensory neuron findings do not translate to AEs in humans. However, if this DRG toxicity is observed during the GLP toxicology studies, additional safety assessments, including detailed monitoring for sensory changes as well as nerve conduction studies to be added to the clinical trial protocol. The Investigator has primary responsibility for the ongoing medical review of safety data (AEs, SAEs, laboratory data, etc.) throughout the study and prior to enrollment of each subject during the dose escalation phase. A Safety Review Board reviews safety data at specified intervals throughout the study and make recommendations to the Sponsor regarding further conduct of the study. The full details of the safety review process are still under discussion, but broadly speaking, safety evaluations after the first three subjects in Cohort 1 and after the first three subjects in Cohort 2 are conducted as described. A full list of events that are considered SRTs are included in the FIH study protocol. However, an outline of criteria/events that would result in study termination (i.e., no additional subjects would be enrolled, but all subjects who had already received rAAVhu68.hFXN would continue to receive follow-up for the planned duration of the study) or study suspension (i.e., enrollment would be temporarily halted to allow full review of the safety data) is included ). Decision tree for safety evaluations for the proposed Phase 1/2 trial is used in consideration for medical review. Medical review is performed by the Medical Monitor in conjunction with the Principal Investigator Abbreviations: AE, adverse event. |

TABLE 7-continued

| First-in-Human clinical Trial Protocol Synopsis. |
| --- |

| | |
| --- | --- |
| | Stopping Rules Include:<br>Events that meet study stopping criteria include:<br>A Grade 4 or 5 AE according to CTCAE version 5.0 criteria that the<br>Investigator considers to be related to either the investigational product, or<br>the IV administration or IDN injection procedure<br>ALT or AST ≥3 × ULN and total bilirubin ≥2 × ULN and no other reason<br>can be found to explain the changes observed<br>The Safety Board reviews these AEs and renders a decision regarding continued<br>conduct of the study and subject enrollment. |
| AAV-<br>associated<br>Risks | Recombinant AAV vector genomes display inefficient integration into the host<br>chromosome and predominantly persist in episomal form (McCarty et al., 2004).<br>The risk of tumorigenesis in humans due to insertional mutagenesis is unknown, but<br>considered low at this time.<br>NHP studies of ICM AAVhu68 delivery have demonstrated minimal to mild<br>degeneration of peripheral sensory neurons in some animals. These lesions have not<br>been associated with sensory deficits detectable by routine observations or on<br>neurological exams. The risk of clinically meaningful sensory loss is therefore<br>anticipated to be low. Detailed examinations are performed to evaluate sensory<br>nerve toxicity, and sensory nerve conduction studies are employed in this trial to<br>monitor for subclinical sensory neuron lesions. The 30 day observation period<br>between subjects is expected to be sufficient to detect the development of sensory<br>deficits, as sensory neuron lesions appear within 2-4 weeks after AAV<br>administration in non-clinical studies.<br>To assess potential immunogenic responses, the presence, absence, and titer of anti-<br>AAVhu68 NAbs in both CSF and serum are examined at defined follow-up time<br>points. |
| Statistical<br>Methods | No statistical comparisons are planned for safety evaluations. All results are<br>descriptive only. Data is listed, and summary tables are produced.<br>Measurements at each time point are compared to baseline values for each subject,<br>as well as natural history data from FRDA patients with comparable cohort<br>characteristics where available for each endpoint.<br>A statistical analysis plan is developed that describes the integration of the<br>comparator dataset with the FIH trial data and details the planned analyses and<br>comparisons. |

Subjects are admitted to the hospital for on the morning of Day-1 and remain in-hospital through Day 1, at least 24-hours post-IDN procedure to observe for any acute adverse events. At the discretion of the PI, and dependent upon a favorable safety evaluation, subjects may be discharged from the hospital and all subsequent visits performed as an outpatient. At the discretion of the principal investigator, subjects may remain in the hospital through Day 7, if the visits for this time period cannot be performed on an outpatient basis, as there are several visits during this period. Vector administration occurs in two processes: vector is first administered via IV infusion to a peripheral vein. After the IV infusion is completed, vector is then administered by direct injection using the ClearPoint® injection system. The intraparenchymal (dentate nucleus) injection should occur within 24 hours to prevent an immunologic reaction to the vector administered intravenously. Other laboratory assessments may be conducted as needed. Fasting is preferred but not required. Urine pregnancy testing is performed for women of child bearing potential only. A serum pregnancy test is performed in the event of a positive or equivocal urine pregnancy test result. Vital signs are monitored frequently throughout Days 0 and 1, including assessments every hour (+/−5 minutes) for the first 12 hours and every 2 hours for the following 36 hours, throughout the first 48 hours. During visits when an ECG is performed and vital signs are measured, the ECG should be performed first. On days where speech assessment is performed, this assessment should be performed first. Patients are administered corticosteroids immediately prior to and for 1 week post-IDN administration to minimize any potential brain inflammation related to the study procedure. The dosing regimen is tapered over the seven days of administration. If at any time post-IV/IDN administration transaminase elevations or hepatoxicity are observed, the steroid dose is increased or reinitiated. A full dosing regimen and frequency of administration, as well as a monitoring plan for risks associated with prophylactic corticosteroid use, is detailed in a protocol for the first-in-human study (above).

C. Study Population Rationale

Study Population Characteristics

The FIH trial focuses on patients ages >16 years diagnosed with early-onset (defined as age of onset <14 years) FRDA. This population was chosen for a FIH trial as they present with both the neurological and cardiac manifestations of the disease, progress at a faster rate, and are more homogeneous in their disease presentation than late-onset patients, making them the most appropriate population for whom a stabilizing, disease-modifying therapy would be most beneficial. These subjects also represent a population with high unmet need because disease-modifying or stabilizing therapies for FRDA are still lacking.

The early-onset form of FRDA has a variable age of onset occurring between 10.5-15.5 years old (Harding, 1981; Filla et al., 1990; Durr et al., 1996; Parkinson et al., 2013). The age of disease onset is correlated to severity of disease, with younger patients generally experiencing more severe symptoms and a faster rate of disease progression (Reetz et al., 2015). Conversely, late-onset FRDA patients typically display a more mild range of symptoms, with some never displaying the cardiac symptoms that are the most common cause of mortality in the general population of FRDA (De Michele et al., 1994; Bhidayasiri et al., 2005). Thus, as late-onset FRDA patients have a more variable distribution of symptoms and age of disease onset, designing a clinical trial that would unequivocally demonstrate efficacy of rAAVhu68.hFXN that includes these patients would be prohibitively difficult. Additionally, demonstration of improvement or stabilization of the late-onset form of the disease would not necessarily predict a demonstrable improvement in the more severe, early-onset, patients. Therefore, despite a shared underlying pathology between the early- and late-onset forms of the disease, we propose enrolling early-onset FRDA patients to test the efficacy of this gene product in the proposed FIH study. In certain embodiments, the population for whom this therapy is most appropriate are re-evaluated for subsequent studies.

Justification of Neurologic and Cardiac Eligibility Criteria

The dose escalation phase (Stage 1) of the FIH study is intended to evaluate the safety of rAAVhu68.hFXN and identify a safe dose to take into further development, and given the lack of human experience with rAAVhu68.hFXN. The Stage 1 (Cohorts 1 and 2) enroll subjects with more advanced disease who have the highest unmet need for new therapies. Subjects recruited in Cohorts 1 and 2 are non-ambulatory, defined as scoring 5.0 or 5.5 out of 6 on the Functional Staging of Ataxia assessment which is validated for assessing ambulation for FRDA (Subramony et al., 2005). A score of 5.0 or 5.5 on this assessment recruits subjects who are non-ambulatory, but who do not have total dependency for all activities of daily living. As preservation and quality of speech are important to patients with FRDA, the potential impact on dysarthria from the IDN injection is assessed in this cohort. Therefore, the spontaneous speech subscore of the mFARS examination is used to recruit subjects for this study and enroll subjects who score a 0, 1 or 2 (out of 3) on this assessment at baseline. This score ensures the recruitment of subjects with dysarthria but who also have some preservation of speech.

Stage 2 (Cohort 3) enrolls subjects with less progressed disease who are ambulatory. Ambulatory is defined as being able to complete a 25-foot walk test in <1 minute with or without assistive devices and meeting the standing with eyes open criterion of the upright stability subsection the mFARS (i.e. score of 0 or 'normal' out of 4 points) which corresponds to the subject standing with their feet 20 cm apart and eyes open for >1 minute (Subramony et al., 2005; Rummey et al., 2020a). The goal of these inclusion criteria is to select a population in whom GTP-212 has the potential to improve or stabilize ambulation.

Patients with early-onset FRDA are predicted to completely lose ambulation 11.5 years after disease onset. According to this data, loss of ambulation occurs in a stepwise fashion. First, patients lose the ability to stand on their dominant foot, followed by the ability to stand in tandem, and subsequently the ability to stand feet together and eyes closed, typically all before receiving an FRDA diagnosis. After being diagnosed with FRDA, various additional aspects of ambulation are lost, with patients next losing the ability to stand with eyes closed and feet apart, followed by standing with eyes open and feet together, and finally with eyes open and feet apart. The first of these steps is predicted to occur an average of 4.1 years after diagnosis, followed by averages of 5.8 years and 9.3 years, respectively (Rummey et al., 2020a; Rummey et al., 2020b). Once these milestones are lost in the progression of the disease, they are not regained, thus stabilizing these patients as soon as possible after their diagnosis is critical to the maintenance of their ambulatory capabilities. As subjects recruited into this trial would likely have already lost some of these milestones at the trial start, the amount of time they are expected to remain ambulatory is less than the 11.5 years predicted time to ambulation loss beginning at the onset of disease. Furthermore, as there are no currently available treatments for FRDA (Section 3.4), treatment with rAAVhu68.hFXN would provide a potentially therapeutic option to these subjects that could allow for them to maintain or improve upon their current state of ambulation.

Additionally, it is possible that early treatment may result in stabilization or improvements in cardiac and neurological parameters of the disease. Requiring an mFARS score of >30 points allows for the recruitment of subjects who are in the early stages of disease progression and for whom stabilization or improvements in ambulation could be observed. Furthermore, this mFARS requirement prevents the recruitment of subjects who are asymptomatic or who have not yet progressed significantly in their disease. Based on feedback from key opinion leaders and physicians in the Friedreich's Ataxia field, an mFARS score of >30 allows us to recruit patients who can benefit the most from this treatment and allows us to monitor whether this therapy may affect neurological symptoms of the disease.

Although FRDA presents initially with ataxia symptoms, nearly all patients eventually develop cardiac symptoms later in disease progression. Since cardiac failure is the most common cause of death for FRDA patients (Tsou et al., 2011), one goal of this therapy is to prevent the manifestation of these cardiac symptoms. For this reason, subjects who are at a higher risk for future cardiac manifestations are recruited based on their baseline structural cardiac parameters. In Stage 1, subjects are required to meet one of the following structural cardiac parameters at baseline, as assessed by ECHO or cMRI readings: left-ventricular end diastolic diameter (LVEDD) >ULN, septal wall thickness (SWT) >ULN, or LV mass >ULN. These requirements were derived from the FA-COMS natural history data and key opinion leaders and physicians in the FRDA field as being sufficient to recruit patients with a higher than average risk of future cardiac manifestations. In Stage 2, subjects have less stringent cardiac inclusion criteria as they are earlier in disease progression. Specifically, subjects are required to have a septal wall thickness or LV mass above the upper limit of normal. By recruiting subjects with these parameters, we enroll patients at a high risk of developing cardiac symptoms within the timeframe of this clinical trial who would have the highest benefit from treatment with this therapy.

Dual Route of Administration

A dual ROA allows to target both the cardiac and neurological manifestations of the disorder. Delivery of rAAVhu68.hFXN by an IV infusion as well as an IDN injection into each of the dentate nuclei is proposed as a mechanism by which to treat peripheral manifestations of the disease as well as the neurological aspects. Patients may receive this treatment via IV administration to prevent the manifestation of cardiac symptoms of this disease, including cardiac death. Delivery of rAAVhu68.hFXN via IDN administration also addresses the neurological manifestations of the disorder, such as the ataxia, dysmetria, and dysarthria, along with peripheral neuropathy observed in FRDA patients. Thus, delivering the vector via a dual administration to these tissues to allow for expression of frataxin is intended to prevent the more severe cardiac manifestations of the disease as well as stabilize or improve the ataxic symptoms of the disease. Details of the administration procedure for the IV administration and for the IDN administration are provided in Examples 7E, 7F, and 7G.

Endpoints

In addition to measuring safety and tolerability as the primary endpoint, pharmacodynamic and efficacy endpoints were chosen on their ability to measure meaningful functional and clinical outcomes in this population. All neurological endpoints, with the exception of assessing frataxin expression in serum at 1 year post-rAAVhu68.hFXN treatment, are assessed continually throughout the trial and evaluated at 2 years post-dose. During the long-term follow up phase occurring for the last 3 years of the study, study visit frequency decrease to once every 6 months, with alternating evaluation of cardiac and neurological endpoints such that each set of measurements is evaluated annually. This approach allows for thorough evaluation of pharmacodynamics and clinical efficacy measures in treated subjects over a period of follow up for which untreated comparator data exist. Subjects continue to be monitored for safety and efficacy for a total of 5 years after rAAVhu68.hFXN administration, in accordance with "FDA Guidance for Industry: Long Term Follow-Up After Administration of Human Gene Therapy Products" (January 2020).

Following study completion, patients may be invited to enroll in a patient-registry for continued monitoring. The neurological symptoms of FRDA generally appear first with cardiac manifestations occurring later in disease progression. In focusing on the high-risk FRDA population, the goal is to recruit subjects who would be expected to show both neurologic and cardiac symptoms within trial time frame. Administration of rAAVhu68.hFXN is expected to improve disease status, thereby delaying the deterioration of neurological parameters and the onset of cardiac symptoms, both of which would be improvements in the disease for the target population. As the most common cause of mortality in these patients is cardiomyopathy (Tsou et al., 2011), rAAVhu68.hFXN is thereby expected to extend the life expectancy for these patients as well.

In line with how FDRA manifests, the proposed efficacy endpoints are divided into those that measure changes in the neurological and cardiac parameters of the disease. Changes in biomarkers and quality of life assessments are also summarized.

Pharmacodynamic endpoints

Biomarkers

To assess expression of frataxin by rAAVhu68.hFXN, frataxin protein levels are measured in serum to monitor the level of vector expression. Serum is analyzed for frataxin levels at the pre-dose, 3 months, and 1 year time points using a lateral flow immunoassay, with the endpoint being evaluations at the 1-year timepoint. This assay has been described previously (Willis et al., 2008; Deutsch et al., 2010).

Neurological Endpoints

To assess the effect of rAAVhu68.hFXN on the neurological progression in FRDA, the following parameters are evaluated relative to both the subject's values at baseline and to cohort—matched natural history data over the course of the 5 year follow up of the study. An interim analysis of all neurological endpoints are performed from data collected over the first 2 years of follow up. A final evaluation of neurological endpoints is performed with data collected over the 5 year duration of the study.

mFARS

An overall measure of neurological function is the FARS rating scale for Friedreich's Ataxia. The FARS scale is an exam-based rating scale that assesses neurological function over 5 areas of disease involvement (bulbar, upper limb, lower limb, peripheral nervous system, and upright stability) (Subramony et al., 2005). When compared with other FRDA rating scales, such as the International Cooperative Ataxia Rating Scale (ICARS), it was found to have the greatest effect size and require fewer patients and was therefore recommended for use in clinical trials (Fahey et al., 2007a). In addition to the FARS scoring system, there is a modified scale that uses only the subgroups of FARS involving the functional abilities of the patient (the bulbar, upper limb, lower limb, and upright stability subcategories) (Patel et al., 2016). The mFARS rating scales are now widely used in FRDA studies, and has been shown to strengthen the overall construct of the rating system versus the original FARS system (Rummey et al., 2019). It is therefore proposed to measure absolute mFARS scores over the course of the trial and compare these scores to both baseline values and cohort-matched natural history data for all treated subjects to assess how this therapy improves overall neurological function.

Fine Motor Skills Assessment

In addition to using the mFARS rating scale to evaluate the effect of rAAVhu68.hFXN on neurological manifestations, further assessment of neurological symptoms are done by using the 9-hole peg test (9HPT). The 9HPT assesses fine motor skills by timing how long it takes for a subject to add pegs to a pegboard and remove them twice with each hand, beginning with their dominant hand. This assessment is validated and has been used in numerous FRDA trials to assess upper limb ambulation (Friedman et al., 2010; Patel et al., 2016; Lynch et al., 2019a; Lynch et al., 2019b). As patients from Stage 1 of the proposed trial may not be able to complete the 9HPT in <5 minutes, subjects in this cohort may instead perform an assessment that models use of a spoon, including the subject grasping, scooping, and transferring the spoon to their mouth, which also assesses upper limb motility but is an easier task for more severely affected subjects to perform (Nguyen et al., 2020). The endpoint is evaluated as a change from baseline in the timing of this task.

Ambulation

To assess the ability of rAAVhu68.hFXN to improve or stabilize ambulation in subjects with FRDA, this trial measures subject scores on the upright stability subsection of the mFARS assessment as a secondary key efficacy endpoint. The upright stability subset of the mFARS has been used to evaluate the progressive loss of ambulation in subjects with FRDA, as well as to predict the average time to loss of ambulation in early-, mid-, and late-onset FRDA disease types using natural history data (Rummey et al., 2020a; Rummey et al., 2020b). This subset evaluates subjects on many aspects of ambulation, including assessments for sitting, standing, and gait.

Given the recent publication using the FA-COMS natural history data to analyze upright stability and loss of ambulation, this endpoint would have available natural history to be used as a direct comparator. Furthermore, in a recent analysis of the test-retest ability of the mFARS assessment, the upright stability subset of assessments was shown to be the most reliable measure in terms of intra-patient consistency in the assessment over multiple time points (Rummey et al., 2020a; Rummey et al., 2020b). Additionally, as this measure is scored on a rubric with pre-established, discrete intervals, it is expected that in addition to the reliability of this assessment itself, this data also has less variability than walk tests, which, per key opinion leader advice, are more subjective in terms of both subject ability and interpretation of how the assessment is to be completed. Given the natural history data that exists for this endpoint, as well as its demonstrated ability to be reliably captured and accurately track changes in the loss of ambulation, this measure is the best assessment of ambulation over time and thus using this assessment as a secondary key efficacy endpoint in Stage 2 of this trial.

To further assess mobility and ambulation in subjects from Stage 2 of this trial, a 25-foot walk test is measured over time as an exploratory endpoint. This assessment measures the amount of time it takes for the subject to complete a 25-foot walk, is a well established measure of ambulation used frequently in FRDA, and has been demonstrated to model real world ambulation (Fahey et al., 2007b; Milne et al., 2014). This endpoint is evaluated in subjects enrolled in Stage 2 of this trial only, and tests the ability of rAAVhu68.hFXN to stabilize or improve ambulation in patients for whom are expected to show a decrease in ambulation with no treatment over the course of 2 years.

Dysarthria

To assess dysarthria in subjects over time in all cohorts over the course of the trial, speech analysis software developed by Redenlab in Queensland, Australia is utilized. This analysis involves subjects producing monosyllables or repeated syllable sounds, as well as, reading pre-defined passages out loud using an app available on devices such as a phone or tablet. The speech recording can then be sent for analysis by Renenlab specialists for different aspects of speech such as prosodic features (variation of pitch and loudness, maintenance of loudness, phrase length, general rate, and stress), respiratory features, phonatory features, resonance, articulatory features, and intelligibility (Folker et al., 2010; Vogel et al., 2017).

Furthermore, speech samples are also analyzed by the Assessment of Intelligibility of Dysarthria Speech criteria, encompassing features such as sentence intelligibility, total words per minute, and intelligible words per minute (Folker et al., 2010).

Cardiac Endpoints rAAVhu68.hFXN is evaluated via multiple cardiac endpoints, which are measured both relative to subject baseline and compared to cohort-matched natural history data. These assessments are able to demonstrate the ability of rAAVhu68.hFXN to address the cardiac symptoms seen in FRDA patients.

The following parameters are followed to assess the effects of rAAVhu68.hFXN on cardiac symptoms over the 5 year follow up of the study. An interim analysis of all cardiac endpoints is performed from data collected over the first 2 years of post-treatment follow up. A final evaluation of neurological endpoints is performed with data collected over the 5 year duration of the study.

Structural Endpoints

In order to monitor stabilization or improvement in structural cardiac parameters of the disease, echocardiograms are performed throughout the course of the trial. Additionally, cardiac MRI (cMRI) is performed at baseline and annually throughout the 5-year course of the trial to obtain more detailed structural information to assess efficacy of rAAvhu68.hFXN.

Echocardiograms and cMRI data is collected to assess the efficacy of rAAvhu68.hFXN in stabilizing or improving the cardiac symptoms of FRDA subjects. The first endpoint evaluates relative wall thickness (RWT), defined here as 2 times posterior wall thickness divided by the LV end-diastolic internal diameter (LVEDID), for each patient. Although many FRDA patients display concentric thickening of ventricles, studies of echocardiograms from FRDA patients demonstrate that increases in RWT were among the most common LV abnormalities in this patient population (St John Sutton et al., 2014; Peverill et al., 2019). This endpoint is assessed by data from echocardiograms and cMRIs at 2 years in all cohorts.

Another structural endpoint that shows cardiac abnormalities early in FRDA progression is longitudinal strain. Longitudinal strain is defined as the change in the left ventricular segment length divided by the resting segment length obtained at mid-cavity level. A study by St. John Sutton and colleagues found that longitudinal strain in FRDA patients was significantly decreased from that of non-FRDA control patients. This study also found that decrease in strain was constant over time in the FRDA patients, and was unchanged over the course of 3 years relative to baseline values (St John Sutton et al., 2014). Data collected at the 2 year time point and throughout the course of the trial is analyzed to evaluate whether longitudinal strain is changed with rAAvhu68.hFXN treatment.

In addition to measuring RWT and longitudinal strain, echocardiogram and cMRI data is used to evaluate changes in left ventricular ejection fraction (LVEF) over the course of the trial as an exploratory endpoint. While a decline in LVEF is a late indicator of disease burden, it has been demonstrated in longitudinal natural history data that there is a subset of patients at a high risk of cardiovascular events for which LVEF would decline over the planned duration of this study (Pousset et al., 2015b). Considering that the first two cohorts of this trial consist of FRDA patients at the highest risk of cardiac complications, LVEF is monitored over the course of the trial to see if treatment with rAAvhu68.hFXN prevents subjects from showing a decline in this parameter. This endpoint is evaluated at 2 years and calculated for all echocardiogram and cMRI measurements taken from all cohorts.

Electrocardiogram Endpoints

Electrocardiographic data is used in addition to the previously mentioned structural endpoint measures to further evaluate the efficacy of rAAvhu68.hFXN. Electrocardiograms (ECGs) for each subject are evaluated at each time point. While evaluating 12-lead ECGs is necessary for ongoing evaluation of the safety of rAAvhu68.hFXN, this data is also used to evaluate efficacy of rAAvhu68.hFXN. Specifically, changes in heart rate, R-R interval, PR interval, QRS interval, QT time and time corrected by Fridericia's formula (QTcF) are monitored. ECGs are monitored for abnormal findings, including non-specific ST-T wave changes, right axis deviation, left ventricular hypertrophy, right ventricular hypertrophy, as abnormalities in these ECG parameters have been observed in FRDA cohorts (Schadt et al., 2012). Furthermore, subjects are monitored for ventricular or supraventricular arrhythmias for all ECGs collected as proposed in the staging of cardiomyopathy criteria by (Weidemann et al., 2012). These parameters are monitored throughout the course of the trial and evaluated as an endpoint at the 2 year time point.

Other Cardiac Endpoints

To further assess efficacy of rAAvhu68.hFXN on cardiac parameters, monitoring for the absence of progression of cardiac symptoms, including ICD, heart failure hospitalization, and survival is performed continuously throughout the trial and reported at the conclusion of the study.

Quality of Life

In order to evaluate the ability of rAAvhu68.hFXN treatment to demonstrate an improvement in the quality of life of FRDA patients, the following quality of life assessments are evaluated as additional exploratory endpoints in all cohorts.

FARA PRO

An FRDA-specific patient-reported outcomes (PRO) measure is utilized to evaluate quality of life as an additional exploratory endpoint. This PRO is currently in development by the Friedreich's Ataxia Research Alliance (FARA) and is expected to be validated by the start of the proposed trial. In utilizing a measure that is specific to the concerns of FRDA patients as an endpoint in the proposed study, a more accurate measure in the improvements made to the lives of these patients can be obtained.

D. Intravenous Administration (FIH)

rAAvhu68.hFXN is administered via an IV infusion into a peripheral vein. The IV infusion rate is determined in the NHP nonclinical studies. For example, the rAAvhu68.hFXN is infused over no less than a 20-minute interval using a syringe infusion pump via an IV administration set. The interval can be prolonged to as much as 1 hour or longer if the investigator feels it is necessary to use a lower infusion rate. The IV infusion is performed first to allow for the observation of any hypersensitivity reactions to the gene product as well as other safety observations. This IV infusion occurs no longer than 24 hours prior to the IDN procedure occurring the following day.

Compatibility testing with the administration set and rAAvhu68.hFXN is performed. Variability in dosing levels can be caused by loss of the FDP through binding to plastics and other solid surfaces during vector storage and patient administration. Therefore, the clinically suitable surfactant Poloxamer 188 is a component of the final formulation buffer of the final rAAVhu68.hFXN formulation and is anticipated to minimize this type of loss. The interaction of the prepared final rAAVhu68.hFXN formulation with both the storage vial and the clinical IV and IDN devices is investigated to determine the amount of vector loss through binding to surfaces. For each of the delivery devices doses which bracket the anticipated doses for the clinical trial is prepared using an equivalent preparation process as used in the clinical trial. The prepared final rAAVhu68.hFXN formulation is passed through the each of the devices. GC titrations and potency assays are performed on pre-device and post-device samples. The appropriate number of replicates are included to assure statistical significance. Comparison of GC titers and potency pre- and post-device enables an assessment of final rAAvhu68.hFXN formulation loss administration to the patient. Parallel studies are also be performed in a similar way to assess the in-use stability rAAvhu68.hFXN formulation after preparation and storage in the delivery syringe.

E. Intraparenchymal (Dentate Nucleus) Injection Device

The devices that is used for the IDN injection are the ClearPoint® System and Accessories and Ventricular Cannula.

F. Dosing Regimen and Explanation of the Device Use by the Clinician

Following the IV infusion of rAAvhu68.hFXN, an IDN injection into each of the dentate nuclei of the cerebellum is performed as this is a major site of neurological pathology in FRDA. The direct injection procedure is performed early in the morning after the subject receives a dose by IV infusion the previous day using the ClearPoint® injection system. The ClearPoint® injection system consists of a monitor to visualize the brain and injection procedure in real time, a head fixation frame that is secured to the skull, and an MRI-compatible SmartFrame® trajectory device that enables MRI-guided alignment during the procedure. This system allows for the direct injection to be combined with real-time visualization of the injection tract by MRI. To enable visualization of vector distribution, the injection material containing the vector is be mixed with gadolinium (final concentration of 2 mM gadolinium). Proper precautions are taken with the gadolinium, including warning patients of the potential risks of gadolinium use and prolonged gadolinium retention for brain MRI in informed consent forms. Furthermore, patients for whom there are increased safety concerns with gadolinium use, such as women who are pregnant or those with kidney disease, are already excluded from participation in this trial.

During the direct injection procedure, the injection cannula is placed through the ClearPoint® frame to the correct position on the skull and the frame maintains the correct trajectory. The final position of the injection cannula is confirmed using real-time MRI images, and then the vector is injected into the parenchyma of the deep cerebellar nuclei using convection-enhanced delivery. Each subject receives administration of the rAAVhu68.hFXN plus gadolinium in each dentate nucleus injected at a rate of 0.5 μL/min initially, and then at an increased rate of up to 5 μL/min based on clinician discretion during the procedure. The procedure takes approximately 5-6 hours and the subjects are anesthetized for the duration of the procedure.

All documents cited in this specification are incorporated herein by reference, as is the priority application, U.S. Provisional Patent Application No. 62/950,834, filed Dec. 19, 2019. The Sequence Listing filed herewith, labeled 20-9217PCT_ST25.txt, and the sequences and text therein are incorporated by reference. While the invention has been described with reference to particular embodiments, it will be appreciated that modifications can be made without departing from the spirit of the invention. Such modifications are intended to fall within the scope of the appended claims.

(Sequence Listing Free Text)

The following information is provided for sequences containing free text under numeric identifier <223>.

| SEQ ID NO: (containing free text) | Free text under <223> |
|---|---|
| 3 | <223> Engineered hFXN coding sequence |
| 8 | <223> CB7.CI.hFXNco |
| | <220> |
| | <221> repeat_region |
| | <222> (1) . . . (130) |
| | <223> 5'ITR |
| | <220> |
| | <221> promoter |
| | <222> (198) . . . (579) |
| | <223> CMV IE promoter |
| | <220> |
| | <221> promoter |
| | <222> (582) . . . (863) |
| | <223> CB promoter |
| | <220> |
| | <221> TATA_signal |
| | <222> (836) . . . (838) |
| | <220> |
| | <221> Intron |
| | <222> (958) . . . (1930) |
| | <220> |
| | <221> misc_feature |
| | <222> (1942) . . . (2572) |
| | <223> human FXN |
| | <220> |
| | <221> polyA_signal |
| | <222> (2611) . . . (2737) |
| | <223> Rabbit globin polyA |
| | <220> |
| | <221> repeat_unit |
| | <222> (2826) . . . (2955) |
| | <223> 3' ITR |

-continued

-continued

| SEQ ID NO: (containing free text) | Free text under <223> |
|---|---|
| 11 | <223> AAVrh.91 |
| 12 | <223> vector genome AAV.CB7.CI.hFXNco.RBG<br><220><br><221> repeat_region<br><222> (1) . . . (130)<br><223> 5'ITR<br><220><br><221> repeat_region<br><222> (198) . . . (579)<br><223> CMV IE enhancer<br><220><br><221> promoter<br><222> (585) . . . (862)<br><223> Chicken beta-actin promoter<br><220><br><221> TATA_signal<br><222> (836) . . . (862)<br><223> TATA<br><220> |

| SEQ ID NO: (containing free text) | Free text under <223> |
|---|---|
| | <221> Intron<br><222> (957) . . . (1929)<br><223> chicken beta-actin intron<br><220><br><221> Intron<br><222> (957) . . . (1929)<br><223> chimeric intron<br><220><br><221> misc_feature<br><222> (1941) . . . (2570)<br><223> hFXNco<br><220><br><221> polyA_signal<br><222> (2610) . . . (2736)<br><223> Rabbit globin poly A<br><220><br><221> repeat_region<br><222> (2825) . . . (2954)<br><223> 3'ITR |

The invention claimed is:

1. A recombinant adeno-associated virus (rAAV) having an AAV capsid and a vector genome comprising a FXN gene having the sequence of SEQ ID NO: 3 or a sequence 95% identical thereto that encodes human frataxin protein having amino acid sequence of SEQ ID NO: 2, and regulatory sequences which direct expression of the FXN gene in targeted human cells.

2. The rAAV according to claim 1, wherein the vector genome comprises an AAV2 5' inverted terminal repeat (ITR), a CB7 promoter comprising a cytomegalovirus immediate early (CMV IE) enhancer, a chicken beta-actin promoter, a chimeric intron comprising a chicken beta actin splice donor and a rabbit beta-globin splice acceptor element, the FXN gene, a polyA, and an AAV2 3' ITR, optionally comprising the sequence of nucleotides 198 to 2737 of SEQ ID NO: 8 or nucleotides 198 to 2736 of SEQ ID NO: 12.

3. The rAAV according to claim 1, wherein the vector genome further comprises at least one, at least two, or at least three tandem repeats of dorsal root ganglion (DRG)-specific miRNA targeted sequences.

4. The rAAV according to claim 3, wherein the at least two or at least three miRNA target sequences are the same.

5. The rAAV according to claim 1, wherein the AAV capsid is an AAVrh91 capsid.

6. The rAAV according to claim 1, wherein the AAV capsid is an AAV clade F capsid.

7. The rAAV according to claim 6, wherein the clade F capsid is an AAVhu68 capsid.

8. An aqueous pharmaceutical composition comprising a formulation buffer and a stock of the rAAV according to claim 1.

9. The pharmaceutical composition according to claim 8, wherein the formulation buffer comprises:

an artificial cerebrospinal fluid comprising buffered saline and one or more of sodium, calcium, magnesium, potassium, or mixtures thereof, and
a surfactant.

10. The pharmaceutical composition according to claim 9, wherein the surfactant is present at 0.0005% w/w to about 0.001% w/w of the pharmaceutical composition.

11. The pharmaceutical composition according to claim 8, wherein the composition is at a pH in the range of 7.5 to 7.8, or 6.2 to 7.7, or about 7.

12. A regimen comprising dual-route of administration of rAAV, the regimen comprising intravenous administration of a first rAAV according to claim 1 and intraparenchymal (dentate nucleus) administration of a second rAAV according to claim 1.

13. The regimen according to claim 12, wherein the intraparenchymal (dentate nucleus) administration is performed unilaterally.

14. The regimen according to claim 12, wherein the intraparenchymal (dentate nucleus) administration is performed bilaterally.

15. The regimen according to claim 12 wherein the intravenous and intraparenchymal (dentate nucleus) administrations of the rAAV are performed sequentially and within a 24-hour period.

16. A regimen comprising co-administration of a first rAAV according to claim 1 intravenously and a second rAAV according to claim 1 intrathecally.

17. A method of treating FRDA in a subject with FRDA, the method comprising administering the pharmaceutical composition according to claim 8 to the subject.

18. A plasmid comprising an expression cassette comprising a FXN gene having the sequence of SEQ ID NO: 3 or a sequence 95% identical thereto that encodes human frataxin protein having amino acid sequence of SEQ ID NO: 2.

19. A plasmid comprising the vector genome of SEQ ID NO: 8 or 12, or a sequence at least 95% identical to SEQ ID NO: 8 or 12.

20. A host cell comprising the plasmid according to claim 18.

21. The rAAV according to claim 1, wherein the FXN gene comprises a sequence of SEQ ID NO: 3.

22. The plasmid according to claim 18, wherein the FXN gene comprises a sequence of SEQ ID NO: 3.

* * * * *

SEQUENCE LISTING

<160> NUMBER OF SEQ ID NOS: 12

<210> SEQ ID NO 1
<211> LENGTH: 630
<212> TYPE: DNA
<213> ORGANISM: Homo sapiens
<220> FEATURE:
<221> NAME/KEY: CDS
<222> LOCATION: (1)..(630)

<400> SEQUENCE: 1

```
atg tgg act ctc ggg cgc cgc gca gta gcc ggc ctc ctg gcg tca ccc       48
Met Trp Thr Leu Gly Arg Arg Ala Val Ala Gly Leu Leu Ala Ser Pro
1               5                   10                  15 agc cca gcc cag gcc cag acc ctc acc cgg gtc ccg cgg ccg gca gag       96
Ser Pro Ala Gln Ala Gln Thr Leu Thr Arg Val Pro Arg Pro Ala Glu
                20                  25                  30 ttg gcc cca ctc tgc ggc cgc cgt ggc ctg cgc acc gac atc gat gcg      144
Leu Ala Pro Leu Cys Gly Arg Arg Gly Leu Arg Thr Asp Ile Asp Ala
            35                  40                  45 acc tgc acg ccc cgc cgc gca agt tcg aac caa cgt ggc ctc aac cag      192
Thr Cys Thr Pro Arg Arg Ala Ser Ser Asn Gln Arg Gly Leu Asn Gln
        50                  55                  60 att tgg aat gtc aaa aag cag agt gtc tat ttg atg aat ttg agg aaa      240
Ile Trp Asn Val Lys Lys Gln Ser Val Tyr Leu Met Asn Leu Arg Lys
65                  70                  75                  80 tct gga act ttg ggc cac cca ggc tct cta gat gag acc acc tat gaa      288
Ser Gly Thr Leu Gly His Pro Gly Ser Leu Asp Glu Thr Thr Tyr Glu
                85                  90                  95 aga cta gca gag gaa acg ctg gac tct tta gca gag ttt ttt gaa gac      336
Arg Leu Ala Glu Glu Thr Leu Asp Ser Leu Ala Glu Phe Phe Glu Asp
                100                 105                 110 ctt gca gac aag cca tac acg ttt gag gac tat gat gtc tcc ttt ggg      384
Leu Ala Asp Lys Pro Tyr Thr Phe Glu Asp Tyr Asp Val Ser Phe Gly
            115                 120                 125 agt ggt gtc tta act gtc aaa ctg ggt gga gat cta gga acc tat gtg      432
Ser Gly Val Leu Thr Val Lys Leu Gly Gly Asp Leu Gly Thr Tyr Val
        130                 135                 140
```

```
atc aac aag cag acg cca aac aag caa atc tgg cta tct tct cca tcc      480
Ile Asn Lys Gln Thr Pro Asn Lys Gln Ile Trp Leu Ser Ser Pro Ser
145             150                 155                 160 agt gga cct aag cgt tat gac tgg act ggg aaa aac tgg gtg tac tcc      528
Ser Gly Pro Lys Arg Tyr Asp Trp Thr Gly Lys Asn Trp Val Tyr Ser
                165                 170                 175 cac gac ggc gtg tcc ctc cat gag ctg ctg gcc gca gag ctc act aaa      576
His Asp Gly Val Ser Leu His Glu Leu Leu Ala Ala Glu Leu Thr Lys
                180                 185                 190 gcc tta aaa acc aaa ctg gac ttg tct tcc ttg gcc tat tcc gga aaa      624
Ala Leu Lys Thr Lys Leu Asp Leu Ser Ser Leu Ala Tyr Ser Gly Lys
            195                 200                 205 gat gct                                                               630
Asp Ala
    210
```

<210> SEQ ID NO 2
<211> LENGTH: 210
<212> TYPE: PRT
<213> ORGANISM: Homo sapiens

<400> SEQUENCE: 2

```
Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
                20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
        50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
                100                 105                 110

Leu Ala Asp Lys Pro Tyr Thr Phe Glu Asp Tyr Asp Val Ser Phe Gly
            115                 120                 125

Ser Gly Val Leu Thr Val Lys Leu Gly Gly Asp Leu Gly Thr Tyr Val
        130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
                180                 185                 190

Ala Leu Lys Thr Lys Leu Asp Leu Ser Ser Leu Ala Tyr Ser Gly Lys
            195                 200                 205

Asp Ala
    210
```

<210> SEQ ID NO 3
<211> LENGTH: 630
<212> TYPE: DNA
<213> ORGANISM: Artificial Sequence
<220> FEATURE:
<223> OTHER INFORMATION: Engineered hFXN coding sequence

<400> SEQUENCE: 3

```
atgtggacac ttggccgcag agctgttgct ggcctgcttg cttctccatc tcccgctcaa      60
gcccagacac tgaccagagt gcctagacct gctgaactgg cccctctgtg tggcagaaga     120
ggcctgagaa ccgacatcga cgccacatgc acacctagaa gggccagcag caatcagcgg     180
ggcctgaatc agatctggaa cgtgaagaaa cagagcgtgt acctgatgaa cctgagaaag     240
agcggcaccc tgggacaccc tggaagcctg gacgagacaa cctacgagag actggccgag     300
gaaaccctgg attccctggc cgagttcttc gaggacctgg ccgataagcc ctacaccttc     360
gaggattacg acgtgtcctt tggcagcggc gtgctgacag tgaaactcgg cggagatctg     420
ggcacctacg tgatcaacaa gcagacccct aacaaacaga tctggctgag cagccctagc     480
agcggcccca agagatacga ttggaccggc aagaactggg tgtacagcca cgacggcgtg     540
tccctgcacg aactgctggc tgccgaactg acaaaggccc tgaaaacaaa gctggacctg     600
tccagcctgg cctactctgg caaggatgcc                                     630
```

```
<210> SEQ ID NO 4
<211> LENGTH: 2211
<212> TYPE: DNA
<213> ORGANISM: adeno-associated virus 68
<220> FEATURE:
<221> NAME/KEY: CDS
<222> LOCATION: (1)..(2211)

<400> SEQUENCE: 4
```

```
atg gct gcc gat ggt tat ctt cca gat tgg ctc gag gac aac ctc agt      48
Met Ala Ala Asp Gly Tyr Leu Pro Asp Trp Leu Glu Asp Asn Leu Ser
1               5                   10                  15 gaa ggc att cgc gag tgg tgg gct ttg aaa cct gga gcc cct caa ccc      96
Glu Gly Ile Arg Glu Trp Trp Ala Leu Lys Pro Gly Ala Pro Gln Pro
            20                  25                  30 aag gca aat caa caa cat caa gac aac gct cgg ggt ctt gtg ctt ccg     144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg     192
Gly Tyr Lys Tyr Leu Gly Pro Gly Asn Gly Leu Asp Lys Gly Glu Pro
    50                  55                  60 gtc aac gaa gca gac gcg gcg gcc ctc gag cac gac aag gcc tac gac     240
Val Asn Glu Ala Asp Ala Ala Ala Leu Glu His Asp Lys Ala Tyr Asp
65                  70                  75                  80 cag cag ctc aag gcc gga gac aac ccg tac ctc aag tac aac cac gcc     288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc     336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct     384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg     432
Leu Gly Leu Val Glu Glu Ala Ala Lys Thr Ala Pro Gly Lys Lys Arg
    130                 135                 140 cct gta gag cag tct cct cag gaa ccg gac tcc tcc gtg ggt att ggc     480
Pro Val Glu Gln Ser Pro Gln Glu Pro Asp Ser Ser Val Gly Ile Gly
145                 150                 155                 160 aaa tcg ggt gca cag ccc gct aaa aag aga ctc aat ttc ggt cag act     528
Lys Ser Gly Ala Gln Pro Ala Lys Lys Arg Leu Asn Phe Gly Gln Thr
                165                 170                 175 ggc gac aca gag tca gtc ccc gac cct caa cca atc gga gaa cct ccc     576
```

-continued

```
Gly Asp Thr Glu Ser Val Pro Asp Pro Gln Pro Ile Gly Glu Pro Pro
        180             185             190 gca gcc ccc tca ggt gtg gga tct ctt aca atg gct tca ggt ggt ggc     624
Ala Ala Pro Ser Gly Val Gly Ser Leu Thr Met Ala Ser Gly Gly Gly
        195             200             205 gca cca gtg gca gac aat aac gaa ggt gcc gat gga gtg ggt agt tcc     672
Ala Pro Val Ala Asp Asn Asn Glu Gly Ala Asp Gly Val Gly Ser Ser
210             215             220 tcg gga aat tgg cat tgc gat tcc caa tgg ctg ggg gac aga gtc atc     720
Ser Gly Asn Trp His Cys Asp Ser Gln Trp Leu Gly Asp Arg Val Ile
225             230             235             240 acc acc agc acc cga acc tgg gcc ctg ccc acc tac aac aat cac ctc     768
Thr Thr Ser Thr Arg Thr Trp Ala Leu Pro Thr Tyr Asn Asn His Leu
                245             250             255 tac aag caa atc tcc aac agc aca tct gga gga tct tca aat gac aac     816
Tyr Lys Gln Ile Ser Asn Ser Thr Ser Gly Gly Ser Ser Asn Asp Asn
                260             265             270 gcc tac ttc ggc tac agc acc ccc tgg ggg tat ttt gac ttc aac aga     864
Ala Tyr Phe Gly Tyr Ser Thr Pro Trp Gly Tyr Phe Asp Phe Asn Arg
                275             280             285 ttc cac tgc cac ttc tca cca cgt gac tgg caa aga ctc atc aac aac     912
Phe His Cys His Phe Ser Pro Arg Asp Trp Gln Arg Leu Ile Asn Asn
        290             295             300 aac tgg gga ttc cgg cct aag cga ctc aac ttc aag ctc ttc aac att     960
Asn Trp Gly Phe Arg Pro Lys Arg Leu Asn Phe Lys Leu Phe Asn Ile
305             310             315             320 cag gtc aaa gag gtt acg gac aac aat gga gtc aag acc atc gct aat    1008
Gln Val Lys Glu Val Thr Asp Asn Asn Gly Val Lys Thr Ile Ala Asn
                325             330             335 aac ctt acc agc acg gtc cag gtc ttc acg gac tca gac tat cag ctc    1056
Asn Leu Thr Ser Thr Val Gln Val Phe Thr Asp Ser Asp Tyr Gln Leu
                340             345             350 ccg tac gtg ctc ggg tcg gct cac gag ggc tgc ctc ccg ccg ttc cca    1104
Pro Tyr Val Leu Gly Ser Ala His Glu Gly Cys Leu Pro Pro Phe Pro
                355             360             365 gcg gac gtt ttc atg att cct cag tac ggg tat cta acg ctt aat gat    1152
Ala Asp Val Phe Met Ile Pro Gln Tyr Gly Tyr Leu Thr Leu Asn Asp
        370             375             380 gga agc caa gcc gtg ggt cgt tcg tcc ttt tac tgc ctg gaa tat ttc    1200
Gly Ser Gln Ala Val Gly Arg Ser Ser Phe Tyr Cys Leu Glu Tyr Phe
385             390             395             400 ccg tcg caa atg cta aga acg ggt aac aac ttc cag ttc agc tac gag    1248
Pro Ser Gln Met Leu Arg Thr Gly Asn Asn Phe Gln Phe Ser Tyr Glu
                405             410             415 ttt gag aac gta cct ttc cat agc agc tat gct cac agc caa agc ctg    1296
Phe Glu Asn Val Pro Phe His Ser Ser Tyr Ala His Ser Gln Ser Leu
                420             425             430 gac cga ctc atg aat cca ctc atc gac caa tac ttg tac tat ctc tca    1344
Asp Arg Leu Met Asn Pro Leu Ile Asp Gln Tyr Leu Tyr Tyr Leu Ser
        435             440             445 aag act att aac ggt tct gga cag aat caa caa acg cta aaa ttc agt    1392
Lys Thr Ile Asn Gly Ser Gly Gln Asn Gln Gln Thr Leu Lys Phe Ser
        450             455             460 gtg gcc gga ccc agc aac atg gct gtc cag gga aga aac tac ata cct    1440
Val Ala Gly Pro Ser Asn Met Ala Val Gln Gly Arg Asn Tyr Ile Pro
465             470             475             480 gga ccc agc tac cga caa caa cgt gtc tca acc act gtg act caa aac    1488
Gly Pro Ser Tyr Arg Gln Gln Arg Val Ser Thr Thr Val Thr Gln Asn
                485             490             495
```

-continued

```
aac aac agc gaa ttt gct tgg cct gga gct tct tct tgg gct ctc aat      1536
Asn Asn Ser Glu Phe Ala Trp Pro Gly Ala Ser Ser Trp Ala Leu Asn
            500                 505                 510 gga cgt aat agc ttg atg aat cct gga cct gct atg gcc agc cac aaa      1584
Gly Arg Asn Ser Leu Met Asn Pro Gly Pro Ala Met Ala Ser His Lys
            515                 520                 525 gaa gga gag gac cgt ttc ttt cct ttg tct gga tct tta att ttt ggc      1632
Glu Gly Glu Asp Arg Phe Phe Pro Leu Ser Gly Ser Leu Ile Phe Gly
            530                 535                 540 aaa caa gga act gga aga gac aac gtg gat gcg gac aaa gtc atg ata      1680
Lys Gln Gly Thr Gly Arg Asp Asn Val Asp Ala Asp Lys Val Met Ile
545                 550                 555                 560 acc aac gaa gaa gaa att aaa act acc aac cca gta gca acg gag tcc      1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag      1776
Tyr Gly Gln Val Ala Thr Asn His Gln Ser Ala Gln Ala Gln Ala Gln
                580                 585                 590 acc ggc tgg gtt caa aac caa gga ata ctt ccg ggt atg gtt tgg cag      1824
Thr Gly Trp Val Gln Asn Gln Gly Ile Leu Pro Gly Met Val Trp Gln
            595                 600                 605 gac aga gat gtg tac ctg caa gga ccc att tgg gcc aaa att cct cac      1872
Asp Arg Asp Val Tyr Leu Gln Gly Pro Ile Trp Ala Lys Ile Pro His
            610                 615                 620 acg gac ggc aac ttt cac cct tct ccg ctg atg gga ggg ttt gga atg      1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg      1968
Lys His Pro Pro Pro Gln Ile Leu Ile Lys Asn Thr Pro Val Pro Ala
                645                 650                 655 gat cct cca acg gct ttc aac aag gac aag ctg aac tct ttc atc acc      2016
Asp Pro Pro Thr Ala Phe Asn Lys Asp Lys Leu Asn Ser Phe Ile Thr
            660                 665                 670 cag tat tct act ggc caa gtc agc gtg gag att gag tgg gag ctg cag      2064
Gln Tyr Ser Thr Gly Gln Val Ser Val Glu Ile Glu Trp Glu Leu Gln
            675                 680                 685 aag gaa aac agc aag cgc tgg aac ccg gag atc cag tac act tcc aac      2112
Lys Glu Asn Ser Lys Arg Trp Asn Pro Glu Ile Gln Tyr Thr Ser Asn
            690                 695                 700 tat tac aag tct aat aat gtt gaa ttt gct gtt aat act gaa ggt gtt      2160
Tyr Tyr Lys Ser Asn Asn Val Glu Phe Ala Val Asn Thr Glu Gly Val
705                 710                 715                 720 tat tct gaa ccc cgc ccc att ggc acc aga tac ctg act cgt aat ctg      2208
Tyr Ser Glu Pro Arg Pro Ile Gly Thr Arg Tyr Leu Thr Arg Asn Leu
                725                 730                 735 taa                                                                  2211
```

```
<210> SEQ ID NO 5
<211> LENGTH: 736
<212> TYPE: PRT
<213> ORGANISM: adeno-associated virus 68

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45
```

-continued

```
Gly Tyr Lys Tyr Leu Gly Pro Gly Asn Gly Leu Asp Lys Gly Glu Pro
    50              55                  60

Val Asn Glu Ala Asp Ala Ala Ala Leu Glu His Asp Lys Ala Tyr Asp
65              70                  75                  80

Gln Gln Leu Lys Ala Gly Asp Asn Pro Tyr Leu Lys Tyr Asn His Ala
            85              90                  95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Leu Leu Glu Pro
            115             120             125

Leu Gly Leu Val Glu Glu Ala Ala Lys Thr Ala Pro Gly Lys Lys Arg
    130             135             140

Pro Val Glu Gln Ser Pro Gln Glu Pro Asp Ser Ser Val Gly Ile Gly
145             150             155             160

Lys Ser Gly Ala Gln Pro Ala Lys Lys Arg Leu Asn Phe Gly Gln Thr
            165             170             175

Gly Asp Thr Glu Ser Val Pro Asp Pro Gln Pro Ile Gly Glu Pro Pro
            180             185             190

Ala Ala Pro Ser Gly Val Gly Ser Leu Thr Met Ala Ser Gly Gly Gly
            195             200             205

Ala Pro Val Ala Asp Asn Asn Glu Gly Ala Asp Gly Val Gly Ser Ser
    210             215             220

Ser Gly Asn Trp His Cys Asp Ser Gln Trp Leu Gly Asp Arg Val Ile
225             230             235             240

Thr Thr Ser Thr Arg Thr Trp Ala Leu Pro Thr Tyr Asn Asn His Leu
            245             250             255

Tyr Lys Gln Ile Ser Asn Ser Thr Ser Gly Gly Ser Ser Asn Asp Asn
            260             265             270

Ala Tyr Phe Gly Tyr Ser Thr Pro Trp Gly Tyr Phe Asp Phe Asn Arg
            275             280             285

Phe His Cys His Phe Ser Pro Arg Asp Trp Gln Arg Leu Ile Asn Asn
    290             295             300

Asn Trp Gly Phe Arg Pro Lys Arg Leu Asn Phe Lys Leu Phe Asn Ile
305             310             315             320

Gln Val Lys Glu Val Thr Asp Asn Asn Gly Val Lys Thr Ile Ala Asn
            325             330             335

Asn Leu Thr Ser Thr Val Gln Val Phe Thr Asp Ser Asp Tyr Gln Leu
            340             345             350

Pro Tyr Val Leu Gly Ser Ala His Glu Gly Cys Leu Pro Pro Phe Pro
            355             360             365

Ala Asp Val Phe Met Ile Pro Gln Tyr Gly Tyr Leu Thr Leu Asn Asp
    370             375             380

Gly Ser Gln Ala Val Gly Arg Ser Ser Phe Tyr Cys Leu Glu Tyr Phe
385             390             395             400

Pro Ser Gln Met Leu Arg Thr Gly Asn Asn Phe Gln Phe Ser Tyr Glu
            405             410             415

Phe Glu Asn Val Pro Phe His Ser Ser Tyr Ala His Ser Gln Ser Leu
            420             425             430

Asp Arg Leu Met Asn Pro Leu Ile Asp Gln Tyr Leu Tyr Tyr Leu Ser
            435             440             445

Lys Thr Ile Asn Gly Ser Gly Gln Asn Gln Gln Thr Leu Lys Phe Ser
    450             455             460

Val Ala Gly Pro Ser Asn Met Ala Val Gln Gly Arg Asn Tyr Ile Pro
```

-continued

```
465            470            475            480

Gly Pro Ser Tyr Arg Gln Gln Arg Val Ser Thr Thr Val Thr Gln Asn
                485                490                495

Asn Asn Ser Glu Phe Ala Trp Pro Gly Ala Ser Ser Trp Ala Leu Asn
            500                505                510

Gly Arg Asn Ser Leu Met Asn Pro Gly Pro Ala Met Ala Ser His Lys
            515                520                525

Glu Gly Glu Asp Arg Phe Phe Pro Leu Ser Gly Ser Leu Ile Phe Gly
            530                535                540

Lys Gln Gly Thr Gly Arg Asp Asn Val Asp Ala Asp Lys Val Met Ile
545                550                555                560

Thr Asn Glu Glu Glu Ile Lys Thr Thr Asn Pro Val Ala Thr Glu Ser
                565                570                575

Tyr Gly Gln Val Ala Thr Asn His Gln Ser Ala Gln Ala Gln Ala Gln
                580                585                590

Thr Gly Trp Val Gln Asn Gln Gly Ile Leu Pro Gly Met Val Trp Gln
                595                600                605

Asp Arg Asp Val Tyr Leu Gln Gly Pro Ile Trp Ala Lys Ile Pro His
            610                615                620

Thr Asp Gly Asn Phe His Pro Ser Pro Leu Met Gly Gly Phe Gly Met
625                630                635                640

Lys His Pro Pro Pro Gln Ile Leu Ile Lys Asn Thr Pro Val Pro Ala
                645                650                655

Asp Pro Pro Thr Ala Phe Asn Lys Asp Lys Leu Asn Ser Phe Ile Thr
                660                665                670

Gln Tyr Ser Thr Gly Gln Val Ser Val Glu Ile Glu Trp Glu Leu Gln
            675                680                685

Lys Glu Asn Ser Lys Arg Trp Asn Pro Glu Ile Gln Tyr Thr Ser Asn
            690                695                700

Tyr Tyr Lys Ser Asn Asn Val Glu Phe Ala Val Asn Thr Glu Gly Val
705                710                715                720

Tyr Ser Glu Pro Arg Pro Ile Gly Thr Arg Tyr Leu Thr Arg Asn Leu
                725                730                735
```

<210> SEQ ID NO 6
<211> LENGTH: 2208
<212> TYPE: DNA
<213> ORGANISM: adeno-associated virus 9
<220> FEATURE:
<221> NAME/KEY: CDS
<222> LOCATION: (1)..(2208)
<223> OTHER INFORMATION: AAV9 VP1 Capsid

<400> SEQUENCE: 6

```
atg gct gcc gat ggt tat ctt cca gat tgg ctc gag gac aac ctt agt      48
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc      96
Glu Gly Ile Arg Glu Trp Trp Ala Leu Lys Pro Gly Ala Pro Gln Pro
                20                  25                  30 aag gca aat caa caa cat caa gac aac gct cga ggt ctt gtg ctt ccg     144
Lys Ala Asn Gln Gln His Gln Asp Asn Ala Arg Gly Leu Val Leu Pro
            35                  40                  45 ggt tac aaa tac ctt gga ccc ggc aac gga ctc gac aag ggg gag ccg     192
Gly Tyr Lys Tyr Leu Gly Pro Gly Asn Gly Leu Asp Lys Gly Glu Pro
        50                  55                  60 gtc aac gca gca gac gcg gcg gcc ctc gag cac gac aag gcc tac gac     240
```

-continued

```
Val Asn Ala Ala Asp Ala Ala Leu Glu His Asp Lys Ala Tyr Asp
65               70              75              80 cag cag ctc aag gcc gga gac aac ccg tac ctc aag tac aac cac gcc      288
Gln Gln Leu Lys Ala Gly Asp Asn Pro Tyr Leu Lys Tyr Asn His Ala
                85              90              95 gac gcc gag ttc cag gag cgg ctc aaa gaa gat acg tct ttt ggg ggc      336
Asp Ala Glu Phe Gln Glu Arg Leu Lys Glu Asp Thr Ser Phe Gly Gly
            100             105             110 aac ctc ggg cga gca gtc ttc cag gcc aaa aag agg ctt ctt gaa cct      384
Asn Leu Gly Arg Ala Val Phe Gln Ala Lys Lys Arg Leu Leu Glu Pro
            115             120             125 ctt ggt ctg gtt gag gaa gcg gct aag acg gct cct gga aag aag agg      432
Leu Gly Leu Val Glu Glu Ala Ala Lys Thr Ala Pro Gly Lys Lys Arg
        130             135             140 cct gta gag cag tct cct cag gaa ccg gac tcc tcc gcg ggt att ggc      480
Pro Val Glu Gln Ser Pro Gln Glu Pro Asp Ser Ser Ala Gly Ile Gly
145             150             155             160 aaa tcg ggt gca cag ccc gct aaa aag aga ctc aat ttc ggt cag act      528
Lys Ser Gly Ala Gln Pro Ala Lys Lys Arg Leu Asn Phe Gly Gln Thr
                165             170             175 ggc gac aca gag tca gtc cca gac cct caa cca atc gga gaa cct ccc      576
Gly Asp Thr Glu Ser Val Pro Asp Pro Gln Pro Ile Gly Glu Pro Pro
            180             185             190 gca gcc ccc tca ggt gtg gga tct ctt aca atg gct tca ggt ggt ggc      624
Ala Ala Pro Ser Gly Val Gly Ser Leu Thr Met Ala Ser Gly Gly Gly
            195             200             205 gca cca gtg gca gac aat aac gaa ggt gcc gat gga gtg ggt agt tcc      672
Ala Pro Val Ala Asp Asn Asn Glu Gly Ala Asp Gly Val Gly Ser Ser
        210             215             220 tcg gga aat tgg cat tgc gat tcc caa tgg ctg ggg gac aga gtc atc      720
Ser Gly Asn Trp His Cys Asp Ser Gln Trp Leu Gly Asp Arg Val Ile
225             230             235             240 acc acc agc acc cga acc tgg gcc ctg ccc acc tac aac aat cac ctc      768
Thr Thr Ser Thr Arg Thr Trp Ala Leu Pro Thr Tyr Asn Asn His Leu
                245             250             255 tac aag caa atc tcc aac agc aca tct gga gga tct tca aat gac aac      816
Tyr Lys Gln Ile Ser Asn Ser Thr Ser Gly Gly Ser Ser Asn Asp Asn
                260             265             270 gcc tac ttc ggc tac agc acc ccc tgg ggg tat ttt gac ttc aac aga      864
Ala Tyr Phe Gly Tyr Ser Thr Pro Trp Gly Tyr Phe Asp Phe Asn Arg
            275             280             285 ttc cac tgc cac ttc tca cca cgt gac tgg cag cga ctc atc aac aac      912
Phe His Cys His Phe Ser Pro Arg Asp Trp Gln Arg Leu Ile Asn Asn
        290             295             300 aac tgg gga ttc cgg cct aag cga ctc aac ttc aag ctc ttc aac att      960
Asn Trp Gly Phe Arg Pro Lys Arg Leu Asn Phe Lys Leu Phe Asn Ile
305             310             315             320 cag gtc aaa gag gtt acg gac aac aat gga gtc aag acc atc gcc aat     1008
Gln Val Lys Glu Val Thr Asp Asn Asn Gly Val Lys Thr Ile Ala Asn
                325             330             335 aac ctt acc agc acg gtc cag gtc ttc acg gac tca gac tat cag ctc     1056
Asn Leu Thr Ser Thr Val Gln Val Phe Thr Asp Ser Asp Tyr Gln Leu
            340             345             350 ccg tac gtg ctc ggg tcg gct cac gag ggc tgc ctc ccg ccg ttc cca     1104
Pro Tyr Val Leu Gly Ser Ala His Glu Gly Cys Leu Pro Pro Phe Pro
            355             360             365 gcg gac gtt ttc atg att cct cag tac ggg tat ctg acg ctt aat gat     1152
Ala Asp Val Phe Met Ile Pro Gln Tyr Gly Tyr Leu Thr Leu Asn Asp
        370             375             380
```

```
gga agc cag gcc gtg ggt cgt tcg tcc ttt tac tgc ctg gaa tat ttc          1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag          1248
Pro Ser Gln Met Leu Arg Thr Gly Asn Asn Phe Gln Phe Ser Tyr Glu
                405                 410                 415 ttt gag aac gta cct ttc cat agc agc tac gct cac agc caa agc ctg          1296
Phe Glu Asn Val Pro Phe His Ser Ser Tyr Ala His Ser Gln Ser Leu
                420                 425                 430 gac cga cta atg aat cca ctc atc gac caa tac ttg tac tat ctc tca          1344
Asp Arg Leu Met Asn Pro Leu Ile Asp Gln Tyr Leu Tyr Tyr Leu Ser
                435                 440                 445 aag act att aac ggt tct gga cag aat caa caa acg cta aaa ttc agt          1392
Lys Thr Ile Asn Gly Ser Gly Gln Asn Gln Gln Thr Leu Lys Phe Ser
                450                 455                 460 gtg gcc gga ccc agc aac atg gct gtc cag gga aga aac tac ata cct          1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac          1488
Gly Pro Ser Tyr Arg Gln Gln Arg Val Ser Thr Thr Val Thr Gln Asn
                485                 490                 495 aac aac agc gaa ttt gct tgg cct gga gct tct tct tgg gct ctc aat          1536
Asn Asn Ser Glu Phe Ala Trp Pro Gly Ala Ser Ser Trp Ala Leu Asn
                500                 505                 510 gga cgt aat agc ttg atg aat cct gga cct gct atg gcc agc cac aaa          1584
Gly Arg Asn Ser Leu Met Asn Pro Gly Pro Ala Met Ala Ser His Lys
                515                 520                 525 gaa gga gag gac cgt ttc ttt cct ttg tct gga tct tta att ttt ggc          1632
Glu Gly Glu Asp Arg Phe Phe Pro Leu Ser Gly Ser Leu Ile Phe Gly
                530                 535                 540 aaa caa gga act gga aga gac aac gtg gat gcg gac aaa gtc atg ata          1680
Lys Gln Gly Thr Gly Arg Asp Asn Val Asp Ala Asp Lys Val Met Ile
545                 550                 555                 560 acc aac gaa gaa gaa att aaa act act aac ccg gta gca acg gag tcc          1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag          1776
Tyr Gly Gln Val Ala Thr Asn His Gln Ser Ala Gln Ala Gln Ala Gln
                580                 585                 590 acc ggc tgg gtt caa aac caa gga ata ctt ccg ggt atg gtt tgg cag          1824
Thr Gly Trp Val Gln Asn Gln Gly Ile Leu Pro Gly Met Val Trp Gln
                595                 600                 605 gac aga gat gtg tac ctg caa gga ccc att tgg gcc aaa att cct cac          1872
Asp Arg Asp Val Tyr Leu Gln Gly Pro Ile Trp Ala Lys Ile Pro His
                610                 615                 620 acg gac ggc aac ttt cac cct tct ccg ctg atg gga ggg ttt gga atg          1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg          1968
Lys His Pro Pro Pro Gln Ile Leu Ile Lys Asn Thr Pro Val Pro Ala
                645                 650                 655 gat cct cca acg gcc ttc aac aag gac aag ctg aac tct ttc atc acc          2016
Asp Pro Pro Thr Ala Phe Asn Lys Asp Lys Leu Asn Ser Phe Ile Thr
                660                 665                 670 cag tat tct act ggc caa gtc agc gtg gag atc gag tgg gag ctg cag          2064
Gln Tyr Ser Thr Gly Gln Val Ser Val Glu Ile Glu Trp Glu Leu Gln
                675                 680                 685 aag gaa aac agc aag cgc tgg aac ccg gag atc cag tac act tcc aac          2112
Lys Glu Asn Ser Lys Arg Trp Asn Pro Glu Ile Gln Tyr Thr Ser Asn
                690                 695                 700
```

-continued

```
tat tac aag tct aat aat gtt gaa ttt gct gtt aat act gaa ggt gta      2160
Tyr Tyr Lys Ser Asn Asn Val Glu Phe Ala Val Asn Thr Glu Gly Val
705             710             715             720 tat agt gaa ccc cgc ccc att ggc acc aga tac ctg act cgt aat ctg      2208
Tyr Ser Glu Pro Arg Pro Ile Gly Thr Arg Tyr Leu Thr Arg Asn Leu
                725             730             735
```

<210> SEQ ID NO 7
<211> LENGTH: 736
<212> TYPE: PRT
<213> ORGANISM: adeno-associated virus 9

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 8
<211> LENGTH: 2955

```
<212> TYPE: DNA
<213> ORGANISM: Artificial Sequence
<220> FEATURE:
<223> OTHER INFORMATION: CB7.CI.hFXNco
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: TATA_signal
<222> LOCATION: (836)..(838)
<220> FEATURE:
<221> NAME/KEY: Intron
<222> LOCATION: (958)..(1930)
<220> FEATURE:
<221> NAME/KEY: misc_feature
<222> LOCATION: (1942)..(2572)
<223> OTHER INFORMATION: human FXN
<220> FEATURE:
<221> NAME/KEY: polyA_signal
<222> LOCATION: (2611)..(2737)
<223> OTHER INFORMATION: Rabbit globin polyA
<220> FEATURE:
<221> NAME/KEY: repeat_unit
<222> LOCATION: (2826)..(2955)
<223> OTHER INFORMATION: 3' ITR

<400> SEQUENCE: 8
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggact atttacggta     420
aactgcccac ttggcagtac atcaagtgta tcatatgcca gtacgccccc ctattgacgt     480
caatgacggt aaatggcccg cctggcatta tgcccagtac atgaccttat gggactttcc     540
tacttggcag tacatctacg tattagtcat cgctattacc atggtcgagg tgagccccac     600
gttctgcttc actctcccca tctcccccccc ctccccaccc ccaattttgt atttatttat     660
tttttaatta ttttgtgcag cgatggggggc gggggggggg ggggggcgcg cgccaggcgg     720
ggcggggcgg ggcgagggggc ggggcggggc gaggcggaga ggtgcggcgg cagccaatca     780
gagcggcgcg ctccgaaagt ttccttttat ggcgaggcgg cggcggcggc ggccctataa     840
aaagcgaagc gcgcggcggg cggggagtcg ctgcgacgct gccttcgccc cgtgccccgc     900
tccgccgccg cctcgcgccg cccgcccggg ctctgactga ccgcgttact cccacaggtg     960
agcgggcggg acggcccttc tcctccgggc tgtaattagc gcttggttta atgacggctt    1020
gtttcttttc tgtggctgcg tgaaagcctt gaggggctcc gggagggccc tttgtgcggg    1080
gggagcggct cggggggtgc gtgcgtgtgt gtgtgcgtgg ggagcgccgc gtgcggctcc    1140
gcgctgcccg gcggctgtga gcgctgcggg cgcggcgcgg ggctttgtgc gctccgcagt    1200
gtgcgcgagg ggagcgcggc cgggggcggt gccccgcggt gcggggggggg ctgcgagggg    1260
```

```
aacaaaggct gcgtgcgggg tgtgtgcgtg gggggtgag  caggggtgt  gggcgcgtcg      1320 gtcgggctgc aacccccct  gcacccccct ccccgagttg ctgagcacgg cccggcttcg      1380
ggtgcggggc tccgtacggg gcgtggcgcg gggctcgccg tgccgggcgg ggggtggcgg      1440
caggtggggg tgccgggcgg ggcggggccg cctcgggccg gggagggctc gggggagggg      1500
cgcggcggcc cccggagcgc cggcggctgt cgaggcgcgg cgagccgcag ccattgcctt      1560
ttatggtaat cgtgcgagag ggcgcaggga cttcctttgt cccaaatctg tgcggagccg      1620
aaatctggga ggcgccgccg cacccctct  agcgggcgcg gggcgaagcg gtgcggcgcc      1680
ggcaggaagg aaatgggcgg ggagggcctt cgtgcgtcgc cgcgccgccg tccccttctc      1740
cctctccagc ctcggggctg tccgcggggg gacggctgcc ttcggggggg acggggcagg      1800
gcggggttcg gcttctggcg tgtgaccggc ggctctagag cctctgctaa ccatgttcat      1860
gccttcttct ttttcctaca gctcctgggc aacgtgctgg ttattgtgct gtctcatcat      1920
tttggcaaag aattcgccac catgtggaca cttggccgca gagctgttgc tggcctgctt      1980
gcttctccat ctcccgctca gcccagacca ctgaccagtg tgcctagacc tgctgaactg      2040
gcccctctgt gtggcagaag aggcctgaga accgacatcg acgccacatg cacacctaga      2100
agggccagca gcaatcagcg gggcctgaat cagatctgga acgtgaagaa acagagcgtg      2160
tacctgatga acctgagaaa gagcggcacc ctgggacacc ctggaagcct ggacgagaca      2220
acctacgaga gactggccga ggaaaccctg gattccctgg ccgagttctt cgaggacctg      2280
gccgataagc cctacacctt cgaggattac gacgtgtcct ttggcagcgg cgtgctgaca      2340
gtgaaactcg gcggagatct gggcacctac gtgatcaaca gcagacccc  taacaaacag      2400 atctggctga gcagccctag cagcggcccc aagagatacg attggaccgg caagaactgg      2460
gtgtacagcc acgacggcgt gtccctgcac gaactgctgg ctgccgaact gacaaaggcc      2520
ctgaaaacaa agctggacct gtccagcctg gcctactctg gcaaggatgc ctgatgactc      2580
gaggacgggg tgaactacgc ctgaggatcc gatctttttc cctctgccaa aaattatggg      2640
gacatcatga agccccttga gcatctgact tctggctaat aaaggaaatt tattttcatt      2700
gcaatagtgt gttggaattt tttgtgtctc tcactcggaa gcaattcgtt gatctgaatt      2760
tcgaccaccc ataatacccca ttaccctggt agataagtag catggcgggt taatcattaa    2820
ctacaaggaa cccctagtga tggagttggc cactccctct ctgcgcgctc gctcgctcac     2880
tgaggccggg cgaccaaagg tcgcccgacg cccgggcttt gcccgggcgg cctcagtgag     2940
cgagcgagcg cgcag                                                       2955
```

<210> SEQ ID NO 9
<211> LENGTH: 2211
<212> TYPE: DNA
<213> ORGANISM: adeno-associated virus rh.91
<220> FEATURE:
<221> NAME/KEY: CDS
<222> LOCATION: (1)..(2211)

<400> SEQUENCE: 9

```
atg gct gcc gat ggt tat ctt cca gat tgg ctc gag gac aac ctc tct        48
Met Ala Ala Asp Gly Tyr Leu Pro Asp Trp Leu Glu Asp Asn Leu Ser
1               5                   10                  15 gag ggc att cgc gag tgg tgg gcg ctg aaa cct gga gcc ccg aaa ccc        96
Glu Gly Ile Arg Glu Trp Trp Ala Leu Lys Pro Gly Ala Pro Lys Pro
                20                  25                  30 aaa gcc aac cag caa aag cag gac gac ggc cgg ggt ctg gtg ctt cct       144
Lys Ala Asn Gln Gln Lys Gln Asp Asp Gly Arg Gly Leu Val Leu Pro
```

-continued

```
                35                    40                    45 ggc tac aag tac ctc gga ccc ttc aac gga ctc gac aag ggg gag ccc      192
Gly Tyr Lys Tyr Leu Gly Pro Phe Asn Gly Leu Asp Lys Gly Glu Pro
    50                    55                    60 gtc aac gcg gcg gac gca gcg gcc ctc gag cac gac aag gcc tac gac      240
Val Asn Ala Ala Asp Ala Ala Ala Leu Glu His Asp Lys Ala Tyr Asp
65                    70                    75                    80 cag cag ctc aaa gcg ggt gac aat ccg tac ctg cgg tat aac cac gcc      288
Gln Gln Leu Lys Ala Gly Asp Asn Pro Tyr Leu Arg Tyr Asn His Ala
                85                    90                    95 gac gcc gag ttt cag gag cgt ctg caa gaa gat acg tct ttt ggg ggc      336
Asp Ala Glu Phe Gln Glu Arg Leu Gln Glu Asp Thr Ser Phe Gly Gly
                100                   105                   110 aac ctc ggg cga gca gtc ttc cag gcc aag aag cgg gtt ctc gaa cct      384
Asn Leu Gly Arg Ala Val Phe Gln Ala Lys Lys Arg Val Leu Glu Pro
                115                   120                   125 ttt ggt ctg gtt gag gaa gca gct aag acg gct cct gga aag aaa cgt      432
Phe Gly Leu Val Glu Glu Ala Ala Lys Thr Ala Pro Gly Lys Lys Arg
    130                   135                   140 ccg gta gag cag tcg ccc caa gaa cca gac tcc tcc tcg ggc att ggc      480
Pro Val Glu Gln Ser Pro Gln Glu Pro Asp Ser Ser Ser Gly Ile Gly
145                   150                   155                   160 aaa tca ggc cag cag ccc gcc aaa aag aga ctc aat ttc ggt cag act      528
Lys Ser Gly Gln Gln Pro Ala Lys Lys Arg Leu Asn Phe Gly Gln Thr
                165                   170                   175 ggc gac tca gag tca gtc ccc gac cct caa cct ctc gga gaa cct cca      576
Gly Asp Ser Glu Ser Val Pro Asp Pro Gln Pro Leu Gly Glu Pro Pro
                180                   185                   190 gaa acc ccc gct gct gtg gga cct act aca atg gct tca ggc ggt ggc      624
Glu Thr Pro Ala Ala Val Gly Pro Thr Thr Met Ala Ser Gly Gly Gly
                195                   200                   205 gca cca atg gca gac aat aac gaa ggc gcc gac gga gtg ggt aat gcc      672
Ala Pro Met Ala Asp Asn Asn Glu Gly Ala Asp Gly Val Gly Asn Ala
    210                   215                   220 tca gga aat tgg cat tgc gat tcc aca tgg ctg ggc gac aga gtc atc      720
Ser Gly Asn Trp His Cys Asp Ser Thr Trp Leu Gly Asp Arg Val Ile
225                   230                   235                   240 acc acc agc acc cga acc tgg gcc ctt cct acc tac aac aac cac ctc      768
Thr Thr Ser Thr Arg Thr Trp Ala Leu Pro Thr Tyr Asn Asn His Leu
                245                   250                   255 tac aag caa atc tcc agc gct tca acg ggg gcc agt aac gac aac cac      816
Tyr Lys Gln Ile Ser Ser Ala Ser Thr Gly Ala Ser Asn Asp Asn His
                260                   265                   270 tac ttt ggc tac agc acc ccc tgg ggg tat ttt gat ttc aac aga ttc      864
Tyr Phe Gly Tyr Ser Thr Pro Trp Gly Tyr Phe Asp Phe Asn Arg Phe
                275                   280                   285 cac tgc cac ttc tca cca cgt gac tgg cag cga ctc att aac aac aac      912
His Cys His Phe Ser Pro Arg Asp Trp Gln Arg Leu Ile Asn Asn Asn
                290                   295                   300 tgg gga ttc cgg ccc aag aga ctc aac ttc aag ctc ttc aac atc cag      960
Trp Gly Phe Arg Pro Lys Arg Leu Asn Phe Lys Leu Phe Asn Ile Gln
305                   310                   315                   320 gtc aag gag gtc acg acg aat gat ggc gtc aca acc atc gct aat aac     1008
Val Lys Glu Val Thr Thr Asn Asp Gly Val Thr Thr Ile Ala Asn Asn
                325                   330                   335 ctt acc agc acg gtt caa gtg ttc tcg gac tcg gag tac cag ctg ccg     1056
Leu Thr Ser Thr Val Gln Val Phe Ser Asp Ser Glu Tyr Gln Leu Pro
                340                   345                   350 tac gtc ctc ggt tct gcg cac cag ggc tgc ctc cct ccg ttc ccg gcg     1104
```

-continued

---

```
                Tyr Val Leu Gly Ser Ala His Gln Gly Cys Leu Pro Pro Phe Pro Ala
                        355                 360                 365 gac gta ttc atg att cct cag tac ggc tac cta acg ctc aac aat ggc          1152
Asp Val Phe Met Ile Pro Gln Tyr Gly Tyr Leu Thr Leu Asn Asn Gly
        370                 375                 380 agc cag gcc gta gga cgt tca tcc ttt tat tgc ctg gaa tat ttc cca          1200
Ser Gln Ala Val Gly Arg Ser Ser Phe Tyr Cys Leu Glu Tyr Phe Pro
385                 390                 395                 400 tct caa atg ctg aga acg ggc aac aac ttt acc ttc agc tac acc ttt          1248
Ser Gln Met Leu Arg Thr Gly Asn Asn Phe Thr Phe Ser Tyr Thr Phe
                405                 410                 415 gaa gat gtg cct ttc cac agc agt tac gcg cac agc cag agc ctg gac          1296
Glu Asp Val Pro Phe His Ser Ser Tyr Ala His Ser Gln Ser Leu Asp
                420                 425                 430 agg cta atg aat cct cta atc gac cag tac ctg tat tac cta aac aga          1344
Arg Leu Met Asn Pro Leu Ile Asp Gln Tyr Leu Tyr Tyr Leu Asn Arg
                435                 440                 445 act cag aat caa tcc gga agt gca caa aac aag gac ttg ctg ttt agc          1392
Thr Gln Asn Gln Ser Gly Ser Ala Gln Asn Lys Asp Leu Leu Phe Ser
        450                 455                 460 cgg ggg tct cca gct ggc atg tct gtt cag ccc aaa aac tgg cta ccc          1440
Arg Gly Ser Pro Ala Gly Met Ser Val Gln Pro Lys Asn Trp Leu Pro
465                 470                 475                 480 ggg ccc tgt tac cga cag cag cgt gtt tct aaa aca aaa aca gac aac          1488
Gly Pro Cys Tyr Arg Gln Gln Arg Val Ser Lys Thr Lys Thr Asp Asn
                485                 490                 495 aac aac agc aac ttt acc tgg act ggt gcc tcc aaa tac aat ctg aac          1536
Asn Asn Ser Asn Phe Thr Trp Thr Gly Ala Ser Lys Tyr Asn Leu Asn
                500                 505                 510 gga cgt gaa tcc atc att aac cct ggc acc gct atg gca tcc cac aag          1584
Gly Arg Glu Ser Ile Ile Asn Pro Gly Thr Ala Met Ala Ser His Lys
                515                 520                 525 gac gac gaa gac aaa ttt ttt ccc atg agc ggt gtt atg att ttt ggc          1632
Asp Asp Glu Asp Lys Phe Phe Pro Met Ser Gly Val Met Ile Phe Gly
        530                 535                 540 aaa gaa aat gca gga gca tca aac act gca tta gac aat gtt atg att          1680
Lys Glu Asn Ala Gly Ala Ser Asn Thr Ala Leu Asp Asn Val Met Ile
545                 550                 555                 560 aca gat gaa gag gaa att aaa gct acc aac ccc gtg gcc acc gag aga          1728
Thr Asp Glu Glu Glu Ile Lys Ala Thr Asn Pro Val Ala Thr Glu Arg
                565                 570                 575 ttt gga act gtg gca gtc aat ctc caa agc agc aat aca gac cct gca          1776
Phe Gly Thr Val Ala Val Asn Leu Gln Ser Ser Asn Thr Asp Pro Ala
                580                 585                 590 aca gga gac gtg cat gtc atg ggg gct tta cct ggc atg gtg tgg caa          1824
Thr Gly Asp Val His Val Met Gly Ala Leu Pro Gly Met Val Trp Gln
                595                 600                 605 gac aga gac gtg tac ctg cag ggt ccc att tgg gcc aag att cct cac          1872
Asp Arg Asp Val Tyr Leu Gln Gly Pro Ile Trp Ala Lys Ile Pro His
        610                 615                 620 acg gat gga cac ttt cac ccg tct cct ctt atg ggc ggc ttt gga ctt          1920
Thr Asp Gly His Phe His Pro Ser Pro Leu Met Gly Gly Phe Gly Leu
625                 630                 635                 640 aag cac ccg cct cct cag atc ctc atc aaa aac acg cct gtt cct gcg          1968
Lys His Pro Pro Pro Gln Ile Leu Ile Lys Asn Thr Pro Val Pro Ala
                645                 650                 655 aat cct ccg gca gag ttt tcg gct aca aag ttt gct tca ttc atc acc          2016
Asn Pro Pro Ala Glu Phe Ser Ala Thr Lys Phe Ala Ser Phe Ile Thr
        660                 665                 670
```

-continued

```
cag tac tcc aca gga caa gtg agc gtg gaa att gaa tgg gag ctg cag        2064
Gln Tyr Ser Thr Gly Gln Val Ser Val Glu Ile Glu Trp Glu Leu Gln
        675             680             685 aaa gaa aac agt aag cgc tgg aat cct gaa gtg cag tac acc tcc aac        2112
Lys Glu Asn Ser Lys Arg Trp Asn Pro Glu Val Gln Tyr Thr Ser Asn
        690             695             700 tac gcg aaa tct gcc aac gtt gat ttc act gtg gac aac aat gga ctt        2160
Tyr Ala Lys Ser Ala Asn Val Asp Phe Thr Val Asp Asn Asn Gly Leu
705             710             715             720 tat act gag cct cgc ccc att ggc acc cgt tac ctt acc cgt ccc ctt        2208
Tyr Thr Glu Pro Arg Pro Ile Gly Thr Arg Tyr Leu Thr Arg Pro Leu
                725             730             735 taa                                                                     2211

<210> SEQ ID NO 10
<211> LENGTH: 736
<212> TYPE: PRT
<213> ORGANISM: adeno-associated virus rh.91

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Glu Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285
```

-continued

```
His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
                435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
    515                 520                 525

Asp Asp Glu Asp Lys Phe Phe Pro Met Ser Gly Val Met Ile Phe Gly
    530                 535                 540

Lys Glu Asn Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Asn Thr Asp Pro Ala
                580                 585                 590

Thr Gly Asp Val His Val Met Gly Ala Leu Pro Gly Met Val Trp Gln
                595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Val Gln Tyr Thr Ser Asn
    690                 695                 700
```

-continued

```
Tyr Ala Lys Ser Ala Asn Val Asp Phe Thr Val Asp Asn Asn Gly Leu
705             710                 715                 720

Tyr Thr Glu Pro Arg Pro Ile Gly Thr Arg Tyr Leu Thr Arg Pro Leu
                725                 730                 735

<210> SEQ ID NO 11
<211> LENGTH: 2211
<212> TYPE: DNA
<213> ORGANISM: adeno-associated virus rh.91
<220> FEATURE:
<221> NAME/KEY: misc_feature
<222> LOCATION: (1)..(2211)
<223> OTHER INFORMATION: AAVrh.91

<400> SEQUENCE: 11
atggctgctg acggttatct tccagattgg ctcgaggaca acctttctga aggcattcgt      60
gagtggtggg ctctgaaacc tggagcccct aaacccaaag cgaaccaaca aaagcaggac     120
gacggccggg gtcttgtgct tccgggttac aaatacctcg acccttcaa cggactcgac      180 aaaggagagc cggtcaacgc ggcggacgcg gcagccctcg aacacgacaa agcttacgac     240
cagcagctca aggccggtga caacccgtac ctccggtaca ccacgccga cgccgagttt      300 caggagcgtc ttcaagaaga tacgtctttt gggggcaacc ttggcagagc agtcttccag     360
gccaaaaaga gggttcttga gccttttggt ctggttgagg aagcagctaa aacggctcct     420
ggaaagaaga ggcctgtaga gcagtctcct caggaaccgg actcatcatc tggtattggc     480
aaatcgggcc agcagcctgc caaaaaaaga ctaaatttcg gtcagactgg cgactcagag     540
tcagtccccg accctcaacc tctcggagaa cctccagaaa cccccgctgc tgtgggacct     600
actacaatgg cttcaggcgg tggcgcacca atggcagaca taacgaagg cgccgacgga      660 gtgggtaatg cctcaggaaa ttggcattgc gattccacat ggctgggcga cagagtcatc     720
accaccagca cccgaacctg ggcccttcct acctacaaca accacctcta caagcaaatc     780
tccagcgctt caacggggc cagtaacgac aaccactact ttggctacag caccccctgg      840
gggtattttg atttcaacag attccactgc cacttctcac cacgtgactg cagcgactc      900 attaacaaca ctgggggatt ccggcccaag agactcaact tcaagctctt caacatccag     960
gtcaaggagg tcacgacgaa tgatggcgtc acaaccatcg ctaataacct taccagcacg    1020
gttcaagtgt ctcggactc ggagtaccag ctgccgtacg tcctcggttc tgcgcaccag     1080
ggctgcctcc ctccgttccc ggcggacgta ttcatgattc ctcagtatgg atacctcacc    1140
ctgaacaacg gaagtcaagc ggtgggacgc tcatcctttt actgcctgga gtacttccct    1200
tcgcagatgc taaggactgg aaataacttc accttcagct ataccttcga ggatgtacct    1260
tttcacagca gctacgctca cagccagagt ttggatcgct tgatgaatcc tcttattgat    1320
cagtatctgt actacctgaa cagaacgcaa aatcaatctg gaagtgcaca aaacaaggac    1380 ctgctttta gccggggggtc tcctgctggc atgtctgttc agcccaaaaa ttggctacct    1440
gggccctgct accggcaaca gagagtttca aagactaaaa cagacaacaa caacagtaac    1500
tttacctgga caggtgccag caaatataat ctcaatggcc gcgaatcgat cattaatcca    1560
ggaaccgcta tggccagtca caggacgat gaagacaaat ttttccctat gagcggcgtt    1620
atgatatttg gcaaagaaaa tgcaggagca agtaacactg cattagataa tgtaatgatt    1680
acggatgaag aagagattaa agctaccaat cctgtggcaa cagagagatt tggaactgtg    1740
gcagtcaact gcagagctc aaatacagac cccgcaactg agacgtcca tgtcatgggg     1800 gccttacctg gcatggtgtg gcaagatcgt gacgtgtacc ttcaggacc tatctgggca    1860
```

-continued

```
aagattcctc acacggatgg acactttcat ccttctcctc tgatgggagg ctttggactg    1920
aaacatccgc ctcctcaaat cctcatcaaa aatactccgg taccggcaaa tcctccggca    1980
gagttcagcg ctacaaagtt tgcttcattt atcactcagt actccactgg acaggtcagc    2040
gtggaaattg agtgggagct acagaaagaa aacagcaaac gttggaatcc agaggtgcag    2100
tacacttcca actacgcgaa gtctgccaat gtggacttta ctgtagacaa caatggtctt    2160
tatactgaac ctcgccctat tggaacccgg tatctcacac gacccttgta a           2211
```

```
<210> SEQ ID NO 12
<211> LENGTH: 2954
<212> TYPE: DNA
<213> ORGANISM: Artificial Sequence
<220> FEATURE:
<223> OTHER INFORMATION: vecotr genome AAV.CB7.CI.hFXNco.RBG
<220> FEATURE:
<221> NAME/KEY: repeat_region
<222> LOCATION: (1)..(130)
<223> OTHER INFORMATION: 5'ITR
<220> FEATURE:
<221> NAME/KEY: repeat_region
<222> LOCATION: (198)..(579)
<223> OTHER INFORMATION: CMV IE enhancer
<220> FEATURE:
<221> NAME/KEY: promoter
<222> LOCATION: (585)..(862)
<223> OTHER INFORMATION: Chicken beta-actin promoter
<220> FEATURE:
<221> NAME/KEY: TATA_signal
<222> LOCATION: (836)..(862)
<223> OTHER INFORMATION: TATA
<220> FEATURE:
<221> NAME/KEY: Intron
<222> LOCATION: (957)..(1929)
<223> OTHER INFORMATION: chicken beta-actin intron
<220> FEATURE:
<221> NAME/KEY: Intron
<222> LOCATION: (957)..(1929)
<223> OTHER INFORMATION: chimeric intron
<220> FEATURE:
<221> NAME/KEY: misc_feature
<222> LOCATION: (1941)..(2570)
<223> OTHER INFORMATION: hFXNco
<220> FEATURE:
<221> NAME/KEY: polyA_signal
<222> LOCATION: (2610)..(2736)
<223> OTHER INFORMATION: Rabbit globin poly A
<220> FEATURE:
<221> NAME/KEY: repeat_region
<222> LOCATION: (2825)..(2954)
<223> OTHER INFORMATION: 3'ITR

<400> SEQUENCE: 12
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggagt atttacggta     420
aactgcccac ttggcagtac atcaagtgta tcatatgcca agtacgcccc ctattgacgt     480
caatgacggt aaatggcccg cctggcatta tgcccagtac atgaccttat gggactttcc     540
tacttggcag tacatctacg tattagtcat cgctattacc atggtcgagg tgagccccac     600
```

-continued

```
gttctgcttc actctcccca tctcccccc ctccccaccc ccaattttgt atttatttat    660
tttttaatta ttttgtgcag cgatgggggc gggggggggg ggggggcgcg cgccaggcgg    720
ggcggggcgg ggcgaggggc ggggcggggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cggggagtcg ctgcgcgctg ccttcgcccc gtgccccgct    900
ccgccgccgc ctcgcgccgc ccgccccggc tctgactgac cgcgttactc ccacaggtga    960
gcgggcggga cggcccttct cctccgggct gtaattagcg cttggtttaa tgacggcttg   1020 tttctttttct gtggctgcgt gaaagccttg aggggctccg ggagggccct ttgtgcgggg   1080
ggagcggctc ggggggtgcg tgcgtgtgtg tgtgcgtggg gagcgccgcg tgcggctccg   1140
cgctgcccgg cggctgtgag cgctgcgggc gcggcgcggg gctttgtgcg ctccgcagtg   1200
tgcgcgaggg gagcgcggcc gggggcggtg ccccgcggtg cgggggggggc tgcgagggga   1260 acaaaggctg cgtgcggggt gtgtgcgtgg gggggtgagc aggggggtgtg ggcgcgtcgg   1320 tcgggctgca accccccctg cacccccctc cccgagttgc tgagcacggc ccggcttcgg   1380
gtgcggggct ccgtacgggg cgtggcgcgg ggctcgccgt gccgggcggg gggtggcggc   1440 aggtggggggt gccgggcggg gcggggccgc ctcgggccgg ggagggctcg ggggaggggc   1500
gcggcggccc ccggagcgcc ggcggctgtc gaggcgcggc gagccgcagc cattgccttt   1560
tatggtaatc gtgcgagagg gcgcagggac ttcctttgtc ccaaatctgt gcggagccga   1620
aatctgggag gcgccgccgc accccctcta gcgggcgcgg ggcgaagcgg tgcggcgccg   1680
gcaggaagga aatgggcggg gagggccttc gtgcgtcgcc gcgccgccgt ccccttctcc   1740
ctctccagcc tcgggctgt ccgcgggggg acggctgcct tcggggggga cggggcaggg   1800
cggggttcgg cttctggcgt gtgaccggcg gctctagagc ctctgctaac catgttcatg   1860
ccttcttctt tttcctacag ctcctgggca acgtgctggt tattgtgctg tctcatcatt   1920
ttggcaaaga attcgccacc atgtggacac ttggccgcag agctgttgct ggcctgcttg   1980
cttctccatc tcccgctcaa gcccagacac tgaccagagt gcctagacct gctgaactgg   2040
cccctctgtg tggcagaaga ggcctgagaa ccgacatcga cgccacatgc acacctagaa   2100
gggccagcag caatcagcgg ggcctgaatc agatctggaa cgtgaagaaa cagagcgtgt   2160
acctgatgaa cctgagaaag agcggcaccc tgggacaccc tggaagcctg gacgagacaa   2220
cctacgagac actggccgag gaaaccctgg attccctggc cgagttcttc gaggacctgg   2280
ccgataagcc ctacaccttc gaggattacg acgtgtcctt tggcagcggc gtgctgacag   2340
tgaaactcgg cggagatctg ggcacctacg tgatcaacaa gcagacccct aacaaacaga   2400
tctggctgag cagccctagc agcggcccca agagatacga ttggaccggc aagaactggg   2460
tgtacagcca cgacggcgtg tccctgcacg aactgctggc tgccgaactg acaaaggccc   2520
tgaaaacaaa gctggacctg tccagcctgg cctactctgg caaggatgcc tgatgactcg   2580
aggacggggt gaactacgcc tgaggatccg atcttttttcc ctctgccaaa aattatgggg   2640
acatcatgaa gcccccttgag catctgactt ctggctaata aaggaaattt attttcattg   2700
caatagtgtg ttggaatttt ttgtgtctct cactcggaag caattcgttg atctgaattt   2760
cgaccaccca taatacccat taccctggta gataagtagc atggcgggtt aatcattaac   2820
```

-continued

```
tacaaggaac ccctagtgat ggagttggcc actccctctc tgcgcgctcg ctcgctcact    2880
gaggccgggc gaccaaaggt cgcccgacgc ccgggctttg cccgggcggc ctcagtgagc    2940
gagcgagcgc gcag                                                      2954
```